US008467061B2

(12) United States Patent
McCaffrey et al.

(10) Patent No.: US 8,467,061 B2
(45) Date of Patent: Jun. 18, 2013

(54) INTEGRATED ANALYTICAL SYSTEM AND METHOD

(75) Inventors: Nathaniel Joseph McCaffrey, Hampton Falls, NH (US); Stephen Turner, Menlo Park, CA (US); Ravi Saxena, San Jose, CA (US); Scott Edward Helgesen, Palo Alto, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 155 days.

(21) Appl. No.: 13/031,122

(22) Filed: Feb. 18, 2011

(65) Prior Publication Data

US 2012/0019828 A1    Jan. 26, 2012

Related U.S. Application Data

(60) Provisional application No. 61/306,235, filed on Feb. 19, 2010, provisional application No. 61/387,916, filed on Sep. 29, 2010, provisional application No. 61/410,189, filed on Nov. 4, 2010.

(51) Int. Cl.
*G02B 6/02* (2006.01)

(52) U.S. Cl.
USPC ........ 356/432; 356/318; 356/319; 422/82.11; 385/123

(58) Field of Classification Search
USPC ............... 356/432–444, 317–319; 385/12, 385/123, 129; 422/102, 165, 57, 82.11; 435/6, 435/287.2
See application file for complete search history.

(56) References Cited

U.S. PATENT DOCUMENTS

| 5,082,629 A | 1/1992 | Burgess, Jr. et al. |
| 5,094,517 A | 3/1992 | Franke |
| 5,157,262 A | 10/1992 | Marsoner et al. |
| 5,159,661 A | 10/1992 | Ovshinsky et al. |
| 5,173,747 A | 12/1992 | Boiarski et al. |
| 5,192,502 A | 3/1993 | Attridge et al. |
| 5,233,673 A | 8/1993 | Vali et al. |
| 5,239,178 A | 8/1993 | Derndinger et al. |
| 5,439,647 A | 8/1995 | Saini |

(Continued)

FOREIGN PATENT DOCUMENTS

| EP | 1105529 B1 | 11/2005 |
| EP | 1871902 B1 | 10/2006 |

(Continued)

OTHER PUBLICATIONS

Psaltis, Demetri, et al., "Developing Optofluidic Technology through the Fusion of Microfluidics and Optics," Nature, v. 442, p. 381-386, Jul. 27, 2006.

(Continued)

*Primary Examiner* — Sang Nguyen
(74) *Attorney, Agent, or Firm* — Morgan, Lewis & Bockius LLP

(57) ABSTRACT

An analytical assembly within a unified device structure for integration into an analytical system. The analytical assembly is scalable and includes a plurality of analytical devices, each of which includes a reaction cell, an optical sensor, and at least one optical element positioned in optical communication with both the reaction cell and the sensor and which delivers optical signals from the cell to the sensor. Additional elements are optionally integrated into the analytical assembly. Methods for forming and operating the analytical system are also disclosed.

13 Claims, 42 Drawing Sheets

U.S. PATENT DOCUMENTS

| | | |
|---|---|---|
| 5,446,534 A | 8/1995 | Goldman |
| 5,470,710 A | 11/1995 | Weiss et al. |
| 5,545,531 A | 8/1996 | Rava et al. |
| 5,578,832 A | 11/1996 | Trulson et al. |
| 5,605,662 A | 2/1997 | Heller et al. |
| 5,631,734 A | 5/1997 | Stern et al. |
| 5,677,196 A | 10/1997 | Herron et al. |
| 5,695,934 A | 12/1997 | Brenner |
| 5,744,305 A | 4/1998 | Fodor et al. |
| 5,812,709 A | 9/1998 | Arai et al. |
| 5,821,058 A | 10/1998 | Smith et al. |
| 5,832,165 A | 11/1998 | Reichert et al. |
| 5,867,266 A | 2/1999 | Craighead et al. |
| 5,919,712 A | 7/1999 | Herron et al. |
| 6,071,748 A | 6/2000 | Modlin et al. |
| 6,192,168 B1 | 2/2001 | Feldstein et al. |
| 6,210,896 B1 | 4/2001 | Chan |
| 6,236,945 B1 | 5/2001 | Simpson et al. |
| 6,263,286 B1 | 7/2001 | Gilmanshin et al. |
| 6,325,977 B1 | 12/2001 | Theil |
| 6,388,788 B1 | 5/2002 | Harris et al. |
| 6,437,345 B1 | 8/2002 | Bruno-Raimondi et al. |
| 6,438,279 B1 | 8/2002 | Craighead et al. |
| 6,603,537 B1 | 8/2003 | Dietz et al. |
| 6,611,634 B2 | 8/2003 | Herron et al. |
| 6,690,002 B2 | 2/2004 | Kuroda et al. |
| 6,699,655 B2 | 3/2004 | Nikiforov et al. |
| 6,784,982 B1 | 8/2004 | Blumenfeld et al. |
| 6,800,860 B2 | 10/2004 | Dietz et al. |
| 6,818,395 B1 | 11/2004 | Quake et al. |
| 6,867,851 B2 | 3/2005 | Blumenfeld et al. |
| 6,919,211 B1 | 7/2005 | Fodor et al. |
| 6,979,830 B2 | 12/2005 | Dietz et al. |
| 6,982,146 B1 | 1/2006 | Schneider et al. |
| 7,056,661 B2 | 6/2006 | Korlach et al. |
| 7,057,832 B2 * | 6/2006 | Wu et al. ............... 359/811 |
| 7,075,695 B2 | 7/2006 | Gronbach |
| 7,081,954 B2 | 7/2006 | Sandstrom |
| 7,083,914 B2 | 8/2006 | Seul et al. |
| 7,130,041 B2 | 10/2006 | Bouzid et al. |
| 7,135,667 B2 | 11/2006 | Oldham et al. |
| 7,139,074 B2 | 11/2006 | Reel |
| 7,145,645 B2 | 12/2006 | Blumenfeld et al. |
| 7,150,997 B2 | 12/2006 | Kovacs |
| 7,175,811 B2 | 2/2007 | Bach et al. |
| 7,189,361 B2 | 3/2007 | Carson |
| 7,197,196 B2 | 3/2007 | Lin et al. |
| 7,199,357 B1 | 4/2007 | Oldham et al. |
| 7,209,836 B1 | 4/2007 | Schermer et al. |
| 7,227,128 B2 | 6/2007 | Sagatelyan |
| RE39,772 E | 8/2007 | Herron et al. |
| 7,302,348 B2 | 11/2007 | Ghosh et al. |
| 7,315,019 B2 | 1/2008 | Turner et al. |
| 7,323,681 B1 | 1/2008 | Oldham et al. |
| 7,400,380 B2 | 7/2008 | Hahn |
| 7,767,441 B2 | 8/2010 | Chiou et al. |
| 7,811,810 B2 | 10/2010 | Chiou et al. |
| 8,247,216 B2 * | 8/2012 | Zaccarin et al. ........ 435/283.1 |
| 2002/0034457 A1 | 3/2002 | Reichert et al. |
| 2002/0110839 A1 | 8/2002 | Bach et al. |
| 2002/0113213 A1 | 8/2002 | Amirkhanian et al. |
| 2002/0146047 A1 | 10/2002 | Bendett et al. |
| 2003/0044781 A1 | 3/2003 | Korlach et al. |
| 2003/0132406 A1 | 7/2003 | Waldhausl et al. |
| 2003/0138180 A1 | 7/2003 | Kondo |
| 2003/0174324 A1 * | 9/2003 | Sandstrom ............... 356/317 |
| 2003/0174992 A1 * | 9/2003 | Levene et al. ........... 385/129 |
| 2004/0040868 A1 | 3/2004 | Denuzzio et al. |
| 2004/0046128 A1 | 3/2004 | Abel et al. |
| 2004/0197793 A1 | 10/2004 | Hassibi et al. |
| 2004/0249227 A1 | 12/2004 | Klapproth et al. |
| 2005/0014178 A1 | 1/2005 | Holm-Kennedy |
| 2005/0135974 A1 * | 6/2005 | Harvey et al. ............ 422/102 |
| 2005/0175273 A1 | 8/2005 | Iida et al. |
| 2005/0201899 A1 | 9/2005 | Weisbuch |
| 2005/0206895 A1 * | 9/2005 | Salmelainen ............ 356/318 |
| 2006/0060766 A1 | 3/2006 | Turner et al. |
| 2006/0103850 A1 | 5/2006 | Alphonse et al. |
| 2007/0036511 A1 * | 2/2007 | Lundquist et al. ......... 385/147 |
| 2007/0099212 A1 | 5/2007 | Harris |
| 2007/0146701 A1 | 6/2007 | Kiesel et al. |
| 2007/0188746 A1 | 8/2007 | Kraus et al. |
| 2007/0196815 A1 * | 8/2007 | Lappe et al. ................. 435/4 |
| 2008/0020938 A1 | 1/2008 | Kaplan |
| 2008/0039339 A1 | 2/2008 | Hassibi |
| 2008/0161195 A1 | 7/2008 | Turner et al. |
| 2008/0212960 A1 | 9/2008 | Lundquist |
| 2009/0146076 A1 | 6/2009 | Chiou et al. |
| 2009/0247414 A1 | 10/2009 | Obradovic et al. |
| 2009/0311774 A1 | 12/2009 | Chiou et al. |
| 2010/0121582 A1 | 5/2010 | Pan et al. |
| 2010/0256918 A1 | 10/2010 | Chen et al. |
| 2011/0117637 A1 | 5/2011 | Gray et al. |
| 2012/0014837 A1 * | 1/2012 | Fehr et al. .............. 422/82.11 |

FOREIGN PATENT DOCUMENTS

| | | |
|---|---|---|
| EP | 2362209 A2 | 8/2011 |
| KR | 10-2005-0088782 A | 9/2005 |
| WO | WO 91/06678 A1 | 5/1991 |
| WO | WO 01/16375 A2 | 3/2001 |
| WO | WO 2004/100068 A2 | 11/2004 |
| WO | WO 2006/116726 A2 | 2/2006 |
| WO | WO 2006/135782 A2 | 12/2006 |
| WO | WO 2007/002367 A2 | 1/2007 |
| WO | WO 2007/011549 A1 | 1/2007 |
| WO | WO 2008/002765 A2 | 1/2008 |
| WO | WO 2009/056065 A1 | 5/2009 |
| WO | WO 2009/131535 A1 | 10/2009 |
| WO | WO 2009/149125 | 12/2009 |
| WO | WO 2010/051773 A1 | 5/2010 |
| WO | WO 2010/102567 A1 | 9/2010 |
| WO | WO 2011/076132 A2 | 6/2011 |

OTHER PUBLICATIONS

Bernini et al., "Polymer-on-glass waveguide structure for efficient fluorescence-based optical biosensors" Proc. SPIE (2005) 5728:101-111.

Boiarski et al., "Integrated-optic sensor with macro-flow cell" Proc. SPIE (1992) 1793:199-211.

Budach et al., "Planar waveguides as high-performance sensing platforms for fluorescence-based multiplexed oligonucleotide hybridization assays" Anal. Chem. (1999) 71(16):3347-3355.

Cottier et al., "Thickness-modulated waveguides for integrated optical sensing" Proc. SPIE (2002) 4616:53-63.

Deopura, M. et al., "Dielectric omnidirectional visible reflector" Optics Lett (2001) 26(15):1197-1199.

Duveneck et al., "Planar waveguides for ultra-high sensitivity of the analysis of nucleic acids" Anal Chem Acta (2002) 469:49-61.

Feldstein et al., "Array Biosensor: optical and fluidics systems" J. Biomed Microdev. (1999) 1:139-153.

Fink, Y. et al., "A dielectric omnidirectional reflector" Science (1998) 282:1679-1682.

Herron et al., "Orientation and Activity of Immobilized Antibodies" Biopolymers at Interfaces 2nd Ed (2003) Surfactant Science Series vol. 110, Marcel Dekker, NY pp. 115-163.

Levene, M.J. et al., "Zero-mode waveguides for single-molecule analysis at high concentrations" Science (2003) 299:682-686.

Salama et al., "Modeling and simulations of luminescence detection platforms" Biosensors & Bioelectronics (2004) 19:1377-1386.

Weissman et al., "Mach-Zhnder type, evanescent-wave bio-sensor, in ion-exchanged glass, using periodically segmented waveguide" Proc. Spie (1999) 3596:210-216.

Wu et al., "DNA and protein microarray printing on silicon nitride waveguide surfaces" Biosensors and Bioelectronics (2006) 21:1252-1263.

Yariv, A. et al., "Periodic structures for integrated optics" IEEE J Quantum Elec (1977) QE-13(4):233-253.

* cited by examiner

Top view of photonic and fluidic ports on top half of durable ATE socket

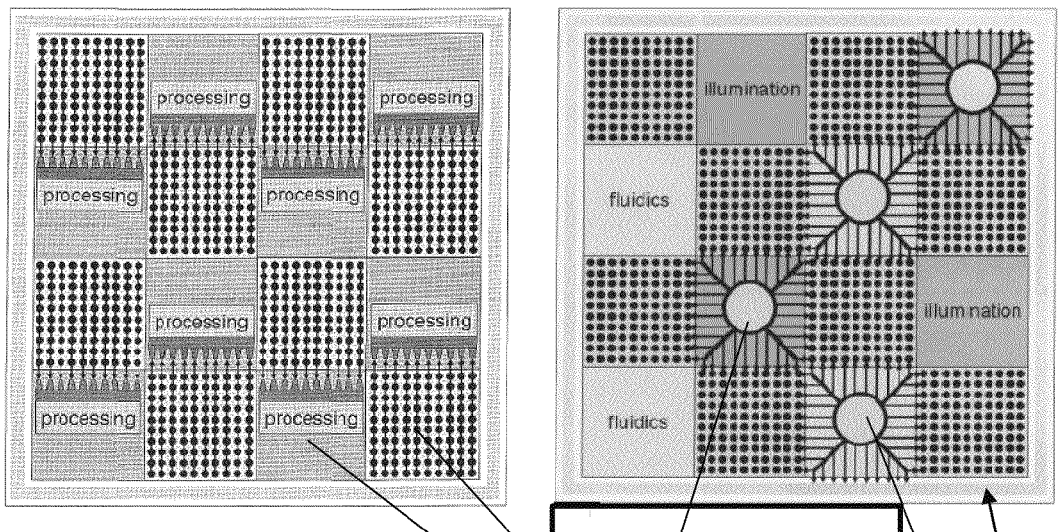
75 70 72
Figure 13A
Figure 13B 73
71
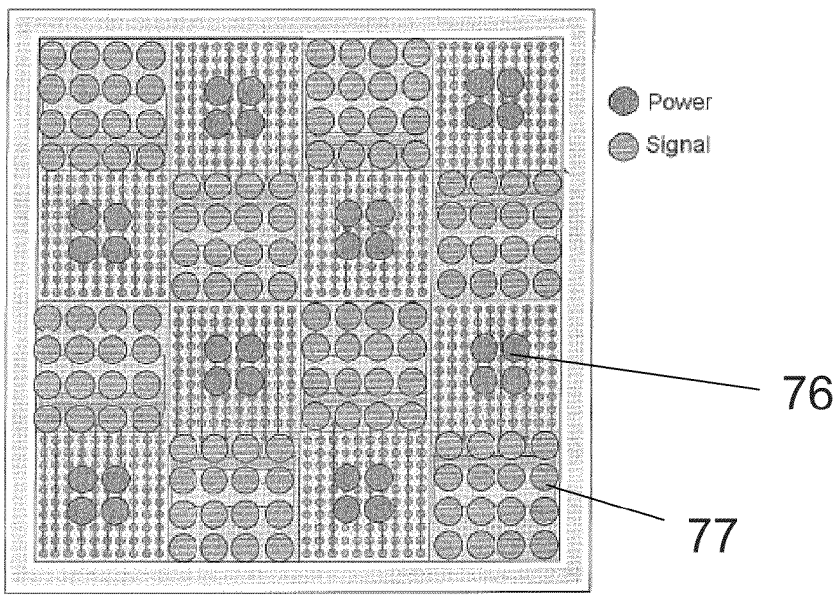
● Power
● Signal
76
77
Figure 13C

Smart pixel for event logging with multi-species discrimination

Compact CMOS Programmable Trigger Circuit $$v_{i1} - V_{GS1} + V_{GS2} - v_{i2} = 0$$

Differential Amplifier for Trigger Circuit

INTEGRATED ANALYTICAL SYSTEM AND METHOD

CROSS-REFERENCE TO RELATED APPLICATIONS

This application claims priority to U.S. Provisional Application No. 61/306,235 filed Feb. 19, 2010 and entitled INTEGRATED ANALYTICAL DEVICES AND SYSTEMS, U.S. Provisional Patent Application No. 61/387,916 filed Sep. 29, 2010 and entitled INTEGRATED ANALYTICAL SYSTEM AND METHOD, U.S. Provisional Patent Application No. 61/410,189 filed Nov. 4, 2010 and entitled ILLUMINATION OF INTEGRATED ANALYTICAL SYSTEMS, and U.S. patent application Ser. No. 13/031,146 filed Feb. 18, 2011 and entitled OPTICS COLLECTION AND DETECTION SYSTEM AND METHOD, the entire contents of which applications is incorporated herein for all purposes by this reference.

STATEMENT REGARDING FEDERALLY SPONSORED RESEARCH

Not Applicable.

BACKGROUND OF THE INVENTION

Analytical technologies continue to advance far beyond the test tube scale evaluations of the 19$^{th}$ and 20$^{th}$ centuries, and have progressed to the point where researchers can look at very specific interactions in vivo, in vitro, at the cellular level, and even at the level of individual molecules. This progression is driven not just by the desire to understand important reactions in their purest form, but also by the realization that seemingly minor or insignificant reactions in living systems can prompt a cascade of other events that could potentially unleash a life or death result.

In this progression, these analyses not only have become more focused on lesser events, but also have had to become appropriately more sensitive, in order to be able to monitor such reactions. In increasing sensitivity to the levels of cellular or even single molecular levels, one may inherently increase the sensitivity of the system to other non-relevant signals, or 'noise'. In some cases, the noise level can be of sufficient magnitude that it partially or completely obscures the desired signals, i.e., those corresponding to the analysis of interest. Accordingly, it is desirable to be able to increase sensitivity of detection while maintaining the signal-to-noise ratio.

There is a continuing need to increase the performance of analytical systems and reduce the cost associated with manufacturing and using the system. In particular, there is a continuing need to increase the throughput of analytical systems. There is a continuing need to reduce the size and complexity of analytical system. There is a continuing need for analytical systems that have flexible configurations and are easily scalable.

The present invention provides devices, systems and methods for overcoming the above problems in addition to other benefits.

BRIEF SUMMARY OF THE INVENTION

The present invention is generally directed to an integrated analytical device that includes, within a single unified structure, a plurality of reaction cells, at least one detector element, and an optical element for delivering an optical signal from a respective reaction cell to the detector element. A variety of elements may be integrated into the device structure that enhances the performance and scalability of the device. Various aspects of the invention are directed to an analytical system employing an integrated analytical device and elements and methods for efficient integration.

The methods and apparatuses of the present invention have other features and advantages which will be apparent from or are set forth in more detail in the accompanying drawings, which are incorporated herein, and the following Detailed Description of the Invention, which together serve to explain certain principles of the present invention.

BRIEF DESCRIPTION OF THE DRAWINGS

FIG. 13 shows various layers in an optode array chip. FIG. 13A is a layer having detectors and processing components, FIG. 13B is a top view of the device showing distributed fluidics and illumination systems. FIG. 13C shows the bottom of the device having electrical contacts for connections with distributed power and signal systems. FIG. 13D schematically illustrates the use of a hydrophobic/hydrophilic surface interaction in joining and aligning component substrates. FIG. 13E schematically illustrates the process introducing spacing elements between the substrates.

DETAILED DESCRIPTION OF THE INVENTION

Figure 1A:
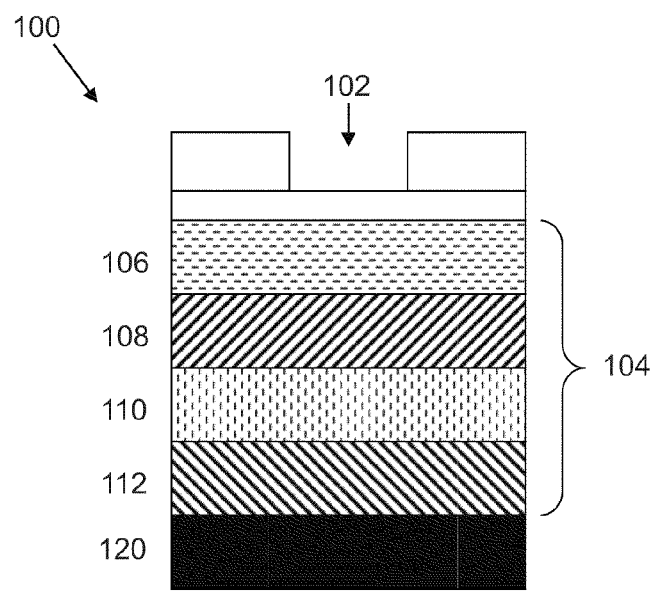
FIG. 1A is a block diagram of an optical analytical device architecture in accordance with the present invention.

Reference will now be made in detail to the various embodiments of the invention, examples of which are illustrated in the accompanying drawings. While the invention will be described in conjunction with the various embodiments, it will be understood that they are not intended to limit the invention to those embodiments. On the contrary, the invention is intended to cover alternatives, modifications and equivalents, which may be included within the spirit and scope of the invention as defined by the appended claims.

I. Optical Analyses

The present invention is generally directed to improved systems, methods and devices for use in optical analyses, and particularly, optical analyses of biological and/or chemical samples and reactions. In general, these optical analyses seek to gather and detect one or more optical signals, the appearance or disappearance of which, or localization of which, is indicative of a given chemical or biological reaction and/or the presence or absence of a given substance within a sample material. In some cases, the reactants, their products, or substance of interest (all of which are referred to as reactants herein) inherently present an optically detectable signal which can be detected. In other cases, reactants are provided with exogenous labeling groups to facilitate their detection. Useful labeling groups include fluorescent labels, luminescent labels, mass labels, light scattering labels, electrochemical labels (e.g., carrying large charge groups), metal labels, and the like. Exemplars of such labeling groups are disclosed by U.S. Pat. Nos. 7,332,284 and U.S. Patent Publication Nos. 2009/0233302 filed Mar. 12, 2009, 2008/0241866 filed Mar. 27, 2008, and 2010/0167299 filed Nov. 17, 2009, the contents of which patents and applications are incorporated herein for all purposes by this reference.

In various embodiments, one or more reactants in an analysis is provided with a fluorescent labeling group that possesses a fluorescent emission spectrum that is shifted from its excitation spectrum, allowing discrimination between the excitation light source and the emission of the label group. These fluorescent labels typically have high quantum yields, further enhancing their detectability. A variety of different fluorescent label groups are well known in the art, and include fluorescein and rhodamine based organic dyes, such as those sold under the Cy3 and Cy5 labels from, e.g., GE Healthcare, and the AlexaFluor® dyes available from Life Technologies, Inc. A wide variety of organic dye structures have been previously described in the art.

Other fluorescent label groups include, for example, particle-based labeling groups. Some such particle label groups constitute encapsulated or otherwise entrained organic fluorophores, while others comprise fluorescent nanoparticles, such as inorganic semiconductor nanocrystals, e.g., as described in U.S. Pat. Nos. 6,207,392, 6,225,198, 6,251,303, 6,501,091, and 7,566,476, the full disclosures of which are incorporated herein by reference in their entirety for all purposes.

By detecting these fluorescent labeling groups, one can ascertain the localization of a given labeled reactant, or detect reaction events that result in changes in the spectral or other aspects of the fluorescently labeled reactant. For example, in binding or hybridization reactions, the ability of a labeled reactant to bind to another immobilized reactant is detected by contacting the reactants, washing unbound labeled reactant away, and observing the immobilized reactant to look for the presence of bound fluorescent label. Such assays are routinely employed in hybridization assays, antibody assays, and a variety of other analyses.

In a number of different nucleic acid sequencing analyses, fluorescently labeled nucleotides are used to monitor the polymerase-mediated, template-dependent incorporation of nucleotides in a primer extension reaction. In particular, a labeled nucleotide is introduced to a primer template polymerase complex, and incorporation of the labeled nucleotide is detected. If a labeled nucleotide is incorporated, it is indicative of the underlying and complementary nucleotide in the sequence of the template molecule. In traditional Sanger sequencing processes, the detection of incorporation of labeled nucleotides utilizes a termination reaction where the labeled nucleotides carry a terminating group that blocks further extension of the primer. By mixing the labeled terminated nucleotides with unlabeled native nucleotides, one generates nested sets of fragments that terminate at different nucleotides. These fragments are then separated by capillary electrophoresis, to separate those fragments that differ by a single nucleotide, and the labels for the fragments are read in order of increasing fragment size to provide the sequence (as provided by the last added, labeled terminated nucleotide). By providing a different fluorescent label on each of the types of nucleotides that are added, one can readily differentiate the different nucleotides in the sequence (e.g., U.S. Pat. No. 5,821,058, incorporated herein for all purposes by this reference).

In newer generation sequencing technologies, arrays of primer-template complexes are immobilized on surfaces of substrates such that individual molecules or individual and homogeneous groups of molecules are spatially discrete from other individual molecules or groups of molecules, respectively. Labeled nucleotides are added in a manner that results in a single nucleotide being added to each individual molecule or group of molecules. Following the addition of the nucleotide, the labeled addition is detected and identified.

In some cases, the processes utilize the addition of a single type of nucleotide at a time, followed by a washing step. The labeled nucleotides that are added are then detected, their labels removed, and the process repeated with a different nucleotide type. Sequences of individual template sequences are determined by the order of appearance of the labels at given locations on the substrate.

In other similar cases, the immobilized complexes are contacted with all four types of labeled nucleotides where each type bears a distinguishable fluorescent label and a terminator group that prevents the addition of more than one nucleotide in a given step. Following the single incorporation in each individual template sequence (or group of template sequences,) the unbound nucleotides are washed away, and the immobilized complexes are scanned to identify which nucleotide was added at each location. Repeating the process yields sequence information of each of the template sequences. In other cases, more than four types of labeled nucleotides are utilized.

In particularly elegant approaches, labeled nucleotides are detected during the incorporation process, in real time, by individual molecular complexes. Such methods are described, for example, in U.S. Pat. No. 7,056,661, which is incorporated herein by reference in its entirety for all purposes. In these processes, nucleotides are labeled on a terminal phosphate group that is released during the incorporation process, so as to avoid accumulation of label on the extension product, and avoid any need for label removal processes that can be deleterious to the complexes. Primer/template polymerase complexes are observed during the polymerization process, and nucleotides being added are detected by virtue of their associated labels. In one particular aspect, they are observed using an optically confined structure, such as a zero mode waveguide (See, e.g., U.S. Pat. No. 6,917,726, which is incorporated herein by reference in its entirety for all purposes) that limits exposure of the excitation radiation to the volume immediately surrounding an individual complex. As a result, only labeled nucleotides that are in the process of being incorporated are exposed to excitation illumination for a time that is sufficient to identify the nucleotide. In another approach, the label on the nucleotide is configured to interact with a complementary group on or near the complex, e.g., attached to the polymerase, where the interaction provides a unique signal. For example, a polymerase may be provided with a donor fluorophore that is excited at a first wavelength and emits at a second wavelength, while the nucleotide to be added is labeled with a fluorophore that is excited at the second wavelength, but emits at a third wavelength (See, e.g., U.S. Pat. No. 7,056,661, previously incorporated herein). As a result, when the nucleotide and polymerase are sufficiently proximal to each other to permit energy transfer from the donor fluorophore to the label on the nucleotide, a distinctive signal is produced. Again, in these cases, the various types of nucleotides are provided with distinctive fluorescent labels that permit their identification by the spectral or other fluorescent signature of their labels.

As will be appreciated, a wide variety of analytical operations may be performed using the overall reaction framework described herein, and as a result, are applicable to the present invention. Such reactions include reactive assays, e.g., examining the combination of reactants to monitor the rate of production of a product or consumption of a reagent, such as enzyme reactions, catalyst reactions, etc. Likewise, associative or binding reactions may be monitored, where one is looking for specific association between two or more reactants, such as nucleic acid hybridization assays, antibody/antigen assays, coupling or cleavage assays, and the like.

II. Analytical Device

The analytical system in accordance with the present invention employs one or more analytical devices referred to as "optode" elements. In an exemplary embodiment, the system includes an array of analytical devices formed as a single integrated device. An exemplar of a suitable optode element is disclosed by U.S. Provisional Application No. 61/306,235 filed on Feb. 19, 2010, and entitled Integrated Analytical Devices and Systems (the '235 application), the entire contents of which are incorporated herein for all purposes by this reference. The exemplary array is configured for single use as a consumable. In various embodiments, the optode element includes other components including, but not limited to local fluidics, electrical connections, a power source, illumination elements, a detector, logic, and a processing circuit. Each analytical device or array is configured for performing an analytical operation as described above.

While the components of each device and the configuration of the devices in the system may vary, each analytical device typically comprises the general structure shown as a block diagram in FIG. 1. As shown, an analytical device 100 typically includes a reaction cell 102, in which the reactants are disposed and from which the optical signals emanate. "Reaction cell" is to be understood as generally used in the analytical and chemical arts and refers to the location where the reaction of interest is occurring. Thus, "reaction cell" may include a fully self-contained reaction well, vessel, flow cell, chamber, or the like, e.g., enclosed by one or more structural barriers, walls, lids, etc., or it may comprise a particular region on a substrate and/or within a given reaction well, vessel, flow cell or the like, e.g., without structural confinement or containment between adjacent reaction cells. The reaction cell may include structural elements to enhance the reaction or its analysis, such as optical confinement structures, nanowells, posts, surface treatments, such as hydrophobic or hydrophilic regions, binding regions, or the like.

In various respects, "analytical device" refers to a reaction cell and associated components that are functionally connected. In various respects, "analytical system" refers to one more associated analytical devices and associated components. In various respects, "analytical system" refers to the larger system including the analytical system and other instruments for performing an analysis operation.

In some cases, one or more reactants for the reaction of interest may be immobilized, entrained or otherwise localized within a given reaction cell. A wide variety of techniques are available for localization and/or immobilization of reactants, including surface immobilization through covalent or non-covalent attachment, bead or particle based immobilization, followed by localization of the bead or particle, entrainment in a matrix at a given location, and the like. Reaction cells may include ensembles of molecules, such as solutions, or patches of molecules, or it may include individual molecular reaction complexes, e.g., one molecule of each molecule involved in the reaction of interest as a complex. Similarly, the overall devices and systems of the invention may include individual reaction cells or may comprise collections, arrays or other groupings of reaction cells in an integrated structure, e.g., a multiwall or multi-cell plate, chip, substrate or system. Some examples of such arrayed reaction cells include nucleic acid array chips, e.g., GeneChip® arrays (Affymetrix, Inc.), zero mode waveguide arrays (as described elsewhere herein), microwell and nanowell plates, multichannel microfluidic devices, e.g., LabChip® devices (Caliper Life Sciences, Inc.), and any of a variety of other reaction cells. In various respects, the "reaction cell", sequencing layer, and zero mode waveguides are similar to those described in U.S. Pat. No. 7,486,865 to Foquet et al., the entire contents of which are incorporated herein for all purposes by this reference.

Although the exemplary analytical device includes an array of analytical devices having a single waveguide layer and reaction cell layer, one will appreciate that a wide variety of layer compositions may be employed in the waveguide array substrate and cladding/reaction cell layer and still achieve the goals of the invention (see, e.g., published U.S. Patent Application No. 2008-0128627, incorporated herein for all purposes by this reference).

The analysis system typically includes one or more analytical devices 100 having a detector element 120, which is disposed in optical communication with the reaction cell 102. Optical communication between the reaction cell 102 and the detector element 120 may be provided by an optical train 104 comprised of one or more optical elements generally designated 106, 108, 110 and 112 for efficiently directing the signal from the reaction cell 102 to the detector 120. These optical elements may generally comprise any number of elements, such as lenses, filters, gratings, mirrors, prisms, refractive material, or the like, or various combinations of these, depending upon the specifics of the application.

In various embodiments, the reaction cell 102 and detector 120 are provided along with one or more optical elements in an integrated device structure. By integrating these elements into a single device architecture, one improves the efficiency of the optical coupling between the reaction cell and the detector. In particular, in conventional optical analysis systems, discrete reaction vessels are typically placed into optical instruments that utilize free-space optics to convey the optical signals to and from the reaction vessel and to the detector. These free space optics tend to include higher mass and volume components, and have free space interfaces that contribute to a number of weaknesses for such systems. For example, such systems have a propensity for greater losses given the introduction of unwanted leakage paths from these higher mass components, and typically introduce higher levels of auto-fluorescence, all of which reduce the signal to noise ratio (SNR) of the system and reduce its overall sensitivity, which, in turn can impact the speed and throughput of the system. Additionally, in multiplexed applications, signals from multiple reaction regions (i.e., multiple reaction cells, or multiple reaction locations within individual cells), are typically passed through a common optical train, or common portions of an optical train, using the full volume of the optical elements in that train to be imaged onto the detector plane. As a result, the presence of optical aberrations in these optical components, such as diffraction, scattering, astigmatism, and coma, degrade the signal in both amplitude and across the field of view, resulting in greater noise contributions and cross talk among detected signals.

The devices of the invention, in contrast, include relatively low volumes between the reaction cell and the detector, thereby reducing the noise contributions from those components, and provide few or no free space regions between optical components that can contribute to losses and necessitate the use of small numerical aperture detection. Further, in preferred aspects, a given reaction region is provided with its own devoted optical train to direct signals to a devoted portion of the sensor.

In various embodiments, the device is configured such that emitted light from the fluorescent species in the nanoscale well is transmitted through a solid medium (e.g., a substantially solid medium), and not transmitted through only free space (e.g., an air gap) on its way to the detector. A substantially solid medium includes a medium with regions of both solid medium and air. In an exemplary embodiment, the substantially solid medium is a multilayered dielectric including one or more solid layers and, optionally, one or more air layers. The substantially solid medium is generally transparent to the emitted fluorescent light. The solid medium can comprise inorganic or organic materials, comprising, for example a metal oxide, glass, silicon dioxide, or transpiring polymeric materials. While generally transmitting the emitted fluorescent light, the optical layer between the nanoscale well and the detector can also be configured to act as a filter to other portions of the electromagnetic spectrum. For example, the optical layer can comprise one or more filter layers that block or reflect unwanted portions of the spectrum. Such filters can comprise dichroic filters or dielectric stacks comprising layers of materials having different refractive indices. In some cases, these dichroic filters can have thin layers comprising air in order, for example to provide a low refractive index layer. While the optical layer may comprise a thin layer comprising air, it is to be understood that the material having one or more of such regions is still a substantially solid medium, and that such a thin layer or series of layers would not constitute the use of free space optics. The thin layer comprising air has a thickness that is generally greater than about 0.1 micron, 0.2 micron, 0.5 micron or 1 micron. The thin layer comprising air has a thickness that is generally less than about 100 micron, 50 micron, 20 micron or 10 micron. The thin layer comprising air has a thickness that is generally from about 0.1 micron to about 100 micron, between 0.5 micron and 50 micron, or between about 1 micron and 10 micron.

As a result, optical aberrations are confined to individual reaction regions, as opposed to being applied across an entire array of reaction regions. Likewise, in a further preferred aspect, the reaction region, optical train, and detector, are fabricated in an integrated process, e.g., micromechanical lithographic fabrication processes, so that the components are, by virtue of the manufacturing process, pre-aligned and locked in to such alignment by virtue of the fabrication process. Such alignment is increasingly difficult using free space optics systems as reaction region sizes decrease and multiplex increases. In addition, by integrating such components into one unified component, relative movement between such subcomponents, as is the case with free space optics, can make drift and continued alignment resulting from vibrations, a more difficult task. Likewise, the potential for contamination in any of the intermediate spaces (e.g., dust and/or other contaminants) is eliminated or at least substantially reduced in an integrated system, as compared to free space systems.

In addition to reducing noise contributions from the optical pathway, the integrated devices of the invention also benefit from fabrication processes and technology that eliminate other issues associated with discrete reaction cell, optic, and detection components. For example, with respect to certain highly multiplexed or arrayed reaction cells, initial alignment and maintaining alignment of the detection with the reaction cell over the full length of the analysis can raise difficulties. This is particularly the case where excitation illumination may be specifically targeted among different array locations of the reaction cell and/or among different reaction cells.

In the embodiment shown in FIG. 1, a signal source, a transmission layer comprising optical components to modulate the light transmitted therethrough, and a detector are joined together into an integrated device.

As used herein, the term "integrated" may have different meanings when used to refer to different aspects of the invention. For example, in the case of an integrated optical device or an integrated optical system, the term integrated generally means that the various components are physically connected, and that the optical signals pass from component to component through solid media. The optical signals generally travel without passing into significant regions of air or free space, as would be understood by one in the field of optics. The integrated optical system may have regions comprising thin films comprising air, for example in the context of a dielectric stack or dielectric filter as described herein. In the context of the description of a system, the term "integrated" is to be understood as generally used in the analytical and electrical engineering fields, where "integrated" would refer, for example, to a combination or coordination of otherwise different elements to provide a harmonious and interrelated whole, whether physically or functionally. The meaning of the term will generally be understood by one of skill in the art by the context in which it is used.

Being an integrated device, the light emitted from the reactor cell 102 will pass through to the detector through a solid medium. In some embodiments, the integrated analytical device also comprises components for providing illumination to the reactor cell 102. For example, in many cases where reactor cell 102 comprises a zero mode waveguide, it is often desirable to provide illumination from below the reactor cell, for example between the bottom of reactor cell 102 and the transmission layer or optical train 104. In some cases, a waveguide structure is incorporated into the analytical device to provide such illumination. Analytical devices comprising waveguides for illumination are described in more detail herein, and for example, in U.S. patent application Ser. No. 11/849,157 filed Aug. 31, 2007 and 12/560,308 filed Sep. 15, 2009, which are incorporated herein by reference for all purposes.

In various embodiments, the analytical device is a substrate including a reaction cell array, and a detector array on a bottom surface of the array. The device may also include other components such as processing circuits, optical guides, and processing circuits. In various embodiments, the analytical device may be formed by building layers on a substrate or by bonding two or more substrates. In an exemplary device, a fused silicon (FuSi) substrate, a ZMW layer, and a silicon substrate with a photodetector array are bonded together to form the array of analytical devices. One will appreciate that such integrated analytical devices have significant advantages in terms of alignment and light collection. For example, the reaction site and detector are aligned through the manufacturing process. One will appreciate from the description herein, that any of the components and systems may be integrated or modified in various manner. In another example, the ZMW substrate and detector array are on separate substrates that are brought together for the experiment, after which the ZMW substrate is replaced with another substrate for a second experiment. With this approach, the detector array may be re-used rather than being disposed with the ZMW substrate after an experiment. It may also be more cost effective as the yields from each of the processes are separated. In this manner, the ZMW array and detector array are in intimate contact during the experiment (as if they are part of an integrated device), but they can be separated after the measurement.

Figure 1B:
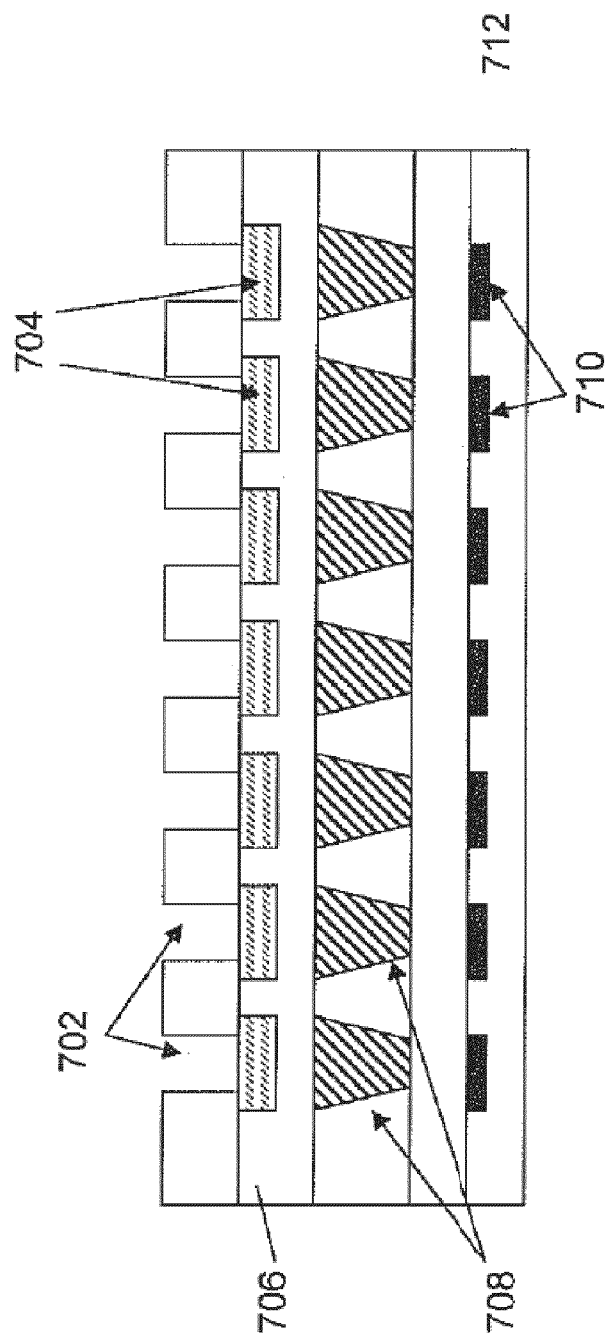
FIG. 1B schematically illustrates an end view of an integrated optical analysis device, including waveguide illumination.
Figure 1C:
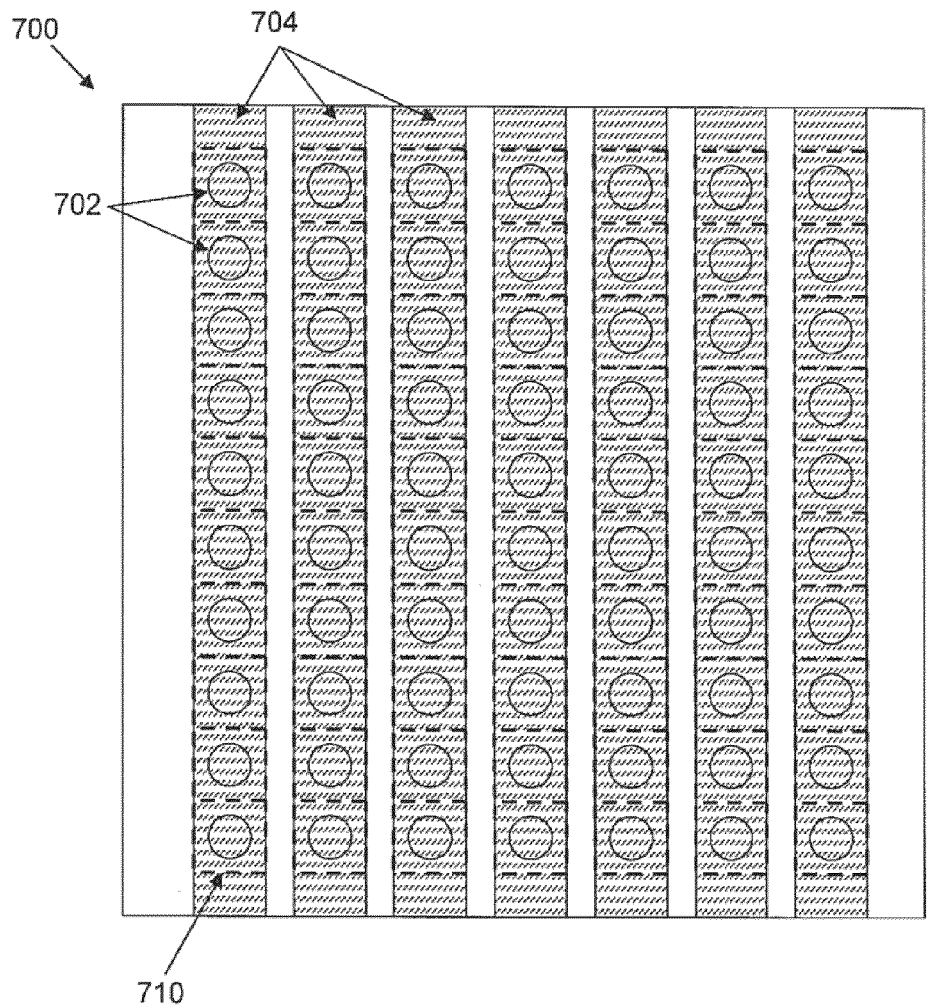
FIG. 1C illustrates the major components of the integrated device illustrated in FIG. 1B, from a top view.

An example of a device that includes integrated reaction cell, sensor and optical components including an illumination conduit is shown in FIGS. 1B and 1C. As shown in FIG. 1B, the integrated device 700, shown from an end view, includes a plurality of reaction cells 702. Each reaction cell 702 is in optical communication with an optical conduit or waveguide 706, that is disposed in a waveguide array substrate layer 704 which delivers excitation illumination to the reaction cell. Optical signals emitted from the reaction cell are then conveyed from the reaction cell 702, through the waveguide array substrate 704, to be captured and relayed by integrated optical elements, e.g., optical tunnels 708, to deliver the signals to the sensor elements 710 of sensor array 712. A top down view is shown in FIG. 1C which schematically illustrates the separate waveguides 704, the separate reaction cells 702, and the separate sensor elements 710 on the detector array 712 (not shown). Illumination is delivered through one end of the waveguides 704 and is propagated along the length. Because the reaction cells are defined in a substrate layer overlaid onto the waveguide array substrate 706, that substrate layer operates as a cladding layer everywhere but where the reaction cells are defined. For example, in the case of a metal clad zero mode waveguide array, the reaction cells are defined in a metal layer that forms an upper cladding to the waveguides in the waveguide array substrate 706. At the location where the reaction cells are defined, the cladding is not present, allowing evanescent illumination of the reaction cell from the underlying waveguide 704. As will be appreciated, a wide variety of layer compositions may be employed in the waveguide array substrate and cladding/reaction cell layer, and still achieve the goals of the invention (see, e.g., published U.S. Patent Application No. 2008-0128627, previously incorporated herein). In some cases, the cladding for the zero mode waveguides is not a metal, but is a material having a refractive index that is lower than the index of refraction of the transparent layer below it. The refractive index of the cladding is generally chosen such that there will be total internal reflectance of the incoming illumination. The refractive index difference between the cladding and the transparent layer below the cladding will depend on factors such as the wavelength of light that is used for illumination and the angle at which the illumination light strikes the surface between the cladding and the transparent layer. Where the angle of incidence of the illumination light is shallow, the refractive index difference required for total internal reflection can be smaller. Selection of the appropriate refractive index difference for total internal reflection is well known in the art. Where a material having a lower refractive index is used as a cladding, it can be useful to have the refractive index of a fluid within the zero mode waveguide be close to the refractive index of the cladding in order to minimize any scattering from the zero mode waveguide structure. In some cases, the refractive index of the fluid is substantially the same as the refractive index of the cladding. In some cases the difference in refractive index is less than 0.001, or less than 0.0001. In some cases the difference in refractive index is between 0.01 and 0.00001.

The size of the processing circuits in each of the analytical devices may be minimized to reduce costs. By developing a board in the receiver camera electronics (e.g. massively parallel DSP or microprocessor or a dedicated FPGA, CPLD or ASIC), overall operating costs (i.e. $/mega-base) may be minimized.

Figure 2A:
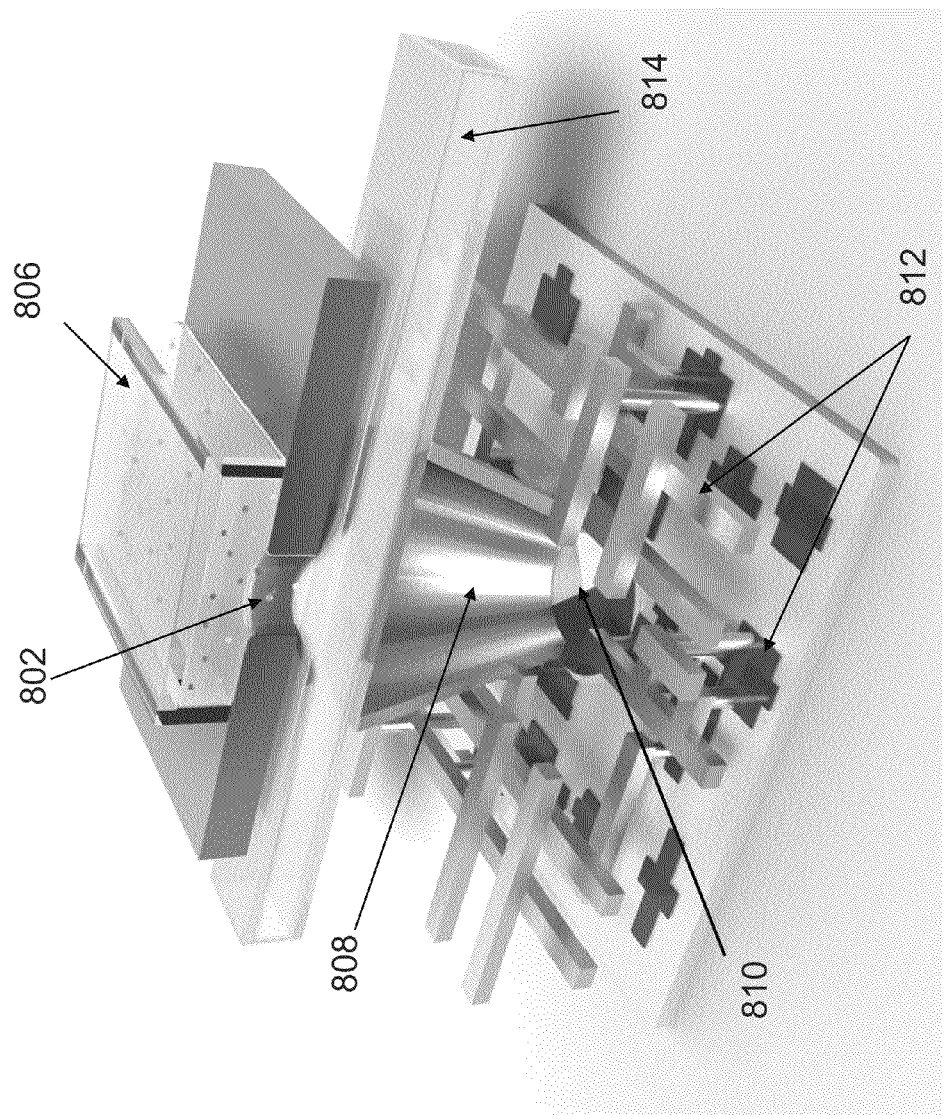
FIGS. 2A and 2B are schematic illustrations of an integrated analytical device (optode) of the invention.

Another embodiment of an integrated analytical device of the invention (optode) is shown in FIG. 2A. While FIG. 2A is shown in open form to illustrate the various components, it is to be understood that analytical device of FIG. 2A represents a structure that comprises all solid or liquid components, and that there is no substantial open or free space between the components.

Figure 2B:
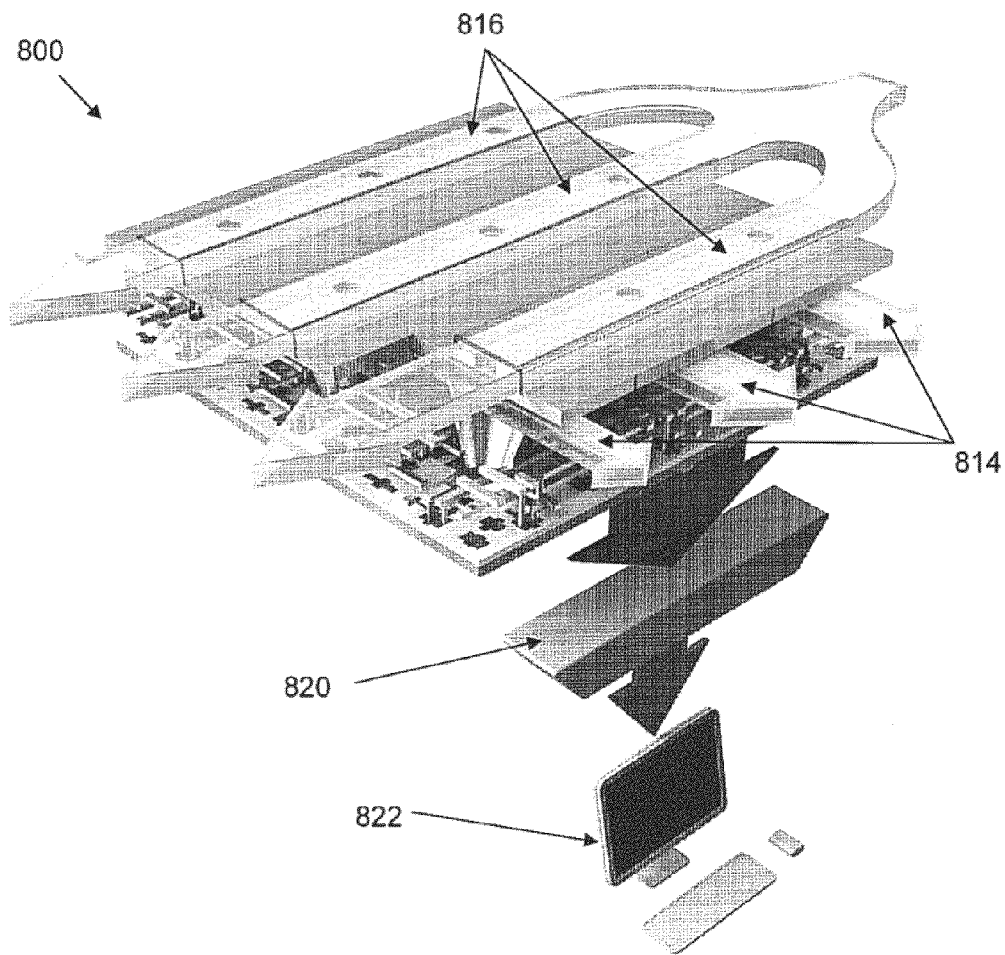

An additional illustration of a device and system integration as described herein is shown in FIGS. 2A and 2B. As shown in FIG. 2A, the analytical device has a reaction cell 802 that is coupled with a reagent reservoir or fluid conduit 806 which delivers reactants to the reaction cell 802. The reaction cell can be a nanoscale well or zero mode waveguide. In some cases, the reaction cell will have a biomolecule such as a polymerase enzyme immobilized within it. The fluidic conduit can provide reagents across a number of reaction cells. Below the reaction cell is a waveguide for providing excitation illumination to the reagents within the reaction cell. While a waveguide is shown here, other optical elements such as those provided elsewhere herein can be used to provide light from under the reaction cell. The illumination light can be used to excite fluorescent emission from reagents with the reactor cell. The light emitted from the reaction cell is directed downward through a transmission layer, which acts to transmit the light from the reaction cell to the detector. In some cases, the transmission layer will have optical components to enhance the efficiency of the light transfer or modulate the light. In the analytical device of FIG. 2A, an optical tunnel or conduit 808 is disposed in optical communication with the reaction cell 802, which is in turn in optical communication with sensing element(s) 810 in the detector, shown as a multicolor discriminating set of sensor elements. The sensor elements are coupled to appropriate electronic components, such as busses and interconnects 812, that make up the overall sensor or camera. Also shown is a waveguide 814 for delivery of excitation illumination to reaction cell 802. FIG. 8B shows a larger view of a multiplexed device including multiple reaction cells and associated components, such as arrayed waveguides 814. Also shown are fluidic conduits 816 also integrated into the device and disposed in fluid communication with the various reaction cells. The overall device 800 is shown schematically coupled to a processor 820 and a computer 822. In some cases, the detector has multiple sensing elements, each for detecting light having a different color spectrum. For example, in the case of sequencing, the sensor for each reaction cell can have 4 elements, one for each of the four bases. In some cases the sensor elements provide color discrimination, in other cases, color filters are used to direct the appropriate color of light to the appropriate sensor element shown as a multicolor discriminating set of sensor elements in FIG. 2A. The sensor elements are coupled to appropriate electronic components 812, such as busses and interconnects, that make up the overall sensor or camera. The electronic components can also include processing elements for processing the signal from the detectors.

III. Optode Arrays and Packaging

The integrated analytical devices of the invention are generally fabricated into arrays of devices, allowing for simultaneously observing thousands to millions of analytical reactions at one time. These arrays of optodes generally require the input of fluids to provide reagents and the conditions necessary for carrying out analytical reactions, the input of excitation light for the measurement of fluorescence, and connections for the output of signal data from the detectors. The invention provides devices, systems, and methods for packaging the optode arrays for these inputs and outputs.

Figure 3:
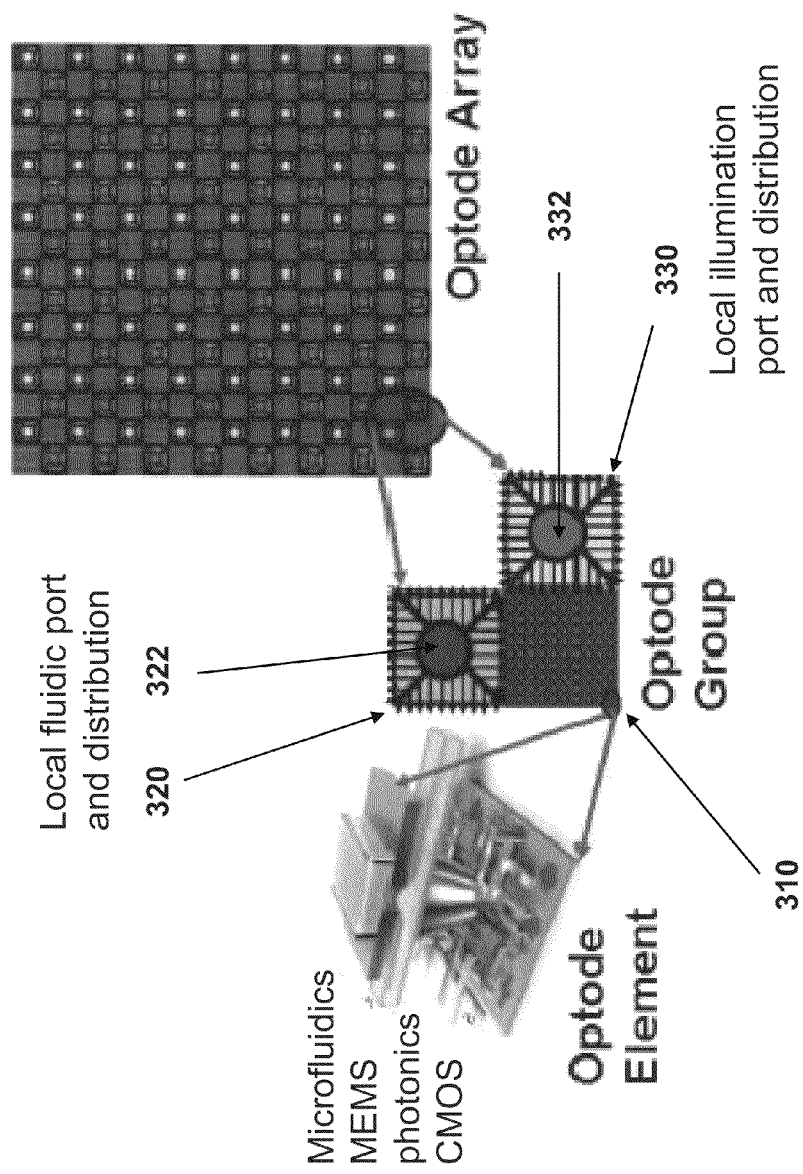
FIG. 3 is a schematic illustration of integration of an integrated analytical device (optode) into an optode array chip in accordance with the present invention.

FIG. 3 provides an embodiment for providing an array of optode elements into an optode array group and an optode array chip, which facilitate the input of light and fluid and the electronic output of data. The optode array chip can be introduced into an instrument or system that is configured with the required input and output connections. For example, in some cases the light and fluid can be introduced from above through input ports on the top of the chip, and electronic data can be extracted from below the chip from electronic contacts on the bottom of the chip. The optode array group comprises an optode array component 310, a fluidic input component 320, and an illumination input component 330. In the embodiment shown in FIG. 3, the fluidic input component 320 and illumination input component 330 are attached to the optode array component at the edges.

The exemplary optode array component 310 comprises an array of optode elements. The number of optodes in the array can be set by the characteristics of the analytical reaction to be measured. The number of optode elements in an optode array component can be from about 10 to about a million or more. In some cases the number of optode elements is from about 100 to about 100,000. As shown in FIG. 3, the fluidic conduit extends over a given optode to the optodes on other sides. As shown in the figure, the exemplary fluidic conduit extends across the optode element in one direction, but essentially not in the perpendicular direction. The fluidic conduits can be fashioned in some cases to extend over multiple optode elements in either or both directions. In some cases, the conduit can deliver fluid to all of the optodes on the optode array component. In some cases, one conduit can deliver fluid to a subset of the optode elements, while other conduits deliver fluid to other optode elements. In some cases, each conduit delivers fluid to a single optode element. Analogously, the waveguides shown for a single optode element in the figure generally extend across multiple optode elements in the array. The waveguides can be channel waveguides extending down a single row of optode elements providing illumination to the reaction cells in that row, or the waveguides can be channel waveguides wider than one row, illuminating more than one row. The waveguides can also be planar waveguides illuminating sections or illuminating all of the reaction cells in the optode array component.

The fluidic input component 320 has a fluid input port 322 for introduction of fluids to the optode array chip. In the embodiment shown in FIG. 3, the fluid input port is accessible from the top. The fluidic input port 322 has a number of fluidic conduits that extend from the input port to the optode array component. The fluidic conduits on the fluidic input port generally mate directly with the fluidic conduits on the optode array component, and both components are generally formed in the same set of process steps. The number of fluidic conduits may depend on the application. In some cases, one fluidic conduit will provide fluid for one row within the reaction cells in the optode array component.

The illumination input component 330 has an illumination input port 332 such as a light pipe for the input of illumination light onto the optode array chip. The illumination input port 332 is connected to a plurality of waveguides that extend from the illumination input port into the waveguides on the optode array. Briefly, waveguides may be provided within the substrate by including higher IR regions to convey light through a lower IR material substrate, where the lower IR material functions as a partial cladding for the waveguide. The waveguide meets the reaction cell with an absence of cladding, allowing evanescent illumination of the reaction cell from the waveguide.

The combination of an optode array component 310, a fluidic input component 320, and an illumination input component 330 as shown in FIG. 3 can be referred to as an optode array group. A plurality of optode array groups can be combined to form an optode array chip. The optode array chip can comprise from 1 to about 100, from about 100 to about 1,000, or more optode array groups. The optode array chip comprising multiple optode array groups can be fabricated using semiconductor and microfabrication processing techniques. For example, an optode array chip containing an array of optode array groups can be fabricated on a wafer, and the wafer can be diced into smaller optode array chips having the appropriate number of optode array groups for a particular application. The optode array chips thus produced will have the fluidic and illumination input ports, and will have electrical contacts extending from the detectors and other electronic elements on the chip for the transfer of data.

Figure 4:
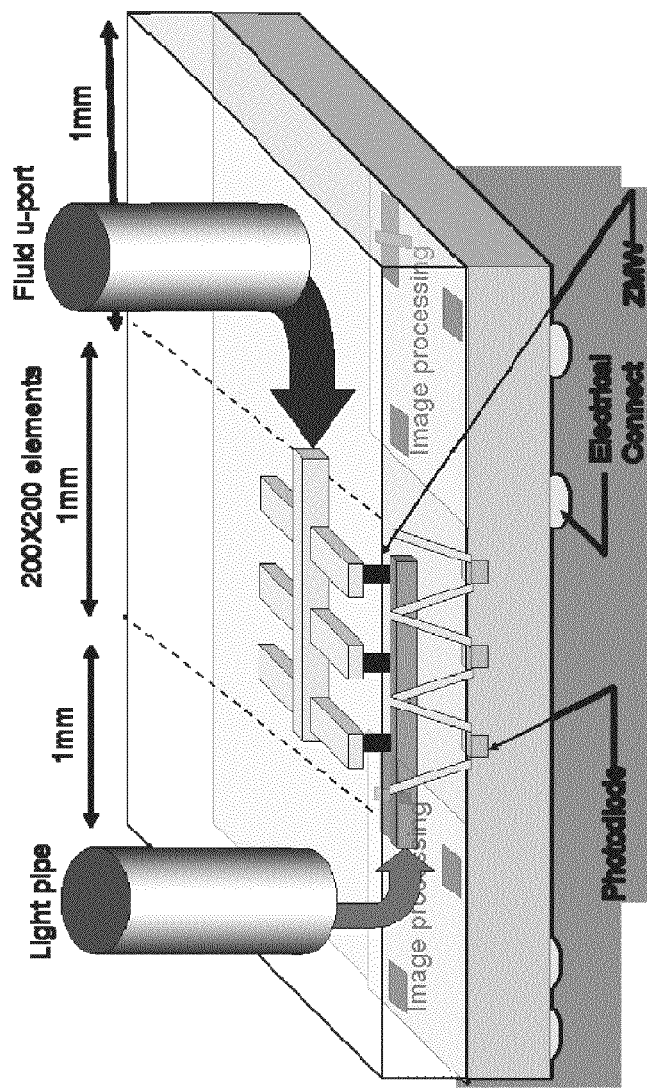
FIG. 4 is a schematic view of a topside connection of fluidic and illumination elements to an integrated analytical device.

FIG. 4 illustrates how an optode array component (middle) having, for example, 200 by 200 optode elements can be supplied with fluid and light from the side. Fluidic port 33c dispenses fluid into an array of fluidic channels that bring the fluid to the reaction cells or ZMWs. Light pipe 53c couples light into channels that transfer the illumination light into the reaction cells from below. Emitted light from the ZMWs is transmitted through a transparent transmission layer down to the detector, in this case a photodiode. The photodiodes detect optical signals and transmit data signals into image processing elements on the chip. Processed signal data is sent to computers for further processing through the electrical contacts on the bottom of the chip. The image processing elements on the chip are useful for processing the date as it comes from the photodetectors. In general, for nucleic acid sequencing, the rate of optical events is relatively low, e.g. on the order of $10^3$ per second. This rate is significantly lower than the typical rate of processing that an the image processing elements are capable of working at, which can be on the order of $10^9$ per second. One approach that can be employed as part of the invention is to have a single image processing element process data from multiple pixels, e.g. from 10 to 1000 pixels. This approach allows for maximum utilization of the image processing elements, e.g. transistors.

In one aspect, the invention comprises a device comprising an array of optode elements wherein each optode element has a reaction cell such as a ZMW or a nanoscale aperture within a cladding layer, the reaction cell configured to receive fluid that contains the reactive species to be analyzed. The analysis generally comprises at least one fluorescently labeled species, the fluorescence from which will provide information about the reaction. Above the reaction cell is a fluidic layer that is in fluid communication with the reaction cell. Below the aperture layer is a waveguide layer that provides illumination to the nanoscale well with evanescent irradiation. The waveguide layer can comprise channel waveguides and/or planar waveguides. Below the waveguide layer is a transmission layer that transmits light emitted from the fluorescent species in the reaction cell to the detector below. Below the transmission layer is a detector layer which receives and detects the emitted light transmitted through the transmission layer, wherein the emitted light is transmitted to the detector without being transmitted through air. In some cases, the detector layer has below it electrical contacts for transmitting data signals out of the chip into computer components for analysis and processing. In some cases processing elements are built into the chip to provide some processing of the signals before sending the data off of the chip.

The array of optode elements is generally provided in one integrated, solid package. In some cases, the portion of the array of optode elements that comprise the detector can be reversibly separated from the portion of the array comprising the reaction cell. This allows for the detector portion to be used over and over again with different arrays of reaction cells.

IV. Measurement Systems Comprising Optode Arrays

The optode array chips comprising optode arrays, inputs for light and fluid, and outputs for electronic transfer of data can be inserted into structures that provide for the analysis reaction. In some cases, the optode array chip can be sandwiched within an assembly that provides physical alignment of the input and output features, and can provide the force required for effective mating of the assembly components. One approach to an assembly is the use of a clamshell assembly. An exemplary system includes an array of analytical devices integrated into a system with a test socket. An exemplary system architecture makes use of automated testing equipment and chip-scale packaging techniques. In various embodiments, the test socket is an automated test equipment (ATE) socket (shown in FIG. 5A). In the exemplary system, the socket is connected to the processing system and other system components such as the electrical system.

In some aspects the invention provides an assembly having a sandwich structure comprising: a top piece comprising inputs for illumination light and fluid; an integrated analysis chip in the middle comprising: an aperture layer comprising a plurality of nanoscale apertures through a cladding layer in fluidic contact with the top of the chip, and a waveguide layer comprising a plurality of waveguides configured to provide illumination light to the nanoscale apertures from below, the waveguide layer having one or more illumination ports on the top surface for providing illumination light to the waveguides; a transmission layer comprising a transparent material for transmitting emitted light from the nanoscale apertures; a detector array layer below the transmission layer having detectors electrically connected to pins extending out the bottom of the chip; and a bottom piece having electrical contacts corresponding to the pins on the bottom of the chip; the assembly configured such that upon closure, the chip is aligned with the top and bottom pieces to allow input of the illumination light and fluid from the top piece and extraction of electrical signals from the bottom piece.

Figure 5:
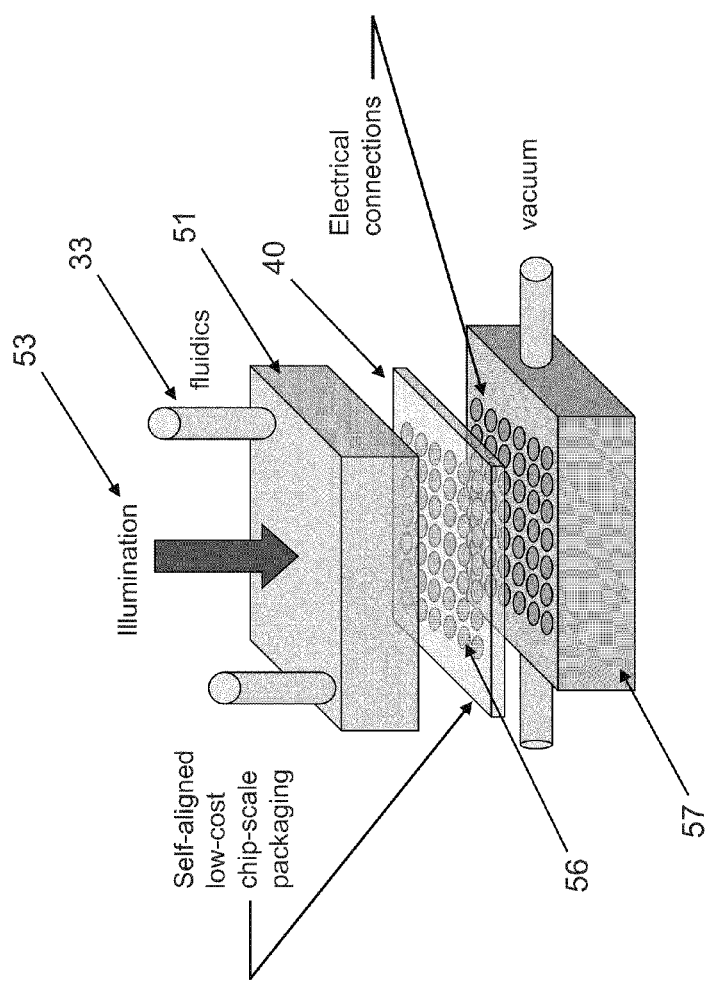
FIG. 5 is a schematic view a test socket and analytical system.
Figure 5A:
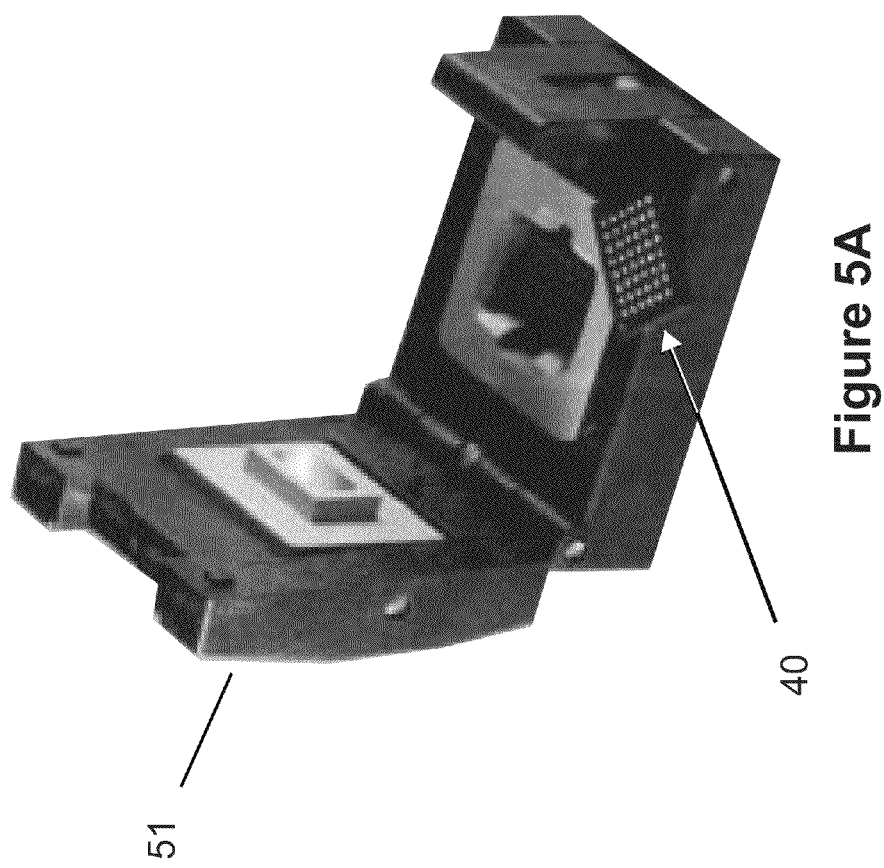
FIG. 5A is a perspective view of an exemplary test socket receiving an exemplary analytical optode chip.

An exemplary integrated device isolates the electrical components from the optical and fluid components, for example, having the optical and fluid delivery on one side and the electrical interconnects on the other side of the device. One embodiment of a system is shown in FIGS. 5 and 5A in which an optode array chip 40 comprising, for example, an array of optode array groups 56, is inserted into a socket comprising a top piece 51 which delivers illumination through an illumination system 53 and fluidics delivery system 33 to the optode array chip, and bottom piece 57 which has an array of electrical contacts which mate with the electrical contacts on optode array chip. In some embodiments the socket can use vacuum to pull the components of the system together to enhance fluidic, illumination, and electrical contacts.

The electrical connections are generally on the bottom surface of the integrated device and optical and fluidic connections on the top side of the device (shown in FIG. 5). The partition of the electrical components in this exemplary manner provides for a two-sided socket that can supply all 110 connections within standard commercial tolerances. As an example, the clamshell socket used in the exemplary commercial ATE may be modified to be used with the analytical array 40. Such test sockets generally have over 50,000 insertion cycle reliability and provide adequate and uniform contact force. Moreover, because the components are integrated into a single device and the socket is self-seating, the optical components and detector are automatically aligned. The exemplary includes spring loaded durable contact pins and oxide scrubbing crowns to further promote auto alignment and reliable contact. Thus, the integrated device can be easily connected to the processing system and other system components by insertion into the socket. This provides higher reliability, lower cost, and generally easier use by the technician.

The reagent handling, sample handling, and illumination functions may be performed in a distributed manner on an area above a processing region of the integrated device and adjacent to the reactor cells (shown, for example, in FIG. 13B). The illumination ports and fluidics ports may be positioned in alternating rows in a checkerboard pattern. These illumination and fluidic ports can service either a single adjacent optode array component 56 or in some cases can service four of the nearest neighboring optode array components. The distribution of illumination and fluids is more uniform, less complex, and performance is maintained to very high multiplex via array segment scalability. Each array segment illumination and fluidics can be individually controlled if desired. In various embodiments, fluidics and photonic connections to socket 51 are made on the top portion of device 40.

Referring to FIG. 5, a sample is provided to the top of the socket and introduced to a set of pipettes that are aligned with the fluidic ports on the optode array. Since the optodes are grouped into sub-arrays, the reduced number of fluidic ports allows for alignment to standard commercial tolerances (e.g. about 0.3 mm) and the reduced number of connections increases reliability. The failure of a single port does not make the entire experiment invalid and the remaining ports can collect data.

Figure 6:
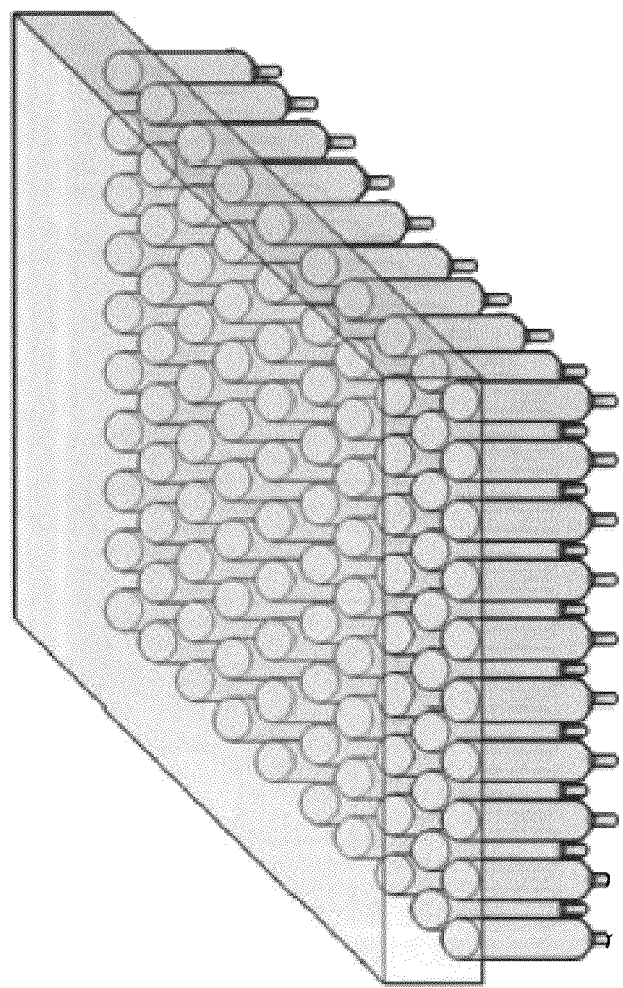
FIG. 6 is a schematic view of a micro-pipette array for delivering reagent to an optode chip array.
Figure 7:
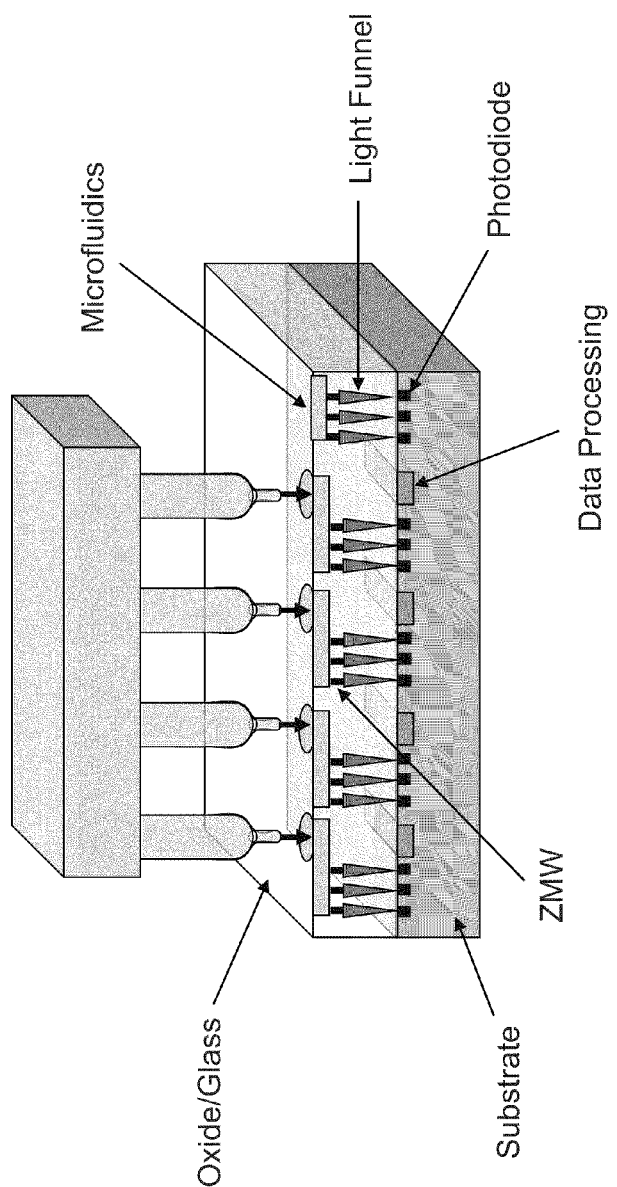
FIG. 7 is a cross-sectional view of the test socket and analytical system illustrating microfluidic connections.

The integrated system of the present invention is typically configured to introduce fluids and optical signals. To provide for a sterile environment to introduce sample and reagent, a low cost fluidic distribution device with single-use capability can be inserted into the socket with each experiment. This fluidic device can be molded with standard bio-compatible polymers similar to multiple micro-pipette systems sold by companies such as Biohit, Thermo and Eppendorf. An example of a disposable 2-D micro-pipette insert for the ATE clamshell socket lid is shown in FIG. 6. FIG. 7 shows a diagram of the introduction of fluids into the optode array chip with an array of micropipettes configured to mate with the fluidic input ports on an optode array chip. The micropipette array 83 mates with fluidic input ports 82 on the optode array chip. The fluid extends down conduits 86 into the optode elements. The ZMWs within the optode elements are illuminated, and emitted light is transmitted through light pipes to the detectors 84. The detectors send signals to data processing components within the chip.

The introduction of fluidics to optode groups may be done with homogenous material, or alternatively, each optode group could be operated with a different sample or reagent setup to perform highly multiplexed assay experiments. The temperature of each fluidic input can also be adjusted or maintained, for example, to provide variability in the assay.

Figure 8:
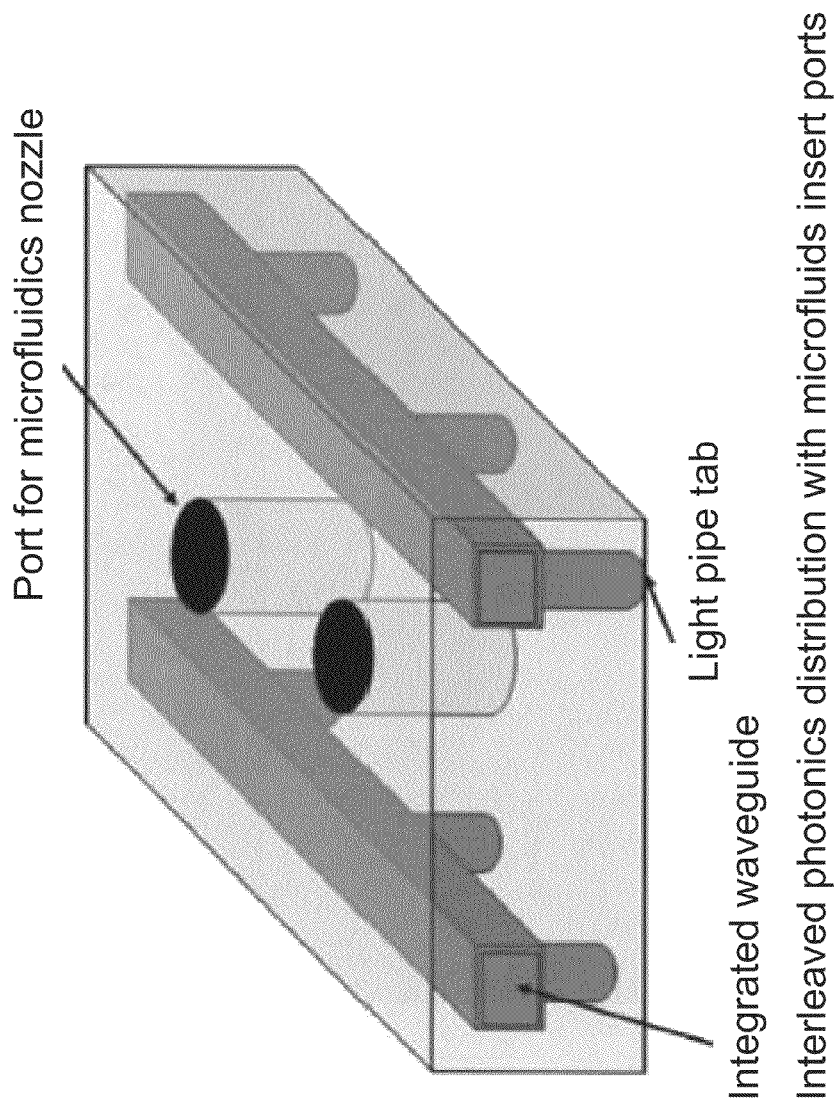
FIG. 8 is a schematic view of a top portion of the test socket illustrating distributed photonics and fluidics system.
Figure 9:
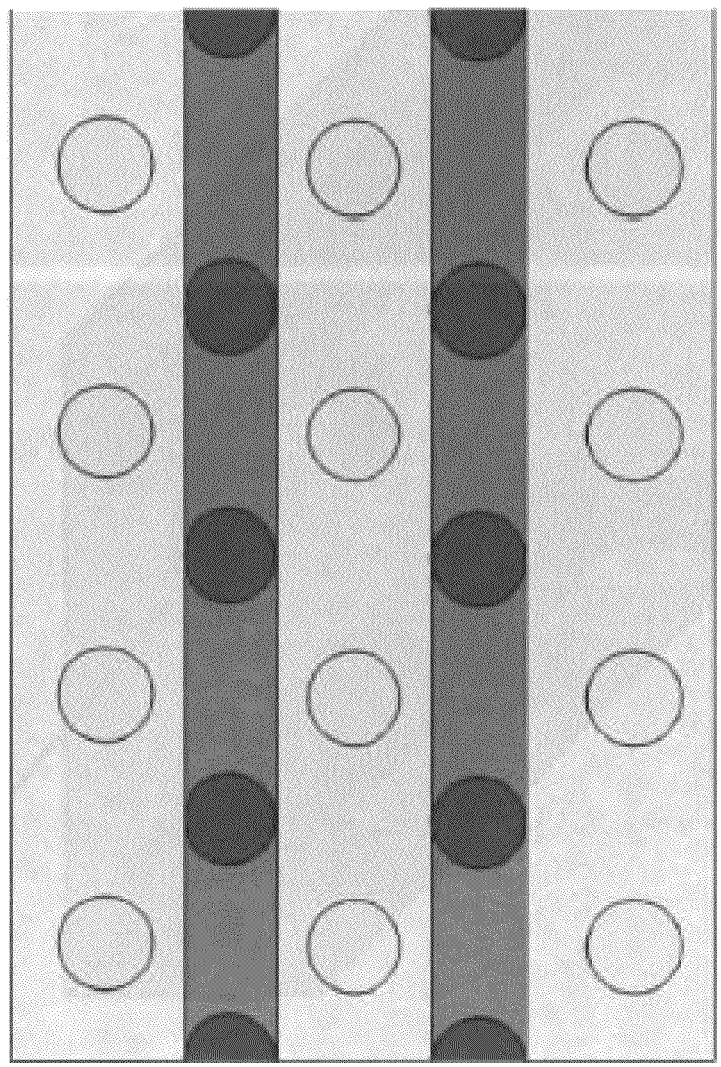
FIG. 9 is a top view of a test socket of FIG. 8.

In various embodiments, the introduction of the photonic illumination signal is accomplished with discrete light ports at the top part of the clamshell socket within commercial tolerances (e.g. between about 0.3 mm to about 0.6 mm). By distributing the light energy in the durable socket to local optode regions, careful design and exotic materials can be used to minimize losses, enable polychromatic excitation and reduce heat load on the active single use device. For example, a lithium niobate waveguide structure can be designed with very low insertion and propagation losses to the optode group. Lower quality distribution networks on the disposable chip are enabled as the transmission distance and branching are significantly reduced. The photonic distribution network can be developed to be interleaved with the microfluidic distribution insert as shown in FIG. 8 and FIG. 9.

Figure 10:
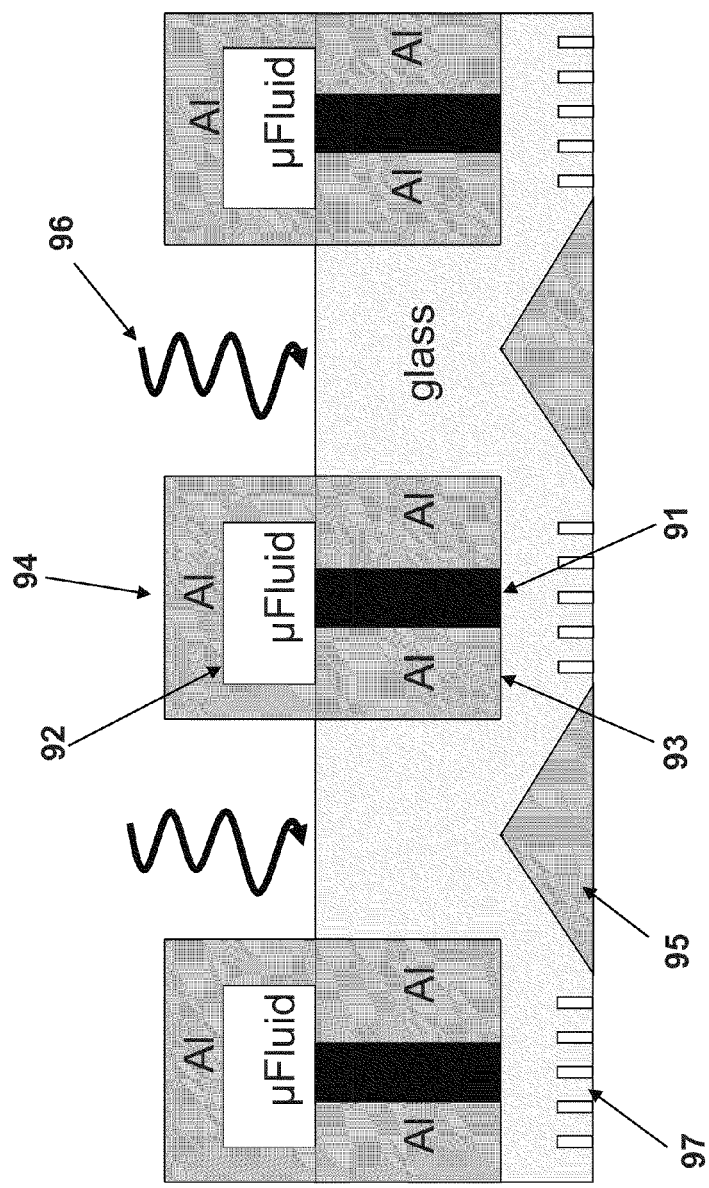
FIG. 10 is a schematic view of an array of reaction cells in a transparent substrate, illustrating an embodiment for providing illumination light to the reaction cells.

In various embodiments, a top-side flood illumination method is used as shown in FIG. 10. The fluidics channels and ZMWs are optically shielded from topside illumination and a path to direct the light to the active area of the ZMWs is provided. The top half of the exemplary ATE socket is transparent to the flood illumination while shielding the microfluidic insert. The socket may be made of a waveguiding material to assist the flood illumination of the part. For example, the socket may include a structure or materials selected to guide the flood illumination along a predetermined path. In FIG. 10 the optode array chip comprises an array of ZMWs 91 formed within a transparent substrate such as glass. Surrounding the ZMWs and extending into the top surface of the glass substrate are regions of opaque cladding material, comprising, for example, a metal such as aluminum. Illumination light 96 introduced from above the chip passes down through the glass and is directed upward to the bottom of the ZMWs by optical elements 95, which can comprise mirrors or dielectric stacks. The light can stimulate emission from sample within the ZMW, the emitted light from which is transmitted down to optical detectors 97. Fluid is transported to the ZMWs by fluid conduits 92. The tops of the ZMWs are covered with an optically opaque covering 94 which prevents the illumination light from entering the ZMW from above. The opaque covering 94 can comprise a metal such as aluminum. In some embodiments, top illumination is carried out with a structure similar to that shown in FIG. 10 wherein each ZMW 91 is illuminated from above, and the optical element 95 includes a reflective structure that is circularly symmetric with respect to the ZMW. A catoptric type arrangement can be used for reflecting the light that enters from above the chip up into the ZMW after reflecting off of a circularly symmetric reflecting element below the ZMW. The catoptric system can have curved surfaces, e.g. parabolic surfaces designed to optimize the amount of light impinging on the ZMW. The center of the catoptric would be non-reflective, allowing light emitted from the ZMW to pass through to one or more photodetectors disposed below the reflective element. The relative size of the opening is chosen to provide the best balance between high intensity illumination, and maximum amount of light collection.

In some aspects, the invention comprises a device for measuring analytical reactions comprising a transparent substrate comprising a plurality of rows of nanoscale apertures extending through an opaque cladding to the top of the transparent substrate. The rows of nanoscale apertures are separated by regions of the transparent substrate open to illumination from above. The device has a plurality of fluidic conduits, each on top of and in fluidic contact with a row of nanoscale apertures. For these exemplary devices each fluidic conduit is coated with an opaque material that prevents the illumination light from entering the nanoscale aperture from above. In addition, the device has a series of features below the nanoscale apertures configured to direct illumination light from above the transparent substrate up into the nanoscale apertures from below. In some embodiments the device also has built-in optical detectors, with at least one detector per nanoscale aperture. In some cases, the device has multiple detectors for each nanoscale well, for example, four detectors, each sensitive to a different color to allow for four color nucleic acid sequencing.

Figure 11:
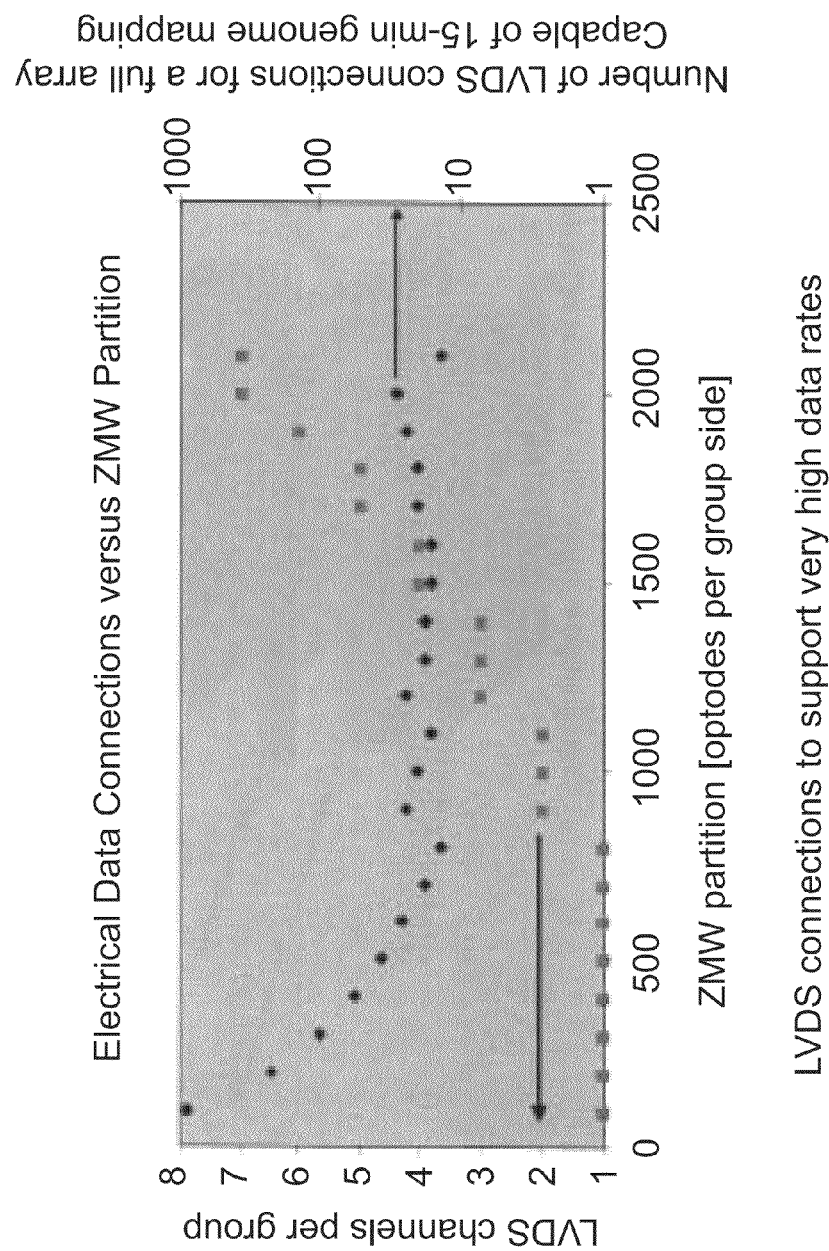
FIG. 11 is an exemplary plot of interleaved electrical data connections versus single molecule waveguides.

In an exemplary system, the development of low cost packaging for analytical arrays is enabled with the use of chip scale packaging techniques. For example, the use of through-hole vias with distributed processing and data collation circuitry enables the multiplexing of many analytical signals onto a greatly reduced number of I/O lines. By example, a collection of 256×256 elements each operating at 25 incorporations per second and providing 5 bytes per event requires an electrical bandwidth of about 65 mega-bits per second. This bandwidth can be provided at only about 10% of the maximum data rate of standard LVDS signaling (ANSI-644) which only needs two connections. For a device capable of mapping an entire genome in 15 minutes, for example, as few as 14 LVDS electrical connections are required as is shown in FIG. 11.

In some embodiments, a plurality of devices are formed in a substrate (e.g. wafer) cut from a sheet material. The wafer can comprise, for example, silicon or fused silica. The exemplary device includes a real-time sensing structure integrated with the chemical reaction cells and provides for the decoupling of the reactor location with the optical elements. The detector elements are grouped around distributed processing cells thereby enabling significant performance advantages with high parallelism. In addition, this architecture reduces the distribution path for fluidics, signal, and stimulus by arranging cells into groups of manageable I/O "pads" corresponding to optode groups.

Figure 12:
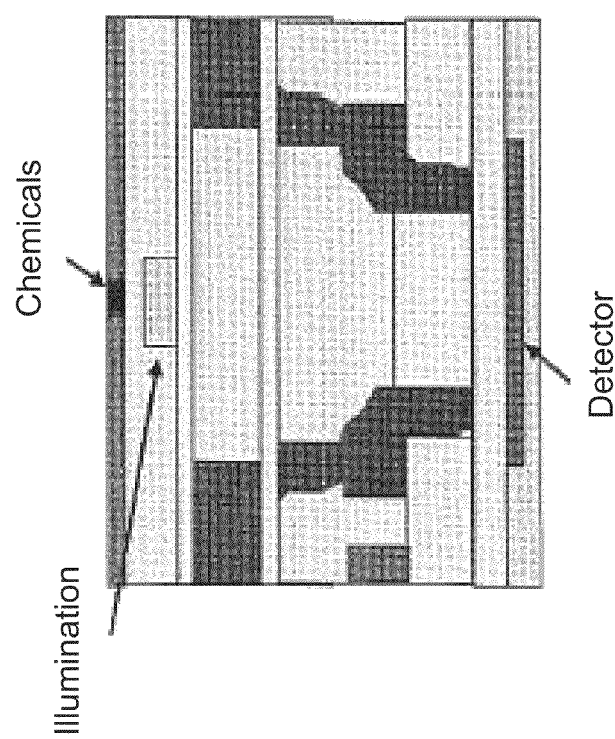
FIG. 12 is a schematic view of an analytical device having directional components defining an optical guide path, the device being formed from layers on a substrate.

The implementation of integrated sensing elements with the cell arrays/reactors provides many benefits including higher speed operation and the ability to extract tagged signals from reduced emissions with synchronized light. FIG. 12 shows another embodiment of an integrated analytical device cell with a fully contained light source, cell reactor element, and detector. By eliminating common and redundant illumination and detection paths, the fidelity of the sensed signal is maintained.

While there are many benefits of a distributed architecture, the distribution branching network required for a high resolution array presents some challenges and limitations. For example, the losses associated with a waveguide operating with many branches and taps will introduce a light intensity gradient across the device. One method of overcoming this problem is with cross-hatched, alternating waveguides. In some cases, the device uses monochromatic illumination and detection techniques to avoid or mitigate such problems.

Turning to FIGS. 13A, 13B, and 13C, an array with distributed functions is shown. FIGS. 13A, 13B, and 13C represent layers within an optode array chip illustrating the various functions performed in different portions of the chip. FIG. 13B shows the topside of an optode array chip having reactor array components 71, illumination input components 72, and fluidic input components 73. FIG. 13A shows the layer in which the optode array components have an array of detectors 70. As illustrated, the detectors are connected to processing components 75. These processing components process the signal from the detectors before sending the signal on for further processing and analysis. FIG. 13C shows the base of the optode array chip. The base has an array of electrical connections. In the embodiment shown, the portions of the chip under the optode array components have contacts for the input of power. The portions of the chip under the fluidic input and illumination input components have electrical contacts for the output of signal from the signal processing elements.

The illustrated array is manufactured using techniques similar to silicon wafer preparation and testing techniques. The array is built up from a substrate with any of the above mentioned analytical elements. The array does not require regular spacing. One will further appreciate that the system architecture can be easily set up and scaled. Each "unit" may be an integrated, local system with a number of optical, detection, and processing elements. The outputs of each of the reactor cell detectors (containing the preprocessed pixel data) is connected to a processing circuit where many functions of various utilities can be performed including, but not limited to, data reduction, digitization, buffer storage, bus arbitration, and the like.

Referring to FIG. 13B, the reagent handling and illumination can be performed in a distributed manner using the area above the processing region and adjacent to each of the respective reactor cells. A checkerboard pattern of alternating rows of illumination ports and fluidics ports is provided. These fluidic and illumination ports can be provided as described above as arrays of optode array groups. These ports can service either the single adjacent reactor array or a plurality of arrays. In various embodiments, each node or set of ports services the neighboring arrays (e.g. arrays on each of the four sides). In contrast to conventional devices, the distribution of illumination and fluids is more uniform and less complex and performance is maintained to very high multiplex via array segment scalability. One will appreciate that each array segment illumination and fluidics can be individually controlled if desired.

Referring to FIG. 13C, the readout of array segments can be performed via local through-hole vias to substrate connections. The packaging and testing of the system can be done with industry accepted and verified processes. To complement the fluidic and illumination connections on the topside of the wafer, a number of electrical connections representing the I/O of the array segments may be made on the bottom of the wafer as discussed above. These connections can be segmented by power and signal groups.

With this top-bottom connection set-up, a standard clamshell packaging technique (e.g. ATE socket) as described above can be used to connect the device to the overall system. Referring to FIG. 4, the topside connections involve the alignment of multiple illumination light pipes 53c and microfluidic nozzles 33c. For example, if a 2000×2000 cell array is needed and 100 array segments are placed in 200×200 multiplex on 5 micrometer centers, the adjacent 100 I/O and processing segments are about 1 mm×1 mm in size. Therefore, 10×5 connections of both illumination and fluidics are needed but have achievable alignment at the pitches described. In a similar fashion, the data reduction performed in the processing regions reduces the number of electrical connections that need to be interfaced to the external circuitry. Standard electrical bump bonds can be used to connect with standard durable electrical sockets with achievable tolerances for high speed operation.

Turning back to FIG. 14, the scalability of the integrated devices is extended to a scalable array segment and very high resolution. In this high resolution array, the performance across the array (periphery versus center) is made more uniform with the herein-described system architecture.

Figure 14:
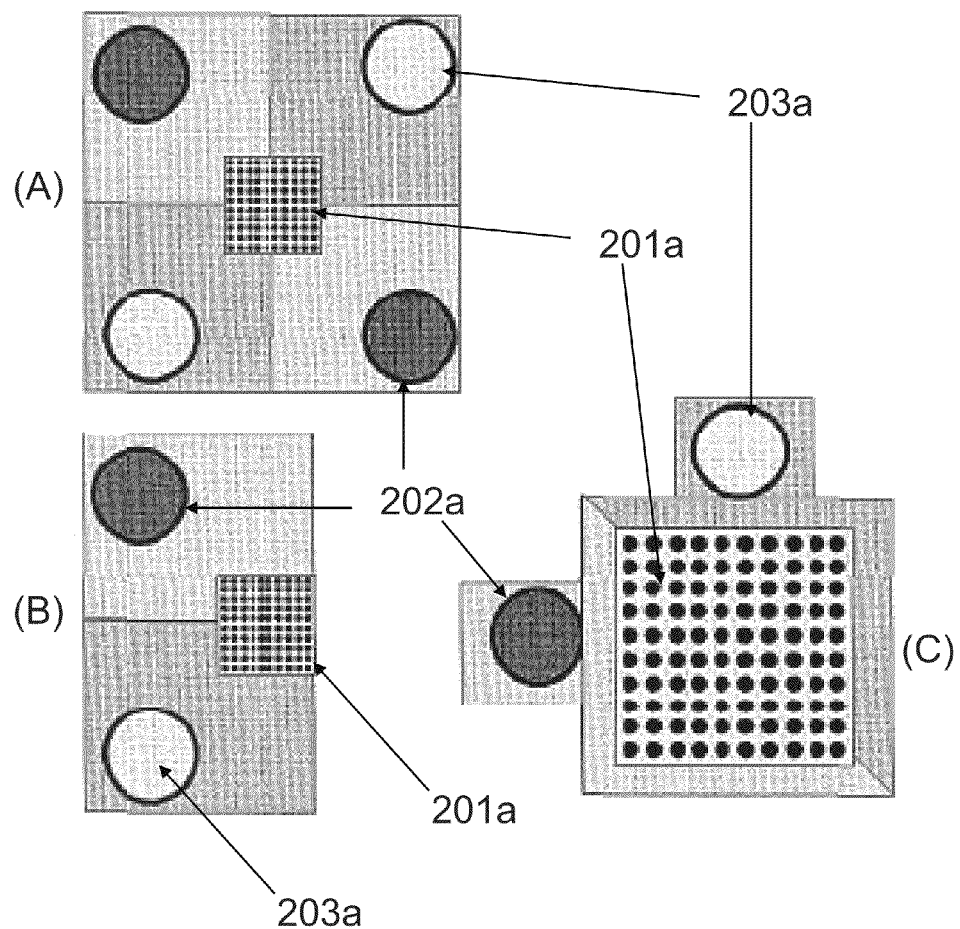
FIG. 14 shows views of various configurations for arrangements of optode array components, fluidic input components, and illumination input components.

One will appreciate that the size and arrangement of the reactor arrays and optodes is relatively flexible. The partition of the reactor array sections and the adjacent distribution and processing regions can be sized across a relatively wide range and each section can be spaced with respect to each other at varying distances to support the overall function required. Exemplary partitions are shown in FIG. 14. In FIG. 14(A) an optode array component 201a is connected to two fluidic input components 202a and two illumination input components 203a. In FIG. 14(B) an optode array 201a component is connected to one fluidic input component 202 and one illumination input component 203a. In FIG. 14(C) an optode array component 201a is connected along one edge to a fluidic input component 202a and along another edge to an illumination input component 203a.

Although in various respects the analytical device is described as being fabricated in a monolithic fashion, such that all integrated elements are fabricated from the outset into the same structure, one will appreciate from the description herein that other manufacturing techniques may be utilized. In some cases, different components are fabricated separately, followed by integration of the separate parts into a single integrated device structure. For example, the sensor elements, optionally including one or more optical elements, may be fabricated in a discrete component part. Likewise, the reaction cells may be fabricated in a discrete component part optionally along with one or more optical components. These two separate parts can then be mated together and coupled into a single integrated device structure where the sensor elements in the first component part are appropriately aligned with the reaction cells in the second component part. In various embodiments, the analytical device employs modular assembly techniques. In this manner, various components can be joined, separated, and reassembled as needed. For example, the reaction cell array and waveguide and sensor may be assembled during an experiment and then separated so the cell array and waveguide can be replaced for set-up of the next experiment.

Joining of two discrete parts may be accomplished by any of a variety of known methods for coupling different components in the semiconductor industry. For example, two planar components may be joined using, e.g., joining through Van Der Waals forces, ultrasonic welding, thermal annealing, electrostatic, vacuum, or use of other joining mechanisms, e.g., epoxide bonding, adhesive bonding, or the like. Appropriate joining techniques include, but are not limited to, mechanical, chemical, and ionic techniques.

As discussed above, in joining separate parts it may be desirable to join such parts that respective functional components align between the parts. For example, where an overall device is intended to have a dedicated sensor element for each reaction cell, it may be necessary to align a part that includes the sensor elements with a part that includes the reaction cells such that they are aligned in optical communication. Alignment may be accomplished through the use of structural alignment elements fabricated onto the component parts as fiducials during fabrication, e.g., pins and holes on opposing surfaces, ridges and grooves, etc. Alternatively, in the fabrication process, different active regions may be provided upon the component parts such that attractive forces are exhibited between regions where alignment is desired.

Figure 13D:
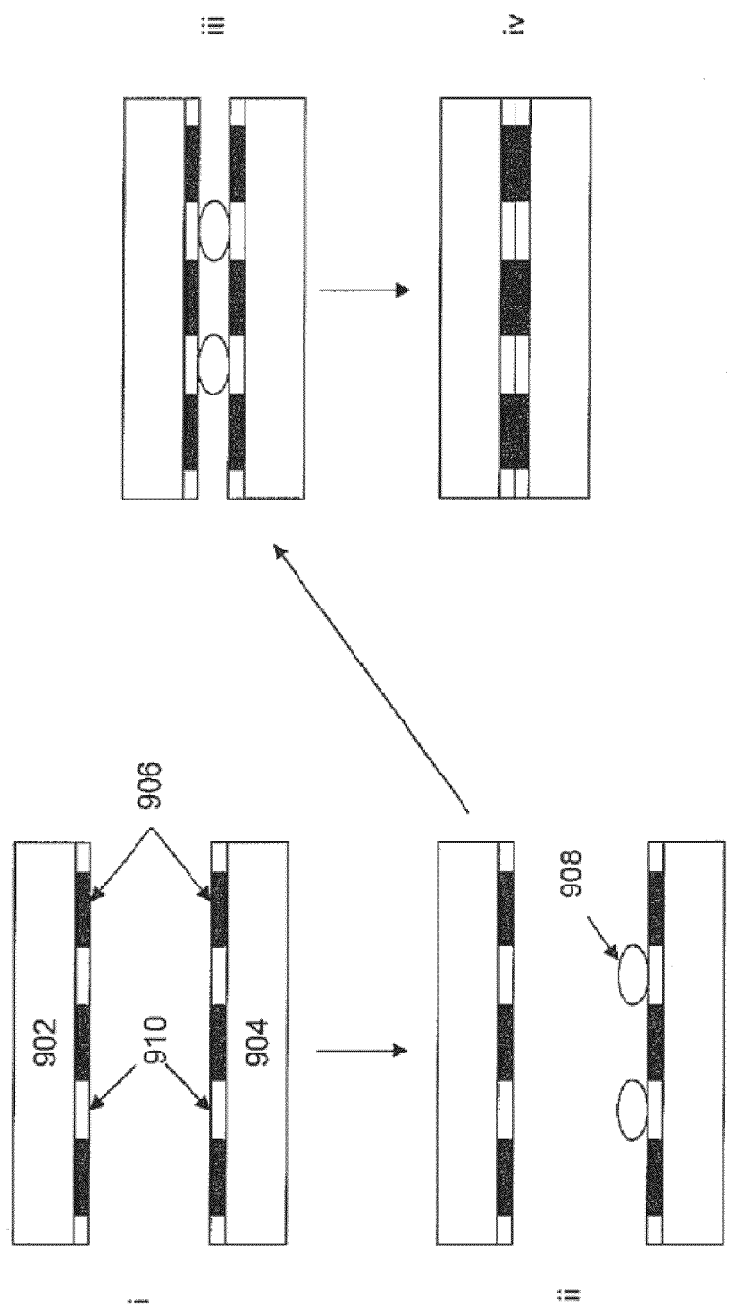
FIGS. 13D and 13E schematically illustrate a hybrid fabrication joining process.

For example, one could pattern complementary charged regions upon opposing component surfaces to result in an attractive force for the correct alignment. Likewise, patterning of hydrophobic and hydrophilic regions on opposing substrate surfaces, along with an aqueous joining process, would yield an automatic alignment process, followed by an appropriate process step to remove any remaining moisture from between the two parts. This process is schematically illustrated in FIG. 13D. As shown, two substrates 902 and 904 are provided with hydrophobic regions 906 patterned onto their respective surfaces. As will be appreciated, relatively more hydrophilic regions, e.g., corresponding to non-hydrophobic regions 910, could also be patterned onto the substrates, as could a variety of other surface treatments. These regions are patterned so that alignment of the regions on opposing substrates would yield alignment of components within such substrates (step i). An aqueous layer (shown as droplets 908) is deposited upon the surface of one or both of the substrates, which is generally repelled by the hydrophobic regions (step ii). When the substrates are mated together, the aqueous layer aligns to the corresponding non-hydrophobic regions 910 on the opposing substrate (step iii). Following correct alignment, the aqueous layer is removed, e.g., through conventional drying mechanisms (step iv). The resulting substrates are then joined through the Van der Waals forces between the chemically like (i.e., hydrophobic) regions on their respective surfaces.

Figure 13E:
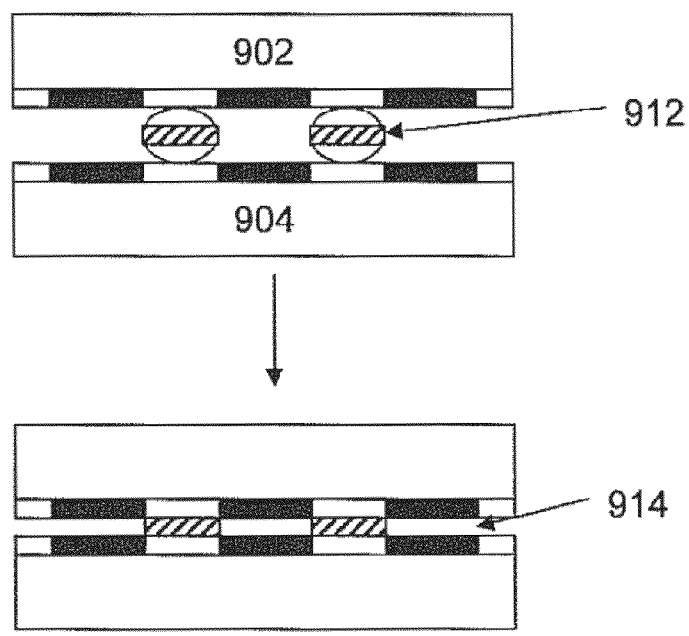

In accordance with this process, one could also readily introduce spacer elements in joining two device components, as shown in FIG. 13E. In particular, by providing either hydrophilic or hydrophobic spacing components, e.g., nanoscale spacer elements, can be provided into the bonding steps (e.g., shown in FIG. 13D). As shown, a hydrophilic spacer is provided within the aqueous film between the opposing substrates. The spacers localize to the hydrophilic regions and couple these regions together, leaving an air gap or space 914 in the bonded product. Again, as will be appreciated, hydrophiobic spacer elements are also optionally or alternatively used to align with and form bonding elements through the hydrophobic regions. The spacers may optionally comprise optical components, such as lenses, index matching materials, filter components, or the like., which are incorporated into the overall device and aligned in a self assembled manner during the bonding process.

V. Optical Components

In accordance with the present invention, in addition to integration of the sensor and reaction cell elements within a single analytical device, one or more optical components may be included within the device. Examples of integrated optical elements include, but are not limited to, directional optical elements, i.e., optical elements that alter the direction of optical signals to direct those signals at or to a sensor element or another optical element. Such elements include, e.g., mirrors, prisms, gratings, lenses, and the like. By way of example, in certain cases, parabolic reflector elements or micro-mirrors are integrated into the device to more efficiently direct optical signals in a given direction (See, e.g., U.S. patent application Ser. No. 12/567,526, filed Sep. 25, 2009, incorporated herein by reference in its entirety for all purposes). Other optical elements include spectral elements, e.g., elements that alter the spectral characteristics of the optical signals including directing spectral components of a signal or set of signals in differing directions, separating a signal into different spectral components, or the like. These elements include, for example, dichroics, filters, gratings or prisms that separate a given signal into spectral constituents.

In various embodiments, such optical components include contained optical enclosures that efficiently collect photon signals emanating from the reaction region and that are incident over a wide emission angular distribution, and direction of those signals to an assigned sensor element or elements. Such self-contained enclosures typically provide trapping within the chamber of substantial amounts of the photons emitted from the reaction region, elimination of cross talk between reaction cells or regions that would otherwise result from scattered signal entering adjacent sensor elements, reduction in leakage current since the sensing elements can be made extremely small, reducing scattering paths and scattering elements within each optical chamber, and reducing autofluorescence due to the substantially reduced optical path mass and eliminated free-space regions.

Figure 15:
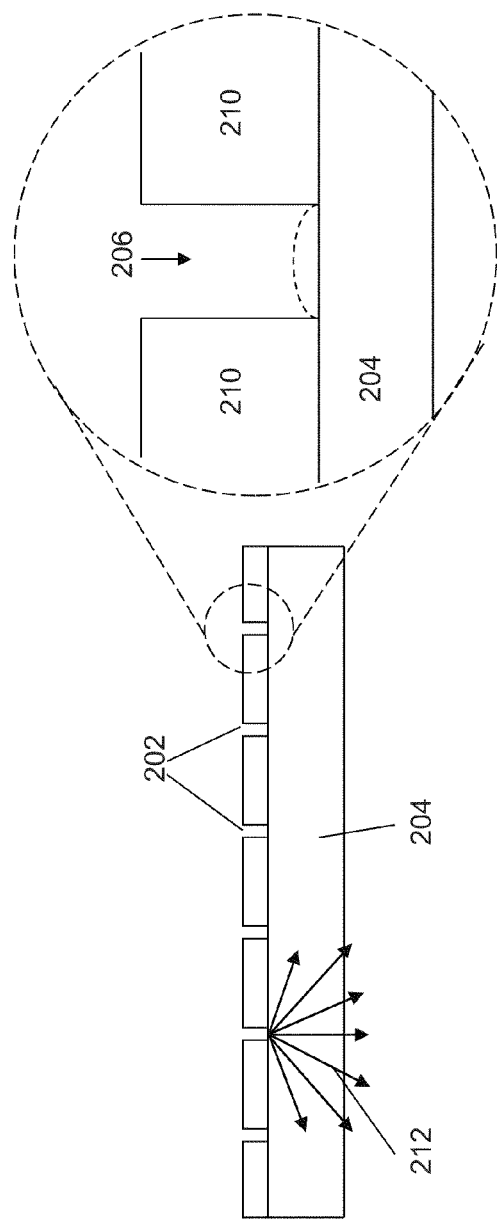
FIG. 15 is a schematic view of an array of reaction cells and the optical emission profiles emanating from those reaction cells.

FIG. 15 illustrates the general nature of optical signals from a reaction cell in various aspects of the present invention. As shown, the reaction cell or region comprises a very low volume reaction region such as a zero mode waveguides (ZMWs), e.g., ZMWs 202, disposed upon a substrate 204. As shown in the exploded view, a ZMW comprises an unfilled core 206 or aperture disposed through a cladding layer 210 that typically comprises a metal film layer. As described in, e.g., U.S. Pat. Nos. 6,917,726 and 7,486,865, the entire contents of which are incorporated herein for all purposes, the exemplary zero mode waveguide structure is of sufficiently small dimensions that light that is at greater than a cut-off frequency that enters into the waveguide core 208 is not propagated through the core but exhibits evanescent decay through the core. This allows for efficient illumination of just the volume of the ZMW at the opening (schematically illustrated by the dashed line within core 206), and collection of any optical emissions that occur within the same volume. The result is to permit excitation of and collection of fluorescent emission from individual molecules disposed at the opening of the core, e.g., on a transparent base layer. Light signals from the reaction cell, or ZMW 202 as shown, are emitted in a Lambertian distribution, as shown by arrows 212. Efficient capture of signals exhibiting this profile may necessitate either directional optics to re-direct the signals toward a detector, or provision of a detector that matches the hemispherical surface of this signal profile.

Figure 16:
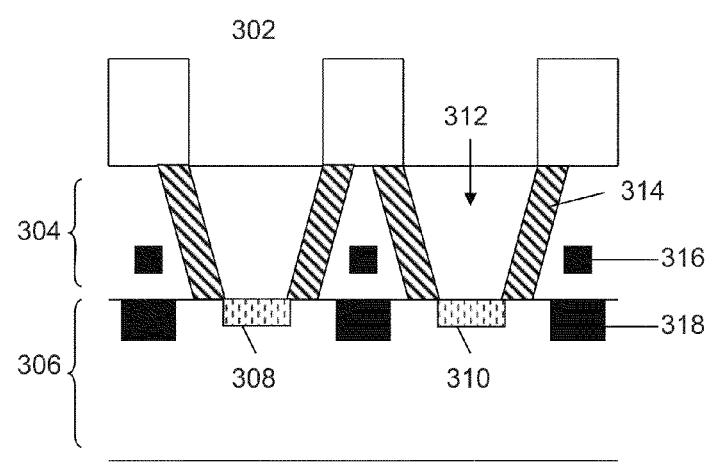
FIG. 16 is a schematic view of an optical containment structure for use in accordance with the invention.

In accordance with certain embodiments of the invention, an optical chamber is provided within the device, and particularly within a substrate, to efficiently trap and direct optical signals to the integrated sensor element. This aspect is schematically illustrated in FIG. 16. As shown, a reaction cell or region, such as a ZMW 302, is provided, disposed above a substrate layer 304. A detector 306 is disposed on or adjacent to the opposite surface of the substrate layer, which typically includes multiple sensor elements, e.g., sensor elements 308 and 310. An optical tunnel 312 or conduit is provided in the substrate to more efficiently convey optical signals from the reaction cell 302 to the sensor element(s) 308 and 310. The optical tunnel is typically comprised of reflective material, such as an integrated metal wall layer 314, that contains the optical signals within the tunnel, or it is comprised of a material having a sufficiently different index of refraction that maintains the optical signals within the tunnel by total internal reflection. As shown, other components, such as electrical interconnects and busses 316 and 318, for the sensor may also be provided either within the detector layer 306 or the oxide or other insulator layer above it.

Fabrication of these devices with an integrated optical tunnel may be carried out by a variety of fabrication processes that are typically used in the semiconductor manufacture process. For example, one may employ a number of processes to fabricate reflective metal tunnels within the intermediate layer between a reaction cell and a sensor element.

Figure 17:
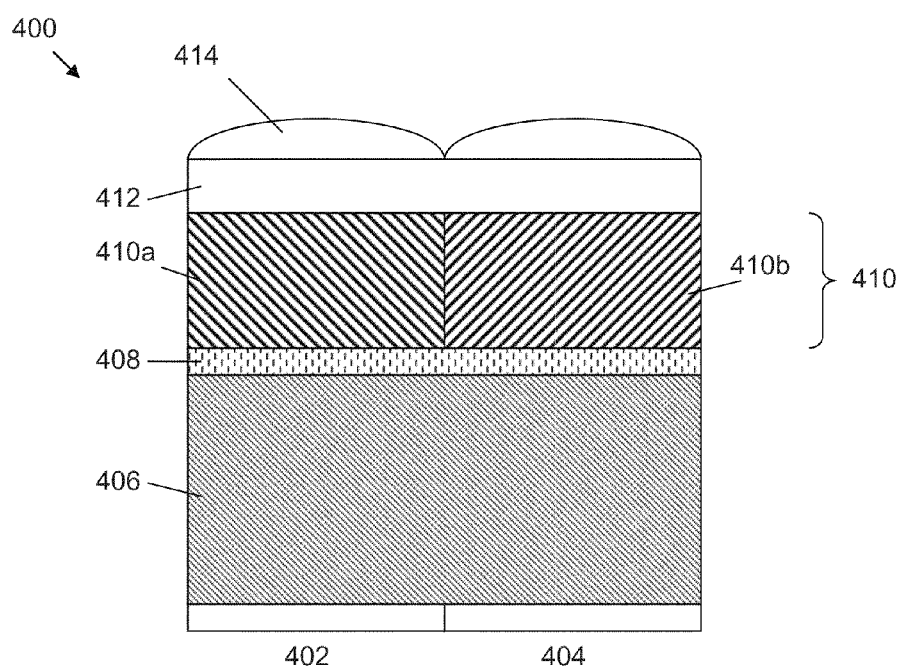
FIG. 17 is a cross-sectional, schematic view of pixels of a typical CMOS sensor used in the system in accordance with the present invention.

In one exemplary process, the optical tunnel portion is fabricated on top of the detector and sensor elements or portions thereof. For reference and ease of discussion, FIG. 17 schematically illustrates the typical structure of two pixel elements of a CMOS sensor based on detection by color differentiation. As shown, the overall structure 400 includes the silicon photodiode elements 402 and 404 that correspond to each pixel for the overall sensor or camera. Multiple additional layers are provided over the sensor elements, including an insulating oxide layer 406, nitride layer 408, optional color filter layers 410 that includes different spectral filters 410a and 410b to allocate spectrally different signals to different pixels, oxide layer 412, and microlens layer 414. The foregoing discussion is provided for ease of discussion of portions of the invention. The structure of CMOS sensors used in the invention, or even the type of sensors employed, include, but are not limited to, CMOS sensors, CCDs, etc. Although FIG. 17 illustrates a detector structure based on detection by color differentiation, one will appreciate from the description herein that other detection techniques may be employed.

Figure 18:
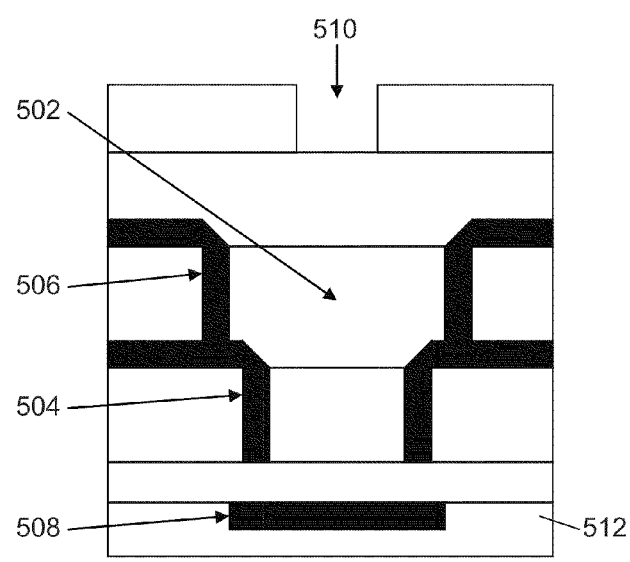
FIG. 18 schematically illustrates one structure of an optical containment structure of the invention.
Figure 19:
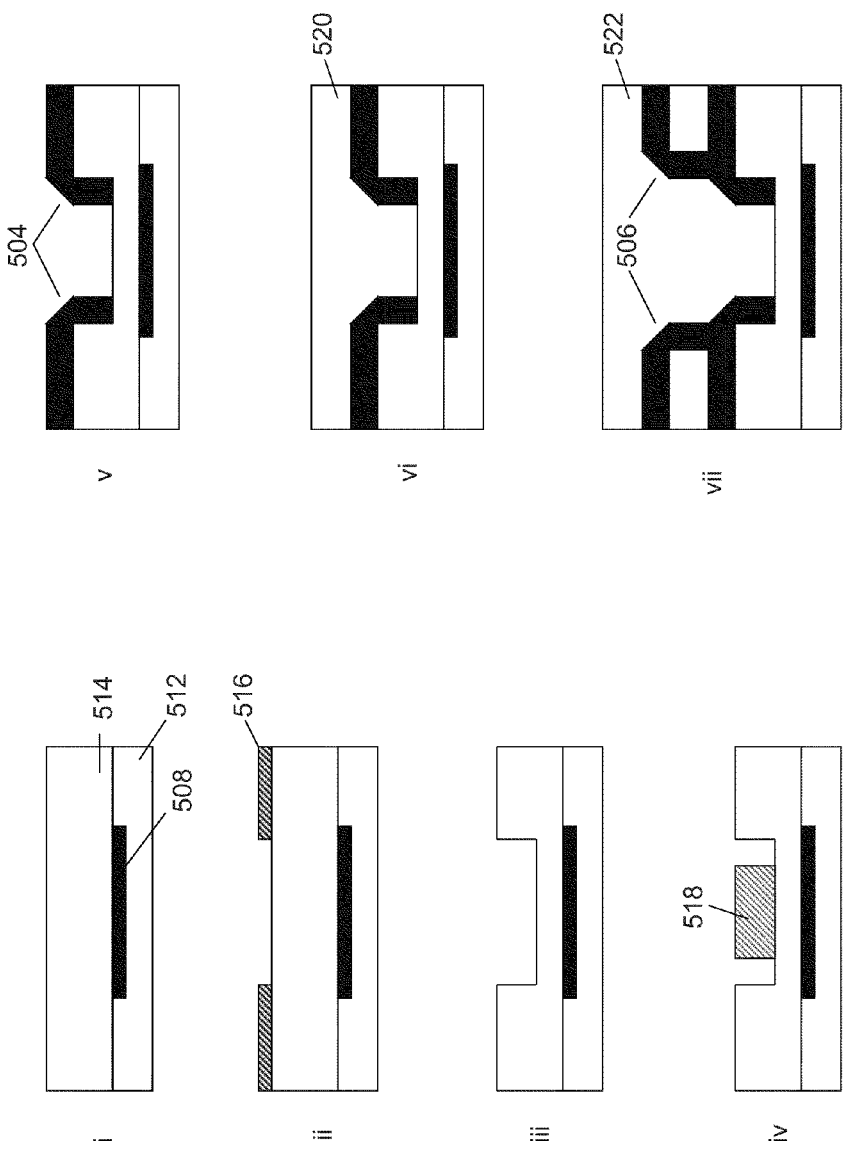
FIG. 19 schematically illustrates one process flow for fabrication of the structure shown in FIG. 18.

FIGS. 18 and 19 schematically illustrate one exemplary structure and fabrication process for an optical tunnel. As shown in FIG. 18, the metal tunnel 502 comprises a series of metal layers where each layer provides an annular ring or border 504 and 506 having an increasing cross section so that, collectively, such layers define a convergent metal tunnel that directs light to the sensor element 508 from reaction cell 510. FIG. 19 provides a schematic process flow for the fabrication of the structure shown in FIG. 18. As shown in step (i), an exemplary sensor array is provided, for which only a single photosensor pixel 508 is shown disposed upon a substrate layer 512, with an insulating oxide layer 514 disposed over it. A resist layer 516 is patterned over the insulator layer 514 in step (ii) to permit partial etching through insulator layer 514 shown at step (iii), e.g., in a time or depth controlled etch process. A second resist layer 518 is patterned over the etched surface to provide a mask for the central portion of the optical tunnel in step (iv). A conformal metal deposition step, e.g., evaporation, then provides a first metal ring or border 504 for the optical tunnel in step (v). An oxide layer 522 is then grown or deposited over the structure in step (vi). In step (vii), the processes are repeated to deposit subsequent metal ring layer 506 and oxide layer 524. As will be appreciated, this process may be further repeated to provide additional layers to the metal tunnel 502. One will appreciate that similar steps and processes can be used to manufacture any of the devices and components described herein.

Figure 20:
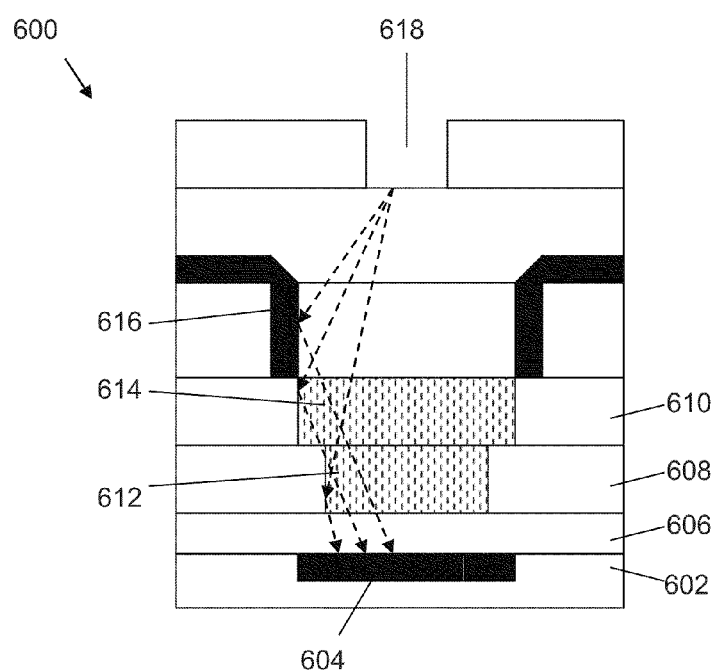
FIG. 20 is a schematic view of an alternate optical containment structure of the invention employing a mix of diffractive and reflective materials.

Similar fabrication processes may be employed to provide higher index of refraction (IR) material tunnels from the reaction cell to the sensor element, or devices that include a hybrid of a high IR tunnel component and a reflective (e.g. metal) optical tunnel. FIG. 20 provides a schematic illustration of a device having a higher IR material plug provided in the intermediate substrate layer between the detector and the reaction cell. As shown, the overall structure 600 includes a detector substrate 602, having a sensor element, such as silicon photosensor 604, disposed thereon. Oxide insulating layer 606 is disposed over the detector substrate. Layers 608 and 610 are provided with regions of higher index of refraction 612. These regions are of sufficiently high IR relative to the surrounding substrate material so that they funnel light to the detector by virtue of maintaining total internal reflection within the higher IR region. By way of example, if the high IR region possesses an IR of e.g., 2.04, such as is the case for a silicon nitride plug, that is disposed through and interfaced with an intermediate layer having an IR of 1.64, e.g., as in silicon dioxide, it would result in total internal reflection of any light impinging that interface at less than 30 degrees. As will be apparent from the description herein, a variety of methods are available for providing high IR regions precisely located within the substrate layer 608 and 610 including, but not limited to, etching followed by nitride deposition, e.g., liquid phase chemical vapor deposition (LPCVD).

Other index shifting materials may be included in the fabrication of the device, including, for example, doped silica materials, e.g., nanocrystal doped components or materials (See, e.g., U.S. Patent Application No. 2007-0034833, the full disclosure of which is incorporated herein by reference in its entirety for all purposes), and/or air or other gas-filled gaps or spaces to provide index mismatch to guide optical signals.

As shown in FIG. 20, an optional additional metal wall component 616, e.g., as described with reference to FIG. 18 above, is provided closer to the reaction cell 618. This permits the direction of optical signals from the reaction cell into the high IR regions at angles that are less than the critical angle for the interface of the high IR region and the surrounding substrate, e.g., less than 30 degrees for the exemplary silicon nitride/silicon oxide interface, and reduces the possibility of cross talk among adjacent portions of the device (as schematically shown by the dashed arrows).

As will be appreciated, because the devices of the invention are generally amenable to fabrication using standard monolithic semiconductor fabrication techniques, fabrication of the devices can incorporate much of the functional components that are employed for the detector, e.g., the electrical interconnects and busses used for a CMOS sensor array, as well as the optical components, (optical tunnels, lenses, mirrors, etc.), and even the reaction cells themselves, e.g., metal clad ZMWs. In addition, other functional elements may be integrated using the same or similar processes, including, for example, microfluidic elements that may be integrated into the overall device structure, and illumination components, e.g., for delivery of excitation illumination to the reaction cells.

Also as noted previously, although generally illustrated in terms of individual or a few reaction cells and associated integrated optical components and sensors, it will be appreciated that the illustrations and descriptions provided herein apply to much larger arrays of such reaction cells. In particular, such devices may generally have integrated into a single device more than about 1000 discrete reaction cells, and associated optics and sensors. In various embodiments, the integrated device includes a number of reaction cells in a range selected from between about 1000 and about 1 million, between about 2000 and about 1 million, between about 1000 and about 100,000, between about 100,000 and about 1 million, between about 1 million and about 10 million, and more than 10 million. It may be desirable to select the number of reaction cells based on the desired application. For example, the device may include between about 1000 and about 100,000 cells for clinical testing, between about 100,000 and about 1,000,000 for a diagnostic laboratory, or more than about 1,000,000 for high throughput research.

In accordance with the invention, each reaction cell may have an individual sensor element or pixel associated with it, or it may have multiple sensor elements or pixels associated with it (particularly where spectral separation, direction and separate detection are warranted). Likewise, each reaction cell may preferably have its own dedicated integrated optical components associated with it. In some cases, integrated optical components may be shared among multiple reaction cells, e.g., to apply standard filtering, to apply illumination to multiple cells, or the like, and will typically be in addition to one or more dedicated optical components.

As referred to above, in some cases, illumination optics are included within the integrated device structure. These optics may include actual illumination sources, e.g., LEDs, solid state laser components, or the like, and/or they may include optical conduits for transmission of excitation illumination from either an internal or external light source to the reaction cell. Examples of particularly preferred optical conduits include waveguides integrated into the substrate adjacent to the reaction cell. Examples of such illumination conduits have been previously described in, e.g., published U.S. Patent Application No. 2008-0128627, the full disclosure of which is incorporated herein by reference in its entirety for all purposes.

In various embodiments, the illumination source is reversibly optically coupled to the illumination ports. By "reversibly optically coupled" it is meant that one element, which is functionally coupled to another element, may be removed. In other words, the coupling is not permanent. As used herein, for example, the illumination source may be connected and disconnected from the illumination port.

As noted previously, optical cavities within the device may be useful in a variety of ways, depending upon the nature of the application and architecture of the device. For example, such gaps or spaces may be employed in the optical train to provide additional signal funneling to a detector or sensor element. Alternatively, these gaps may provide an illumination conduit for delivery of illumination radiation to a reaction cell.

VI. Detector Components

As noted previously, in some applications, it may be desirable to distinguish different signal components, e.g., to identify that both a reaction has occurred and to identify the participants in that reaction. By way of example, in the case of nucleic acid sequencing, one can provide different nucleotides with different optical labeling groups thereby allowing not only detection of a polymerization reaction but also identifying the particular type of nucleotide that was incorporated in that polymerization reaction. Accordingly, it would be desirable to include the ability to distinguish different signal components within the devices and/or systems of the invention.

In some optical systems, the ability to distinguish different signal components is achieved through the use of, e.g., different filtered optical trains, or the inclusion of dispersive optical elements to differentially direct different spectral components of a signal to different detectors or different regions on a given detector array. In various embodiments, the system is configured for detection and differentiation based on other detection techniques. Various aspects of the detection devices and methods are similar to those described in U.S. Patent Publication Nos. 2007/0036511 filed Aug. 11, 2005, 2007/0036511 filed Aug. 11, 2005, 2008/0080059 filed Sep. 27, 2007, 2008/0128627 filed Aug. 31, 2007, 2008/0283772 filed May 9, 2008, 2008/0277595 filed Sep. 14, 2007, and 2010/0065726 filed Sep. 15, 2009, and U.S. Pat. Nos. 7,626,704, 7,692,783, 7,715,001, and 7,630,073, the entire content of which applications and patents are incorporated herein for all purposes by this reference.

In the context of integrated devices, the available space for use in differential direction of signal components is generally reduced. Similarly, where a single sensor element is assigned to a reaction cell, one may be unable to direct different components to different detectors.

The integrated device may include directional components and/or filter components that selectively direct different spectral components of a signal to different adjacent pixels or sensors within the device. By way of example, a given reaction cell and its associated optical train may include multiple individual sensor elements associated with it, e.g., pixels. Included within the optical train would be a directional component that would direct spectrally distinguishable signal components to different sensor elements or collections of sensor elements. Examples of such components include prisms, gratings or other dispersive elements that can redirect and separate signal components. The use of such components in optical systems is described in, e.g., published U.S. Patent Application No. 2008-0226307, the full disclosure of which is incorporated herein by reference in its entirety for all purposes.

In addition to such directional elements, or as an alternative to such elements, multiple sensor elements may be provided with filtering optics that allow only a single signal type to reach that particular sensor element. Each sensor is differently filtered to allow it to detect a particular signal component, to permit multicolor distinction. In particular, each of a plurality of sensor elements within a given reaction cell's dedicated optical train is provided with a filter that narrowly passes one component of the overall signal from the reaction cell. For example, the signal associated with a given nucleotide incorporation event would be passed by a filter on a first pixel element, but rejected by the filter on three other adjacent pixel elements. Each of the different filter layers on each sensor would be selected for the given signal components for a given application. Further, each reaction cell could have one, two, three, four, or more pixel elements dedicated to receiving the signals from that reaction cell. In some cases, 5, 10, 20, 50 or even 100 pixels or more could be devoted to a given reaction cell.

Deposition of a variable filter layer, i.e., providing different filters on different pixels or collections of pixels, may generally be accomplished during the fabrication process for the overall integrated devices or the underlying sensor elements using conventional CMOS fabrication processes. Likewise, dichroic filters are equally amenable to fabrication/patterning onto the sensor elements to reject any potential excitation illumination.

Alternatively, or in addition to selective direction/filtering of the output signals from a reaction cell, distinguishing signal components may also be accomplished by detecting an output signal in response to a specific excitation event. In particular, if a signal is received in response to an excitation radiation that is specific for a given signal generator, e.g., fluorescent label, one can assume that the label is present. By modulating or interleaving the excitation illumination across the excitation spectra for multiple fluorophores having differing excitation spectra (or different excitation/emission profiles), one can identify when any of a set of fluorophores is present in the reaction cell. By correlating an emitted signal with a given excitation event, one can identify the fluorophore emitting the signal. Examples of this process are described in published U.S. Patent application No. 2009-0181396, the full disclosure of which is incorporated herein by reference in its entirety for all purposes. As will be appreciated, the timing of illumination, the frame rate of the detector, and the decay times for the fluorophores are matched to provide optimal detectability of each different signal event, without different events bleeding over into each other, while also permitting sufficient sampling during a given frame capture event for the detector, that no individual events are missed.

Figure 21A:
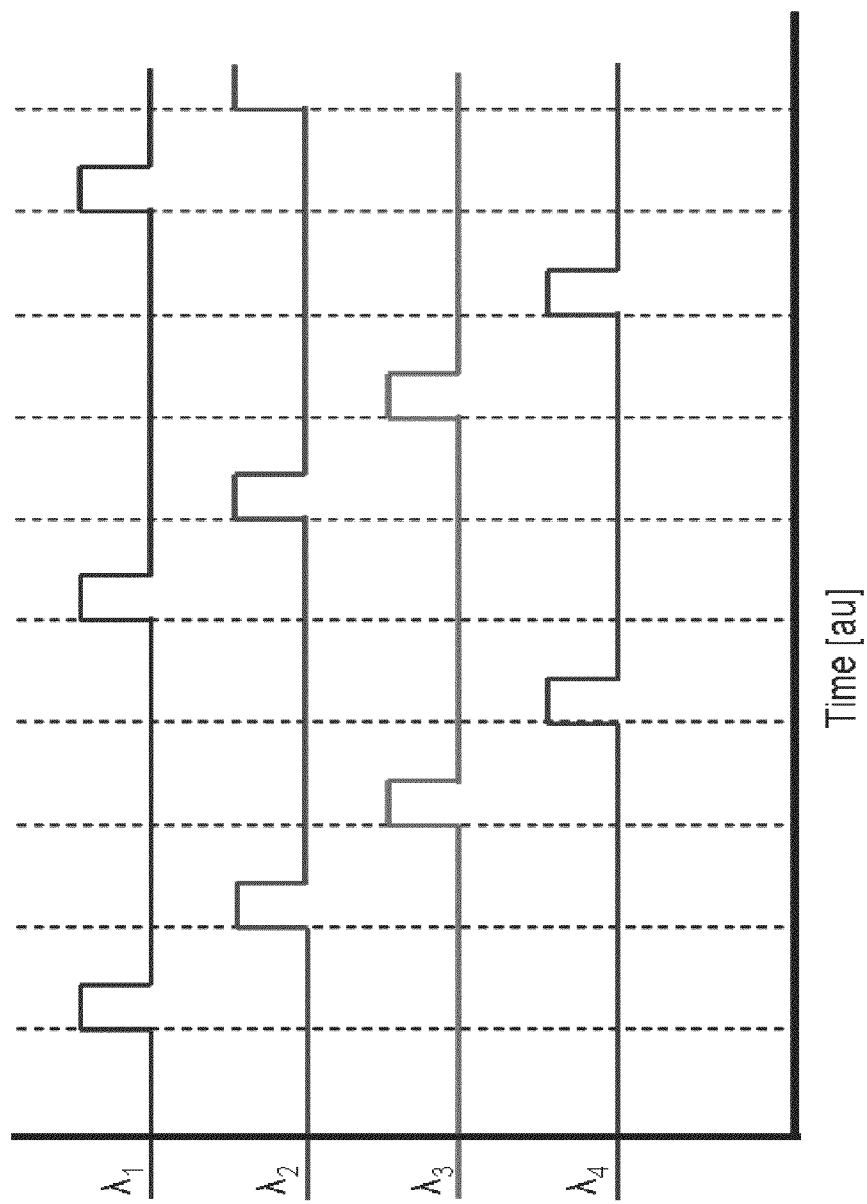
FIGS. 21A, B and C show exemplary plots of interleaved excitation illumination and signal data using a system similar to that of FIG. 23
Figure 21B:
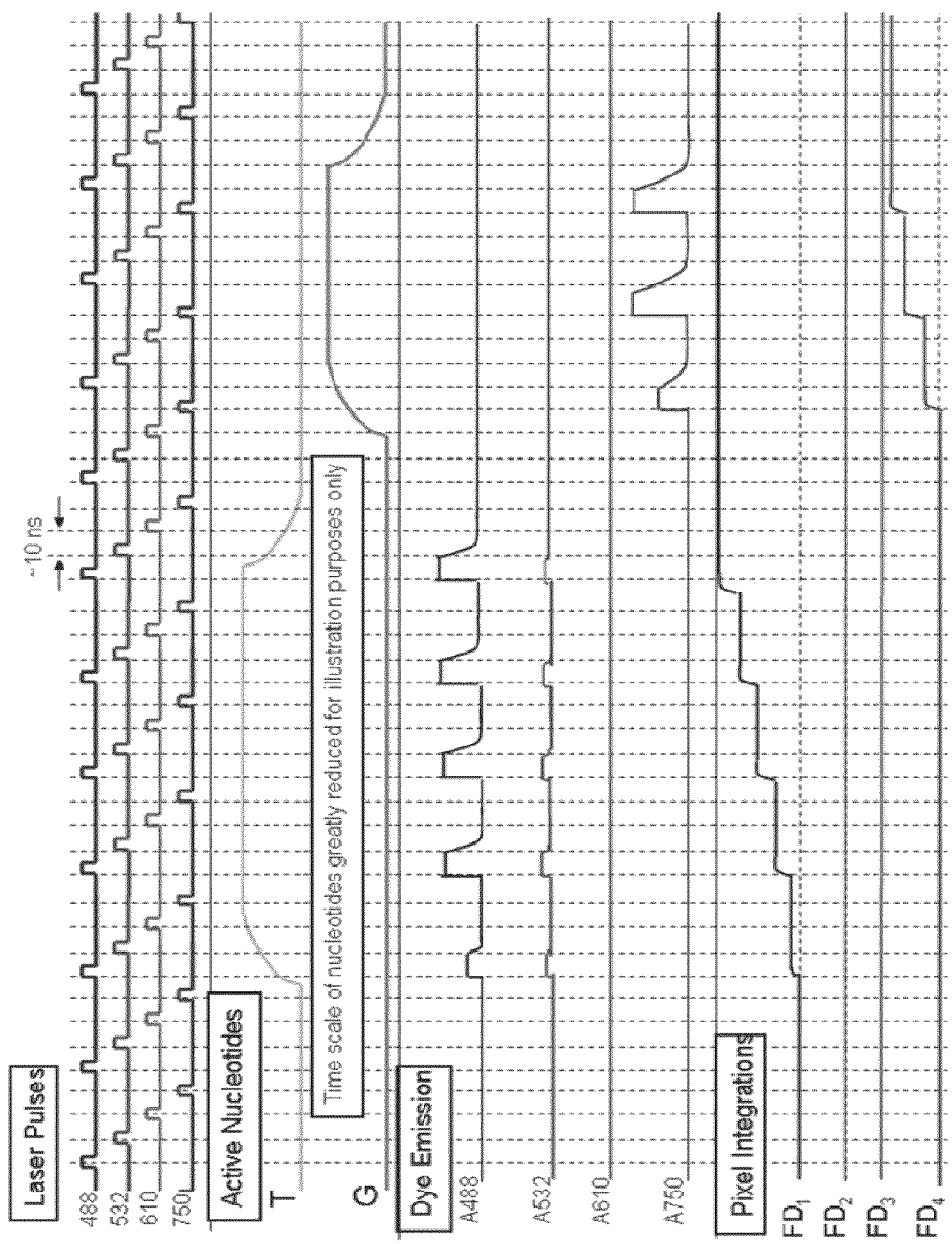
Figure 21C:
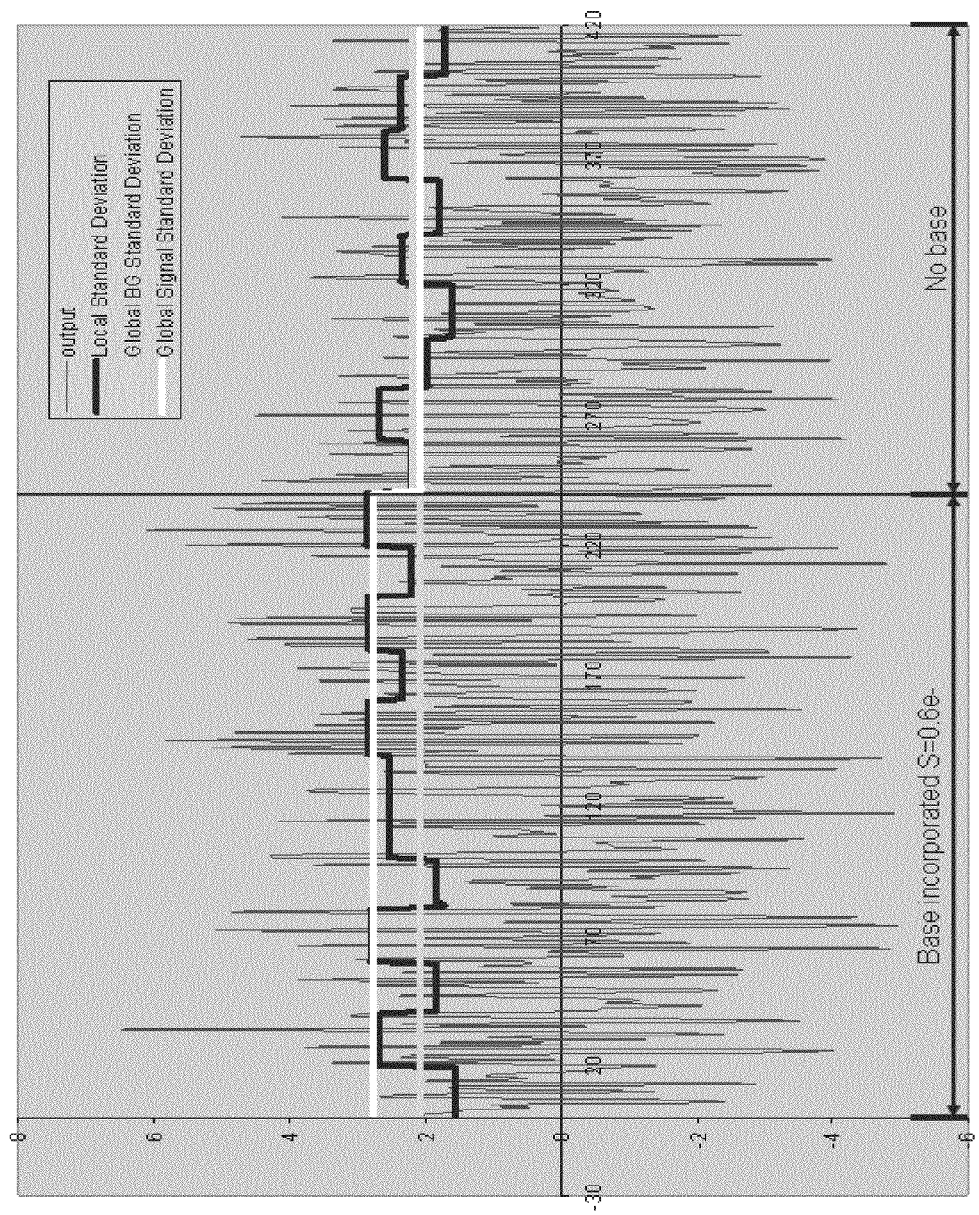

In an exemplary process, a given application that includes multiple different labeled species, e.g., different labeled nucleotides, includes labels that differ in their excitation spectra. Illuminating a reaction mixture iteratively with the different wavelength excitation sources provides temporal separation between excitation of the different labels. By correlating an emitted signal with one of the different excitation wavelengths, one can interpret the signal as emanating from a given label. In operation, one can cycle through the various different excitation sources at high frequencies, and detect the correlated emissions at equivalently high frequencies. This is illustrated in FIGS. 21A, 21B, and 21C. As shown in FIG. 21A, different excitation sources are pulsed in an interleaved fashion. Exemplary timescales of such pulses are illustrated in FIG. 21B, along with the corresponding expected residence times of detectable species, and the expected signals that would emanate from those species. Also shown is the pixel integration over a given frame that includes multiple cycles through the various excitation pulses.

FIG. 21C shows simulated integration and detection of a signal from a labeled reactant (left half of plot), and the absence of a labeled reactant (right half of plot), even in the presence of high noise levels (pulse extraction with a signal of 0.5 electron/sample and 6 samples per frame and a 1 electron background).

In accordance with the invention, an integrated smart pixel can be employed in efficient detection and distinction of the various signal elements that would derive from the foregoing. A schematic of the pixel design is provided in FIG. 22. As shown, the pixel including a photodiode 1102 includes four integrated storage elements 1104, each of which may be electronically gated by the activation of a separate excitation source. In such cases, a modulated controller element would be coupled to both the detector and the excitation illumination sources to synchronize the illumination and storage events. As a result, each storage element will be correlated to a given excitation event and consequent emission event, such that detected signals for each different type of excitation event are relegated to a different storage element.

In addition to being correlated to discrete excitation events, additional correlations may be pre-programmed into such systems. For example, any delay between an excitation event and an emission profile, e.g., for a given type of labeling group, may be preprogrammed into the pixel so as to take such delays into account in the detection event. Likewise, all storage elements could be switched off during intermediate stages of the excitation process, to avoid any noise contributions, slower decay rates of some signals, etc. As shown, and as will be appreciated, conventional logic elements, amplifiers, etc. are also included.

Figure 22:
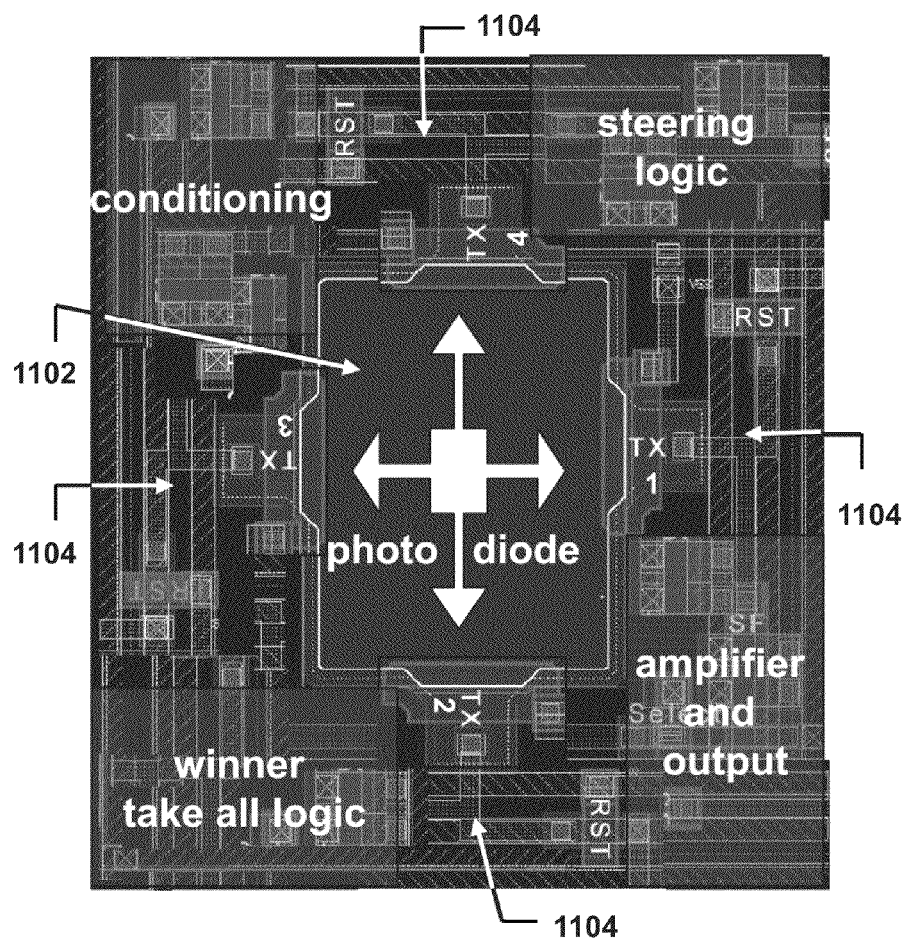
FIG. 22 is a schematic view of a pixel design with optionally gated storage elements.

The exemplary pixel detector of FIG. 22 contains steering logic and multiple integrating nodes. The nodes can be run simultaneously or switched during optical integration periods. The photodiode 1102 is connected to a plurality of integrating and processing nodes 1104. These nodes are generally connected to the photodetector via transfer gates (TXn). In depletion mode, these channels are non-conducting (i.e. open) when a low voltage is applied to the gates. When a high voltage (e.g. several kT above the transistor threshold voltage) is applied, however, a conducting path is made between the nodes and the photodetector. In various embodiments, each integrating node is independently reset to clear the previous charge from its circuits prior to transfer operations. Although the exemplary photodetector uses CMOS, NMOS or PMOS technology, any MISFET, BJT or other switching circuit elements can be substituted without altering the basic disclosed operation.

The use of multiple integrating nodes on a common photodetector can be used to separate photocharge events of many causes. In various embodiments, the detector is configured as a vertical detector whereby the depth of absorption of photons in the detector is related to its energy level. Having multiple collection nodes at different depths in the detector provides a method to determine the color of the incident illumination by comparing the relative strengths and absorption depth of the signals. In this case, generally all the transfer gates are active simultaneously and the optical integration time can be controlled by the transfer gate active duration time. Based on the previous events, each integration time can be different to essentially equalize or extend the operating dynamic range.

In various embodiments, the arrival time or resonant phase of a photon to a regular or synchronized event can be used to classify the species of the signal. If each signal is responsive to different input stimulus, the stimulus can be applied in a regular and sequential fashion. By synchronizing the stimulus with an unique integrating node, the species can be determined. If a lag in response to a frequency modulation of the stimulus (chirped, swept, constant) exists, this phase margin can be detected by appropriately delaying the transfer gate to each integrating node with the in-phase signal from the stimulus. In each of these cases, the relative response from each integrating node can be used to positively identify and classify the species.

One will appreciate that this architecture can also be used to determine high speed events (sub-frame rate) by storing multiple sub-frame samples that could have temporal overlap. In various embodiments, the detector includes local storage within pixels to achieve high speed burst collection.

VII. Overall Analytical System Architecture

Figure 23:
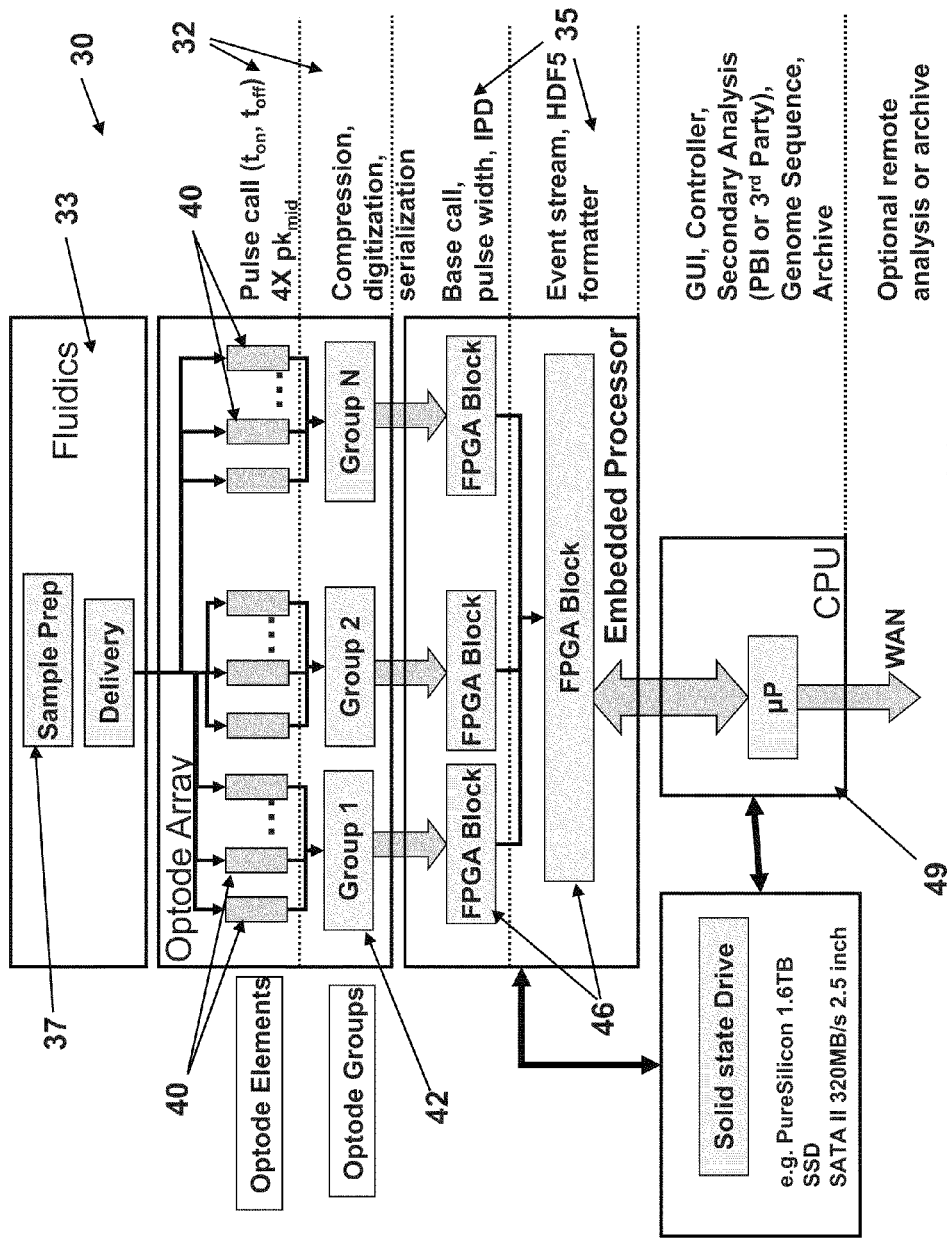
FIG. 23 is a schematic of an analytical system having a plurality of integrated analytical devices in accordance with the present invention.
Figure 24:
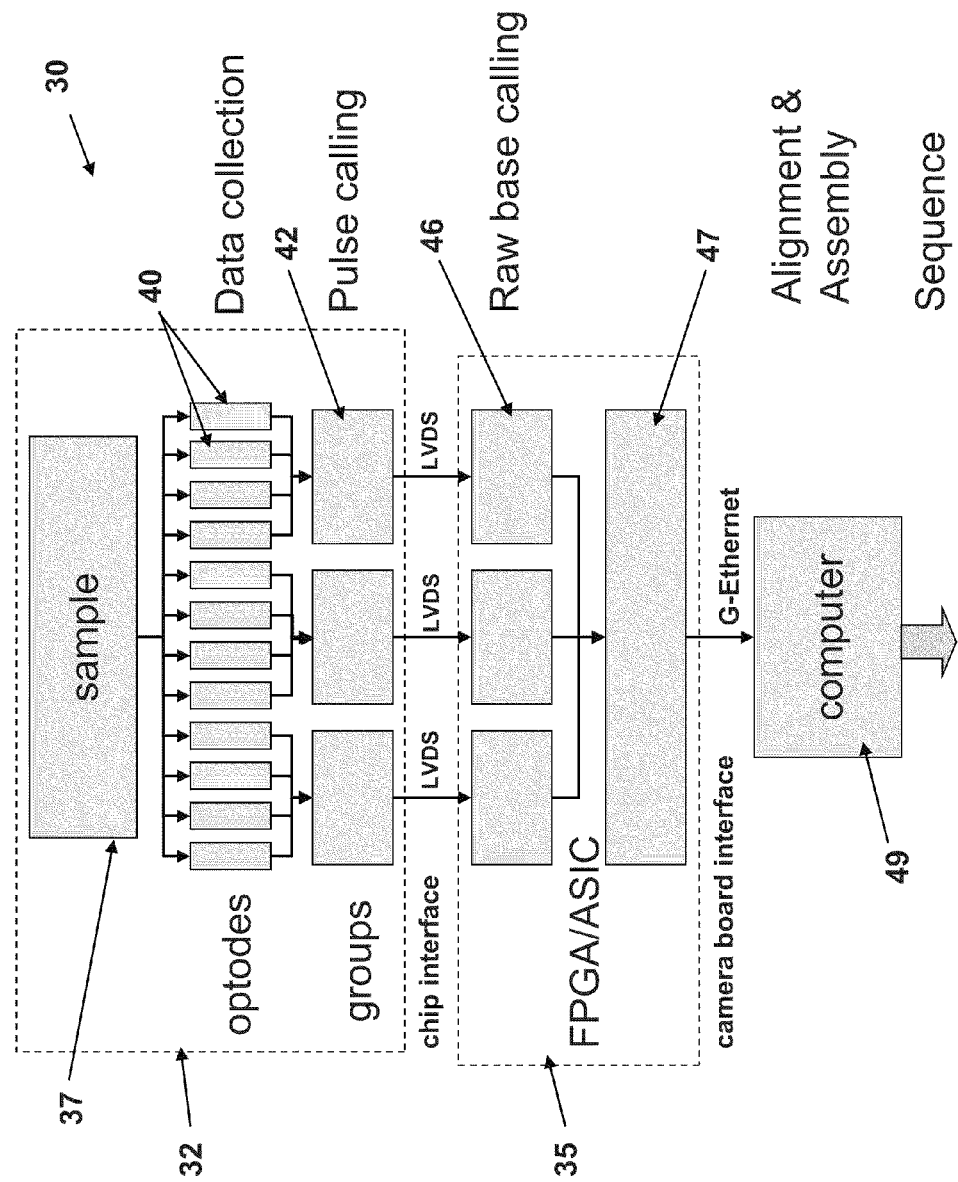
FIG. 24 is a schematic of an analytical system having a plurality of integrated analytical devices.

Turning to FIG. 23 and FIG. 24, a large number of optical analyses, including those described herein, utilize a common overall analysis system architecture, generally designated 30. While the components and configuration of system 30 may vary, in various embodiments the system has the general structure shown as block diagrams in FIG. 23 and FIG. 24. In various embodiments, the present invention is directed to a scalable system architecture utilizing an analytical assembly, generally designated 32. As shown, the exemplary system further includes a sample delivery assembly 33 and a processing system 35.

In FIG. 23, the exemplary system includes an integrated sample delivery system. The exemplary sample delivery system 30 includes a sample 37 and sample delivery device 39, such as a fluidics system. The sample delivery system delivers the sample to the analytical assembly. The addition of a microfluidic channel on the device may reduce sample and reagent volume and improve the control of the flow of reagent to the device.

The exemplary analytical system 30 includes a plurality of analytical devices, generally designated 40, similar to the optodes described above. Two or more analytical devices are grouped into an analytical group 42. The analytical group may be an integrated unit having one or more analytical devices connected by local fluidics, photonics, and detection components. In various respects, analytical device 40 and analytical group 44 are used somewhat interchangeably with "optodes" or "optode array".

Analytical devices 40 are generally configured for optical analysis and data collection as described above. In turn, each analytical group is optionally configured for compression, digitization, and serialization of the data from the respective analytical devices. In various embodiments, the number and type of analytical devices corresponds to the analysis function to be performed. In various embodiments, the system includes more analytical devices than analytical groups. In various embodiments, the number of analytical devices corresponds to the number of base pairs to be sequenced.

The system 30 provides a processing system 30 downstream from the analysis assembly for processing and interpreting the data. The exemplary processing system includes a plurality of optional field programmable gate array (FPGA) blocks 46 and application-specific integrated circuits (ASIC) 47, which in turn are coupled to the one or more analytical groups. Each processing assembly is configured for raw base calling and optional functions such as pulse width control. Exemplary system 30 further includes a central processing unit (CPU) 49 for processing data and controlling the overall system. The CPU is optionally connected to a data storage unit such as a solid state memory device.

In exemplary system 30, the analytical assembly is integrated and self-contained. In various embodiments, the overall system, including one or more of the analytical system, sample delivery system, the processing system, and other components, is formed as an integrated system.

In various respects, the analytical system makes use of an integrated device similar to that disclosed in the '235 application incorporated above and the optode array description above. Grouping of the system elements generally allows for use of commercially viable manufacturing methods with common I/O and local processing for data reduction.

As will be appreciated from the description herein, various aspects of the present invention are directed to methods to create a scalable architecture where data is pipelined in a parallel fashion to provide sample segment time series data of incorporation events. The data is output from the integrated analytical devices 40 on many parallel low cost commercial channels such as low voltage differential signaling (LVDS) (e.g. ANSI-644). This exemplary approach can minimize I/O pads to provide a low-cost and easy to manufacture system compatible with many off-the-shelf quality test sockets (e.g. ATE socket). In various embodiments, each LVDS output can be connected to a digital signal processing block to maintain pipelined data stream processing in an embedded processing board.

The exemplary system of FIG. 23 is configured for genomic sequencing. In operation generally, a sample is delivered to analytical devices 40 for data collection. The collected data is transferred to analytical groups 40 and then processed by processing system 35. The overall system has a modular design such that system can be scaled efficiently. Because the system includes a defined data path from analytical device to processing, the system can be scaled up simply by adding components.

In the exemplary system, processing system 35 is a durable camera board (e.g. FPGA). A parallel processing function is embedded in the camera board and performs the base calling and formatting functions. The camera board performs these functions on data output from the analytical devices. In the exemplary embodiment, camera board is synchronized with the individual element events at each analytical device. By formatting the data at the embedded camera board, the downstream processing (typically called "secondary analysis") can be performed with third-party software, proprietary internal routines, or a combination thereof.

An advantage of the exemplary integrated system is that the data reduction at the board level can result in the ability to transmit this data file to a remote location for further processing or archiving. In the exemplary system, the upstream distributed processing and local data stream processing allow for portable sequencing systems for low multiplexing and distributed genomic data processing. For example, a small lab may be able to employ the services of computational and storage facilities on a per-use-basis. As will be appreciated from the description herein, these and other advantages are enabled by the modularity of the data collection and processing functions.

In various embodiments, the analytical device or devices 40 is an integrated, portable device configured for local data stream processing. In one example, a single-use analytical system includes 60,000 individual analytical device elements grouped in an area less than about 1 $mm^2$ Sample can be prepared off the device and introduced into the device via microfluidics channels, e.g., fluid delivery system 33 In various embodiments, the analytical array includes local, integrated components including, but not limited to at least one of a fluidics system, a power source, an illumination system, a detector, a processing circuit, a controller, steering logic, and electrical connections. The exemplary device includes a portable, on-chip, battery-powered light source (i.e. LED or laser) and a single FPGA can process the data stream (e.g. 65,000 samples at an average of 25 bases per second). The detection methods described herein can be adjusted to maintain a bandwidth where a single LVDS channel would interface to the FPGA and a standard PC interface can be provided from the FPGA output to the external analysis equipment.

In various embodiments, system 30 includes a number of optodes 40 selected from the group consisting of more than or equal to about 1000 optodes, more than or equal to about 100,000 optodes, and more than or equal to about 1,000,000 optodes. In various embodiments, the system includes from about 1000 to about 100,000, from about 100,000 to about 1,000,000, or more than a million optodes 40. In various embodiments, the system includes more than 1000 optodes formed on a single LVDS chip. In various embodiments, the system includes a plurality of chips, each including a plurality of optodes.

The exemplary system of FIG. 24 is substantially similar to the system of FIG. 23. In FIG. 24, the exemplary system includes an optode array 40 configured to sense sequencing data in a massively parallel fashion. Each of these events is asynchronous. The circuits in the device can be used to align these random events to a system clock and the sequence can be scheduled to read the data off the chip in a serial or parallel synchronous way. Some level of determination of base calling may be preformed, or alternatively, the raw data from each channel can be output. Local time bases are used to provide the option to calculate the durations of pulses and the time between events.

The exemplary system of FIG. 24 is a fully pipeline architecture that uses data reduction upstream with increasing levels of signal aggregation and common processing downstream. A common sample 37 is applied to a multitude of optode elements 40 where parallel sampling operations are concurrently or essentially concurrently performed. These sampling operations can be made in synchronous or in an asynchronous fashion. The data are raw signals acquired from each sample piece. In various embodiments, the data is processed at this level. In various embodiments, the data processing including noise reduction, signal amplification, and/or aggregation into events and pre-classification based on programmed rules. These operations generally do not require information from other data collection elements.

The data are passed to the next stage in the pipeline where groups of elements are combined 42. Among the benefits of this combining of elements are the cost reduction of common processing circuits, the ability to make a comparison of adjacent elements for increased performance (e.g. cross talk reduction), and the ability to conduct pre-processing of data (e.g. digitization, buffering and synchronization or serialization) to enhance downstream efficiency. Each sequencing event is characterized by a signal pulse. The use of common processing circuits at the group level 42 may refine the event-driven data from the optode elements 40 into high confidence event pulses for classification in downstream operations.

In various embodiments, the pulses containing information including temporal onset and offset times, signal strengths, and other signature classifiers are transmitted to off-chip circuits. The use of on-chip circuits increases the cost of the sequencing chips, and transferring some of the data off-chip and reducing the amount of data generally provides cost benefits. By transmitting the data in a combined and serialized form (digital and/or analog), the input/output (I/O) paths are reduced, which increases chip yield and lowers costs. One common approach for serial chip-to-chip or chip-to-board communication is via the LVDS signaling standard. This standard defines a low voltage differential layer to transmit arbitrary data formats. The LVDS standard is commonly used in the computer arts such as in the USB protocol.

By transmitting data to a camera board, enhanced signal processing can be performed. This board level processing can take advantage of commercial devices such as microprocessors, digital signal processing (DSP), and field programmable gate arrays (FPGAs) among other components. These devices can be arranged in parallel to classify the events based on the aggregate pulse level information to increase throughput. Algorithms that increase effectiveness by training against previous data runs or via tuning with the streaming data can be employed to increase performance. By using the data including the time between pulses, the relative strengths of each color signal, and other signature classifiers, the specific symbol representing the species of reagent incorporated into the polymer can be determined. In addition, based on the relative fit against modeled and measured data, an estimate of the certainty of this determination can be made. Downstream processing in the computer 49 can take advantage of this determination certainty level to better perform alignment and assembly of the separate data streams into a full sequence set.

The exemplary architecture can be extended to include an array of blocks similar to the format of FIG. 24 on a single device or chip. Multiple discrete samples could be independently applied to each bank of processing sensors or a common sample can be extended to this higher multiplex for faster operation. In this manner, the architecture provides for scalability and high throughput with high confidence levels.

Additionally, the use of embedded circuits to operate on the data downstream from optode array 40 provides for many advantages. The circuits can be made reconfigurable to enable many applications (i.e. DNA, RNA, proteomics), support field upgrades in data processing routines or changes in the system sample or chemistry. Higher order analysis (i.e. advanced trace to base, initial alignment routines) can be performed on these data streams. By maintaining pipelines along device multiplex partitions, the entire system is scalable. If additional groups are added, additional embedded cores are added in concert. Thus, by modifying conventional components and integrating them as described, a system may be capable of high throughput sequencing in a small package, at reduced cost, and with increased scalability and flexibility. One will appreciate from the description herein that the system and device of the invention provides excellent scalability and the potential to sequence an entire genome in a fraction of the time of existing devices.

Although the analytical devices of the present invention typically include multiple elements for an analytical system integrated into a single device architecture, it will be appreciated that in many cases, the integrated analytical devices may still employ a companion instrument system to provide additional functionality for the analysis of interest. In particular, as noted previously, in some cases the illumination of optical analyses will utilize an illumination source that is separate from the integrated device structure. For example, lasers, LEDs or other conventionally employed illumination sources may be provided within a larger instrument that is mated with the integrated device. Likewise, power supplies for the integrated device, where needed, may also be provided within an instrument architecture. In addition, any environmental controls, fluidics, fluidic control components (whether electrokinetic, pressure based, or control of integrated pumping and valving mechanisms, or other) may be provided within the instrument architecture. As will be appreciated from the description herein, any number of these components may be integrated into the system or connected remotely. For example, the illumination components can be integrated into the system with a system platform and connected to the analytical device array with a test socket as described above. In another example, the illumination components are provided in a separate illumination instrument and connected to the system in conventional manner.

Where such other functionalities are provided within an instrument architecture, such an architecture may include one or more interfaces for delivering the particular functionality to the integrated device. For example, optical interfaces may include fiber optic connections, optical trains or other optical interfaces to provide illumination to complementary connections on the integrated device, which then communicate that illumination to the reaction cells or otherwise, as necessary.

Electrical and data connections may also provide the requisite power and data communication between the sensor components of the device and a processor that may be integrated into the instrument architecture, or that may be exported or communicated to an associated computer that is external to the instrument itself.

Fluidic interfaces are also optionally provided within the system architecture for easy delivery of reaction components to the reaction cells. In various embodiments, the fluidic interface comprises fluid connectors that permit the sealed connection of fluid reservoirs in an instrument with complementary connections on the analytical device, including, for example, fluidic manifolds with controllable valving and pumping mechanisms. In various embodiments, the fluid connectors are provided on a test socket into which the analytical device array is seated.

Other interfaces include, for example, control interfaces with the device for controlling movement of fluids around an integrated device. Such interfaces may include electrical interfaces, e.g., to drive electrokinetic transport or to power integrated pumping and valving mechanisms, or pneumatic or hydraulic interfaces, to perform similar controls.

Devices will also typically include user interfaces, e.g., tabs, grips, or the like, for the convenient handling of such devices, and to ensure correct orientation when interfaced with the instrument, e.g., tabs, pins or holes, so that a device is correctly mounted to the instrument.

One of skill will appreciate from the description herein that the system and method of the present invention generally increases flexibility, promotes scalability, and reduces costs. The system architecture of the invention enables many concurrent sequencing applications.

By developing systems with common design elements, great economy of scale may be achieved and result in overall reductions in part costs, field service and development time and resources. Bundling parts across these applications may provide enhanced buying power and better ability to manage yield and overall quality.

One will appreciate from the description herein that the configuration of the system and one or more self-contained analytical devices may be modified. Further, the configuration of each analytical device and respective integrated optical elements can be modified. For example, a plurality of self-contained analytical devices including respective integrated optical elements can be grouped together with common I/O and local processing for practical device manufacture. This architecture can be further extended for increased scalability to higher order signal processing and assembly of individual segment data into an overall sequence set. As discussed above, several partitions may provide commercial, cost-effective solutions across a capital equipment and single use device partition.

One will appreciate from the description herein that any of the elements described above can be modified and/or used with any of the other elements, in any combination, in the system in accordance with the present invention.

VIII. Scattering Detection

Figure 25:
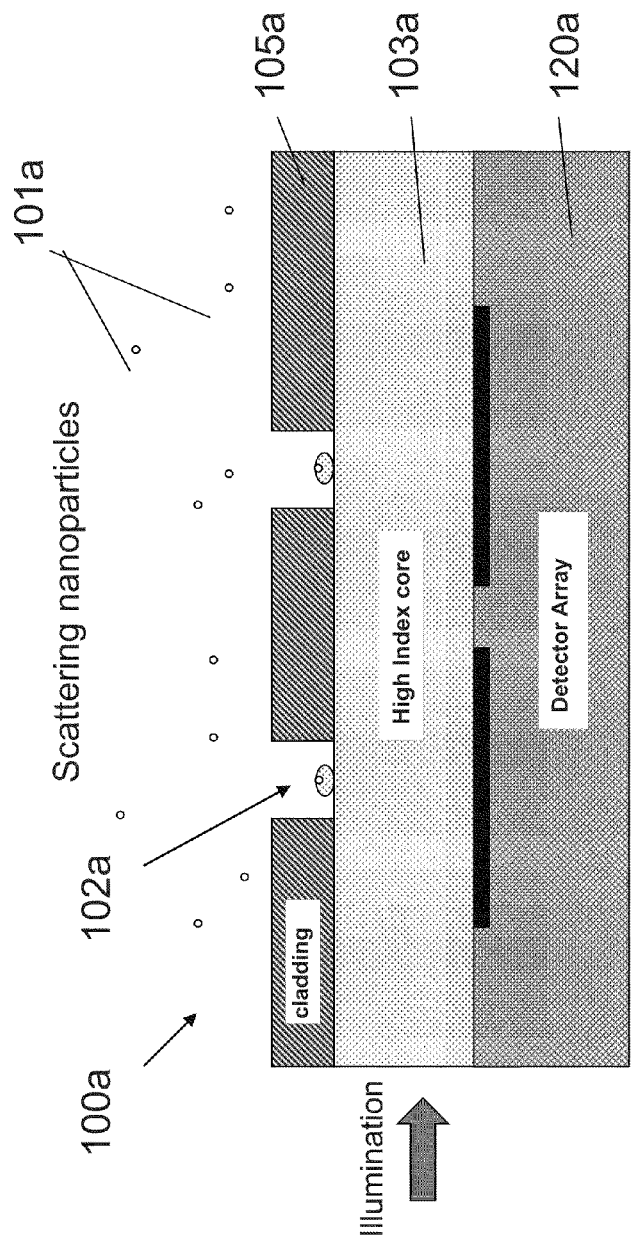
FIG. 25 is a schematic diagram of an analytical device with an array of reaction cells and waveguides configured for measuring scattering from nanoparticles.

Referring to FIG. 25, an integrated device 100a similar to the device of FIG. 1 is shown. The integrated device is configured for detection of scattering nanoparticles 101a while undergoing synthesis by DNA polymerase via the SMRT sequencing principle. The nanoparticles, such as gold or silver particles, are coupled to dNTPs to form phospholink analogs. The exemplary device is formed of a high index of refraction base substrate 103a, such as lithium niobate, into which illumination light is directed, in various respects to cause dark-field illumination or total internal reflection illumination of the top surface. The top surface has ZMWs 102a fabricated from a lower index of refraction material 105a, such as glass or alumina. The illumination creates the same observation volume confinement created in regular ZMWs, but the transparent nature of the top surface layer minimizes scattering of the incident light.

The backscattering of metallic nanoparticles is detected while they are processed by the enzyme. A different sized particle is conjugated to each of the four bases. In the exemplary device, differentiation of the bases is performed by the different scattering cross sections inherent in different particle sizes (corresponds with the sixth power of diameter), translating to different scattering "brightness" of the different bases. The bottom side of the integrated device carries an integrated detector 120a, such as a CCD camera, for detecting the scattered light from the ZMW. One will appreciate, therefore, that conventional optical components (e.g. objectives, lenses, mirrors, wedges) are not needed for detection.

One will appreciate from the description herein that the materials and configuration of the device may vary. Other metals or alloys can serve as a base substrate for the particles. The high index of refraction substrate can be different materials, glasses, polymers and the like. The high refraction index material can span the entire substrate or can be a thin layer on a carrier substrate configured as a waveguide. The top layer can be other materials, such as polymers or different glasses, or composite materials. The device can also be a multilayered structure, e.g., glass with an alumina coating. A thin layer can be placed between the core and cladding, e.g., a glass layer to enable surface chemistries.

Detection using the device shown in FIG. 25 may be carried out by directing different wavelengths to influence the scattering characteristics of different nanoparticle materials. A white light source (e.g. xenon lamp), which would enable spectral detection, can be used. In an exemplary embodiment, various input wavelengths are gated in time, and the differentiation of detection is based on time-gated detection.

The bottom side of the device can also carry a cladding layer, which can be of the same or different material of the top side, to provide a spacer between the device and the detection array. An optional mask is placed on the bottom surface to minimize crosstalk. In various embodiments, crosstalk is corrected computationally by cross-correlating signals from neighboring ZMWs. If the detector is spaced at some distance from the chip, spacer materials (e.g. solids, fluids, and gases) can be used to improve scattering light radiation efficiencies. In various embodiments, surface morphologies are built into the back side of the chip to enhance the direction of the scattering signals to the detection unit.

Unlike fluorescence detection, the integrated device of FIG. 25 generally reduces problems with respect to signal-to-noise (dye brightness) and photodamage. The device also does not require powerful lasers, sophisticated optics, and expensive detection technologies.

IX. System Synchronization and Dynamic Speed Control

The development of flexible high speed molecular sequencing engines can be enhanced with dynamic electronic controls based upon feedback from the molecular incorporation rate at each optode. The following description will detail methods and circuits to enable dynamic processing and data transmission that is related to the sequencing speed. In addition, methods to enable pipelined synchronous data streams from free running optode elements are described.

In various embodiments, an integrated detector array may be integrated with molecular sequencing reactors (e.g., SMRT™ cells, produced by Pacific Biosciences of California, Inc.), for example, asynchronous detection of incorporation events where the entire event is integrated and stored in the detection element for lowered bandwidth and highest sensitivity. Distributed processing at the optode-group level may provide intelligent data collection and compaction on-chip for low power and system complexity. For example, a group of optode elements may be grouped with shared I/O, processing and signal and sample distribution. Asynchronous events from these optode elements may be captured and buffered in these shared processing circuits. The overall average incorporation rate as well as the individual element rates may be variable based upon intentional and unintentional factors and can vary from sequence to sequence or even with a sequencing run. Methods to control the speed of the system at the global device or local levels may be configured to optimize the system for sensitivity and power.

At least two methods to provide a pipelined data stream from an ensemble of free running sensor elements may be considered. In one method, each element provides a signal that an event has occurred and that data is available for readout. This is generally termed an "interrupt-driven architecture." In another approach, a processing circuit regularly polls each element to look for locally stored events. This is generally termed a "polling-based architecture."

In the interrupt-based architecture, bandwidth must be available to handle many simultaneous events and buffering may be provided in the pipeline to equalize the transmission bandwidth. In polling-based architecture, space must be provided at the sensor element location as it waits to be transmitted down stream. The selection of either approach is driven by system constraints.

Figure 26:
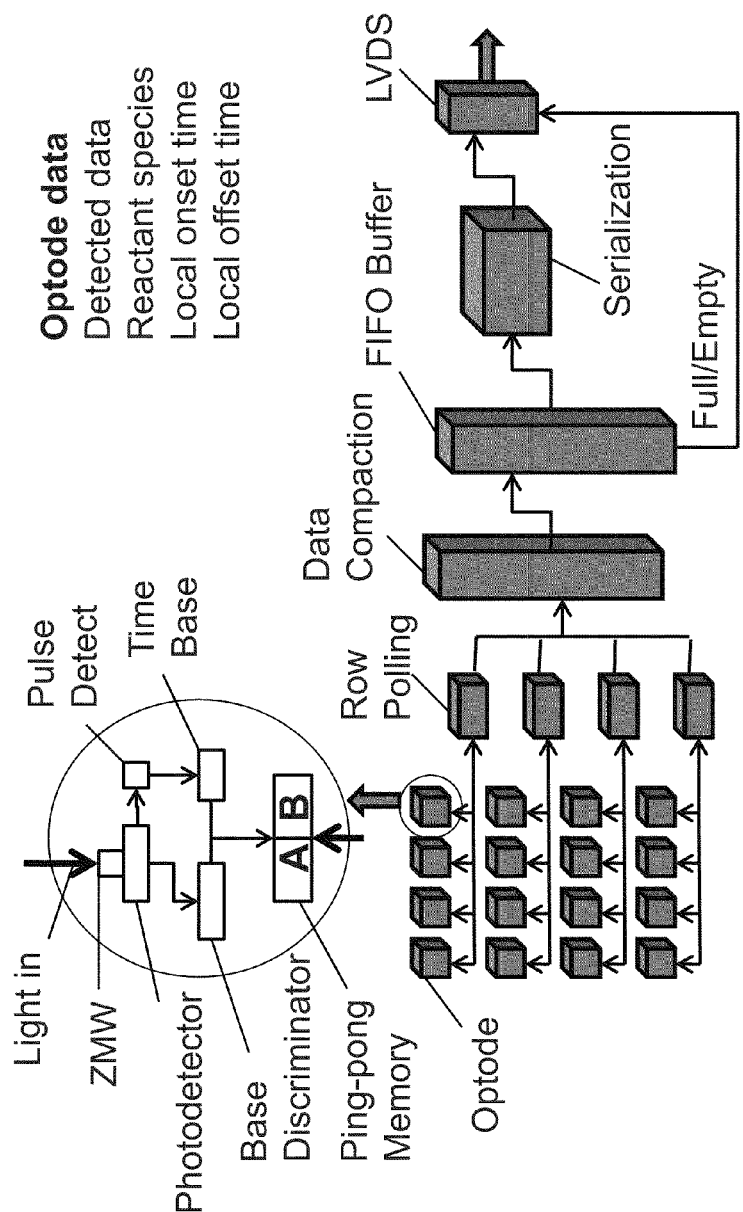
FIG. 26 is a schematic representation of a polling based approach to data synchronization in accordance with the present invention.

A polling-based architecture is shown in FIG. 26. In this figure, events are discriminated in the sensor element at the conclusion of the event, and each is stored in a buffer cell (analog or digital memory). Multiple storage elements must be provided to reduce data loss. Control of the buffer may include commonly used circuits to prevent the reading of buffer cells while they are being written by the sensor element circuits. As an example in FIG. 26, the pulse duration and signal type is shown but other representative data values may also be stored in addition to, on instead of the pulse duration and signal type. For example, each analog voltage that is integrated on multiple storage elements in the sensor pixel may be stored to be used downstream to determine the molecular tag identified during a sequencing event.

Circuits adjacent to an optode element ensemble are regularly interrogated. This may be accomplished with a local counter driving a multiplexer addressing circuit. This is generally referred to as a state machine register. Each optode memory element is addressed and the contents transferred to a common buffer. The contents may be digitized and interpreted. For example, if no event was detected during this polling duration, the data can be compacted to reduce output bandwidth. The state machine counter is incremented to address the next sensor element memory. At the end of the scan, the counter is reset to begin the next cycle. The data can now be understood to be a sequential stream of data mapped to known physical locations within a scan time. This data stream can be buffered in a memory array such as a first in first out (FIFO) buffer so that synchronous downstream transmission and pipeline processing is enabled.

In one example shown in FIG. 26, the data may be serialized and transmitted using commercial standard protocols such as low voltage differential signaling (LVDS). This method reduces the number of input output pads on the device. The balanced low-voltage differential signals also reduce on-chip noise and power consumption.

Figure 27:
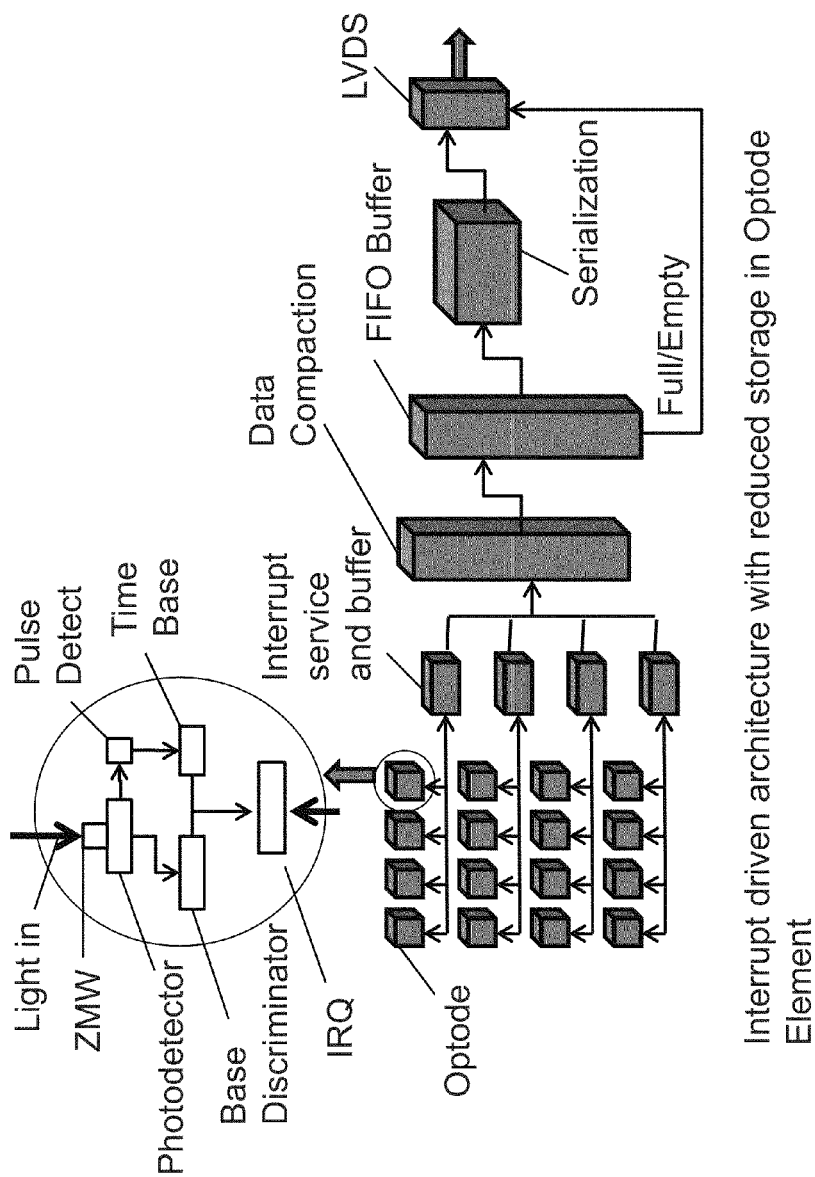
FIG. 27 is a schematic representation of an interrupt driven architecture with reduced storage in an optode element in accordance with the present invention.

An exemplary interrupt-driven system is shown in FIG. 27. In this example, reduced storage circuitry is required in the small optode element footprint. In this case, any vent, pulse-on, pulse-off, and data are detected and an interrupt request is made. The local clock is stored until the request is serviced. This value is transferred and stored in a buffer away from the optode element. The request is then cleared and the register re-armed. At the end of the event, the data are transferred to the output FIFO for downstream processing.

Typically polling based architectures are used when there is regular (high-duty) cycle event data and interrupt driven systems when there are sparse data events.

The FIFO buffer may contain flags (0b00-low, 0b01-normal, 0b10-nearly full, 0b11-full) and may output a respective signal with each sample. This may be used by the main controller to determine if the global or local clocks should be adjusted. Alternatively, these flags may be utilized with local clock generation or distribution networks to adjust performance based on the status of the flags.

Each local state machine may be increased or decreased in frequency based on local event dynamic to maximize performance and reduce data bandwidth. This is important when multiple groups of arrays on a device are used with different reagents and assays. Alternatively, the control of the digital data counter enables a device design to be used with high flexibility to changes in the assay parameters (i.e., temperature, reagent mix, sample type, concentration, etc.).

On will appreciate that interrupt-driven systems may utilize speed control with the status of row based buffers to reduce the probability of missed service request due to higher bandwidth interrupt frequency.

X. Photonic Event Detection and Sorting

The determination of a genomic sequence has been performed with an array of photonic chambers where an individual molecule can be interrogated for its attached fluorophore. In these systems, a free running camera monitors the chamber and reads the signal as it is emitted from the chamber. The signal timing is asynchronous from the camera exposure onset and to capture the majority of the events, a high frame rate is needed. Most events therefore are multiple frames in length. In these cases, the event signal is divided up into several frames and each frame contains a fixed component of read noise. These two effects combine to reduce the signal to noise ratio and the instrument accuracy.

In accordance with the present invention, the concept of an event detector is described. An event detector may integrate the full sequencing signal into one sample increasing the signal to noise ratio while reducing the overall bandwidth. Also in accordance with the present invention, various methods may be utilized to integrate portions of the signal into multiple integrating nodes for downstream classification if multiple species are present.

The detection of multiple sequence tags is needed for higher throughput devices without increasing off-chip bandwidth. To avoid having a requisite increase in tag brightness with increasing incorporation rates, increased sensitivity detection is needed. One method to accomplish both of these requirements is through event detection. By detecting the timing of an incorporation event, the full signal can be integrated in a single charge. This charge can be evaluated during integration to determine the tag species. Sensitivity may be increased while the intelligent pixel reduces the off-chip data rates.

Figure 28:
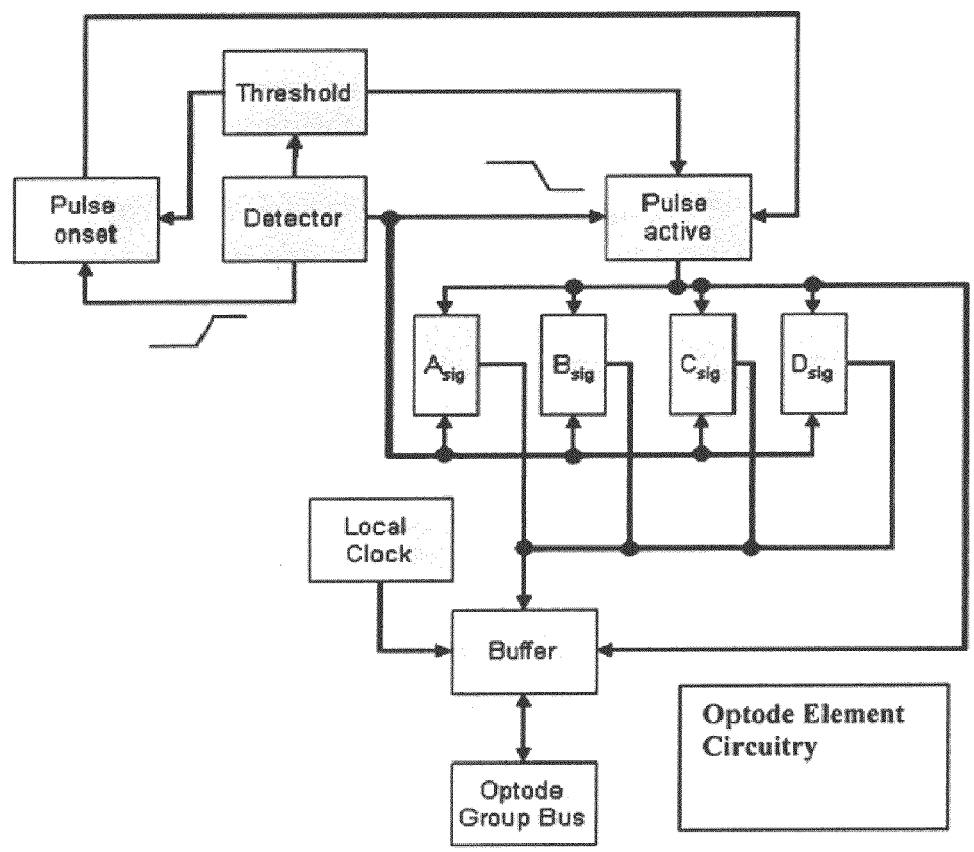
FIG. 28 is a schematic representation of a smart pixel for event logging with multi-species discrimination in accordance with the present invention.

In accordance with the present invention, a detector may be utilized to synchronize with a random event source such as a genetic sequence. An exemplary detector is shown in FIG. 28. This schematic details various circuit functions required to record and store an event that may be generated by one of a multitude of potential tags. As seen in the figure, the detector is connected to a trigger circuit which senses the onset and offset of an event. The signal is simultaneously routed to one of several storage nodes. These nodes integrate the charge from the event and are synchronized to a discriminating element of the unique tag. In some cases, the tag is associated with a property of the stimulus (i.e. the laser wavelength) and in others to a feature on the detector (i.e. the detection depth).

The signals are integrated while the event is active. The time stamps of the event and the integrated signals from each species are stored in a buffer. The system is envisioned as an ensemble of discrete SMRT™ cell processed elements, with each element operating asynchronously. A common readout circuit has been described above that takes the independent events and formats them for downstream processing.

Each of these circuit elements and their functions are described below. The combination of these functions performs a unique operation to integrate polymer sequencing into a micro-sized lab in a pixel.

Threshold Detection

In FIG. 28, a detector is designed with a threshold detector. This threshold can be set externally to provide flexibility to work with many input signals. In many cases, a threshold detector looks for changes in the temporal response in the input signal. The time derivative if the signal $\delta Q/\delta t$ is an effective method for pulse detection and easy to implement in a small integrated circuit. Variations on this approach with increased sensitivity are to use a Laplacian circuit with a $\delta^2 Q/\delta^2 t$ response.

Figure 29:
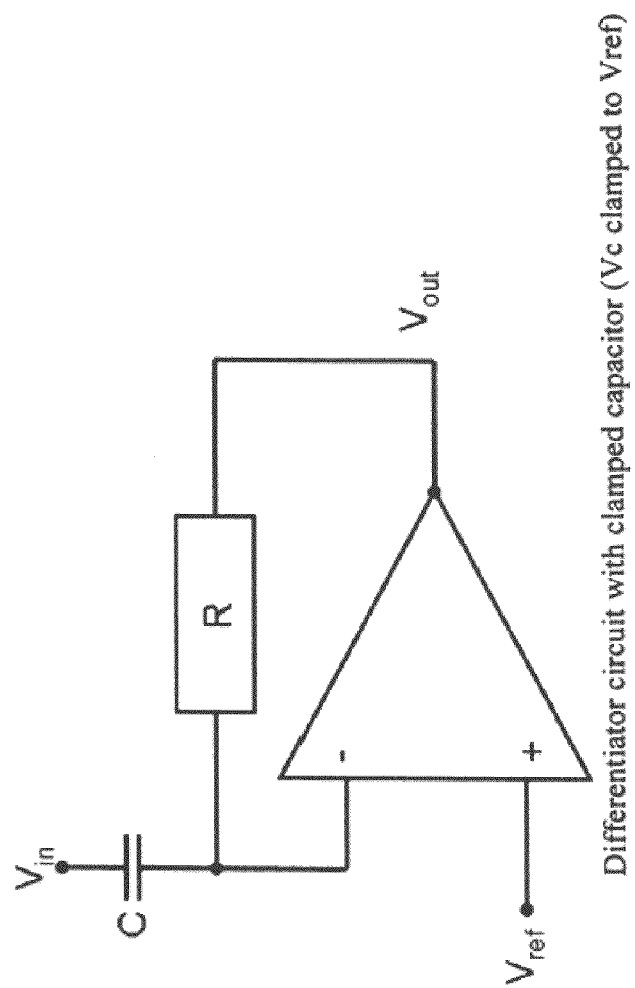
FIG. 29 is a schematic representation of differentiator circuit with a clamped capacitor in accordance with the present invention.
Figure 30:
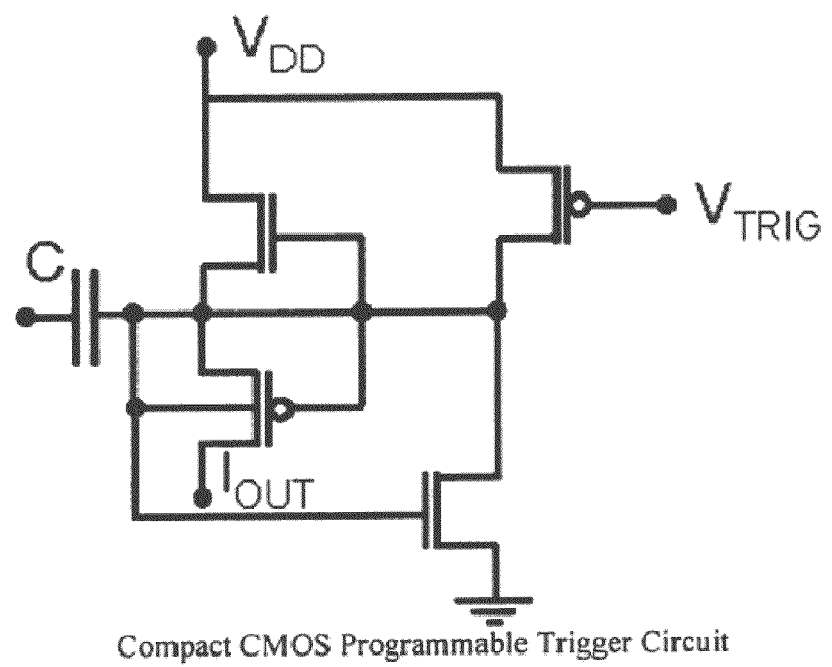
FIG. 30 is a schematic representation of a compact CMOS programmable trigger circuit in accordance with the present invention.
Figure 31:
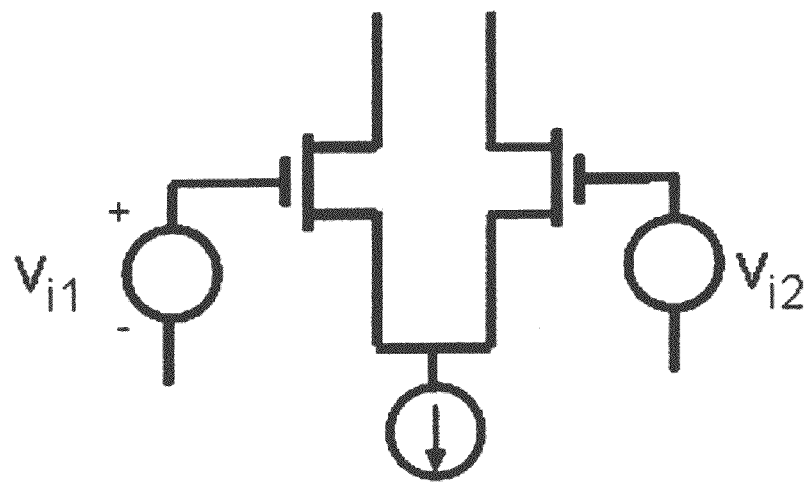
FIG. 31 is a schematic representation of differential amplifier for a trigger circuit in accordance with the present invention.

Simple RC circuits may also obtain this response as can operational amplifiers. A simple circuit, a zero-crossing threshold detector may be utilized to perform this function. An electronic comparator circuit with positive feedback (commonly known as a Schmitt trigger) may also supply this function. In various embodiments, it is important that the DC value be ignored as the pulse may reside on an arbitrary background signal. To remove this DC sensitivity, a clamped capacitor circuit design is disclosed. A schematic representation of a clamped capacitor differential circuit is shown in FIG. 29. Operating the capacitor in linear fashion emulates an ideal differentiator $I_C=C(dV/dT)$. The use of a high gain feedback circuit allows an indirect measure of $I_C$. The output of the circuit in FIG. 29 is proportional to the temporal derivative of the input signal as shown in the transfer function:

$$H(s)=-\tau s/(1+1/A^{(1+\tau s)})\approx \tau s \qquad \text{Eq. (1)}$$

For high gain, the output is proportional to the time constant. High gain may also be required to sense the signal temporal gradient of a few photoelectrons above the noise level. This input current can be generated from a source follower amplification of the photodiode voltage. A small capacity photodiode can induce a transconductance gain of over 100uV/e– at the source follower device. This voltage can be generated nondestructively (e.g., the photodetector charge is maintained).

A circuit is configured that is compact for in-pixel thresholding with sufficient sensitivity to detect a 2 photon gradient. This circuit can also be programmable for sensitivity (photons/sec) for flexible deployment with various chemistries and applications. The output current of this 4T CMOS amplifier is proportional to the input voltage gradient. The circuit consists of a sub-threshold transconductance amplifier (common source configuration) cascaded to a two transistor simple inverter. The use of the enhancement mode NMOS device provides sub-threshold biasing and requires an additional implantation step that is available in standard CMOS processes.

$$I_{out}=I_o e^{(Vout-Vcap)/Vt} \qquad \text{Eq. (2)}$$

A differential amplifier may also be used to determine the trigger based on a change in the temporal gradient in the photodiode voltage. While this circuit is not as compact, it may provide a voltage steering function with a sharp trigger point. The trigger is based on an integrated charge rather than the instantaneous voltage.

Pulse Onset

Figure 32:
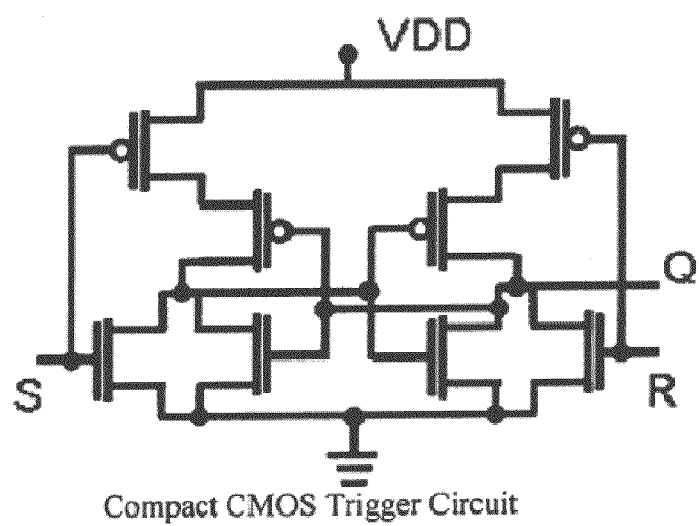
FIG. 32 is a schematic representation of compact CMOS trigger circuit in accordance with the present invention.

A switch that is activated by the threshold rising edge output may provides information about when the event has started. This output may be used to time stamp the beginning of an event with an internal counter (local or global) and to enable the segmentation of signal into tagged storage locations. A circuit that can perform this function is the D (data or delay) or RS (set-reset) type flip flop. An output pulse from the trigger circuit can be used to set the flip flop. The opposite current can be used to reset the circuit. The output Q of this circuit is the envelope of the incorporation event. The circuit in FIG. 32 will perform this function. The exemplary circuit is an eight transistor implementation in CMOS that has a regenerative feedback loop that locks the output to the set or reset conditions. It uses a pair of complimentary inverters with current sources. The outputs of each amplifier are connected to each other to provide feedback. By providing a pair of back-to-back diodes at the output of the trigger circuit, each thresholded crossing may be segregated to provide the set and reset inputs to the pulse duration circuit. This provides a full envelope detection circuit with programmability in twelve transistors, two diodes and one capacitor. One will appreciate that other configurations may also be used.

Storage Nodes and Control

Figure 33:
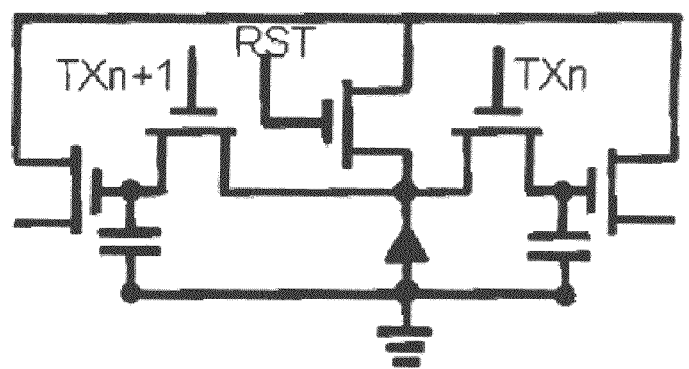
FIG. 33 is a schematic representation of two tap storage nodes from a photodetector with non-destructive monitoring in accordance with the present invention.

With reference to FIG. 33, a single photodetector element may be connected to several integrating nodes and sorted by external synchronization. It is disclosed that a multitude of transfer gates can be attached to the photodiode which can transfer the charge similar to a single stage CCD circuit to an adjacent floating diffusion capacitance. This capacitance will hold this charge. This charge may be monitored without disturbing the charge by connecting a gate element of a MOS device (JFET, MOSFET, etc) to a plate of the floating diffusion capacitance. The capacitance may be reset at anytime and each capacitance cleared independently. It is also disclosed that the capacitors can be partially reset by applying a bias in the linear region of the amplifier and can be used during the event capture to extend the dynamic range of the detector. It is also disclosed that multiple storage nodes can integrate charge from a multiple set of photodetectors arranged either laterally or vertically to assist in discriminating the source of the event.

Buffer Memory and Timing

Figure 34:
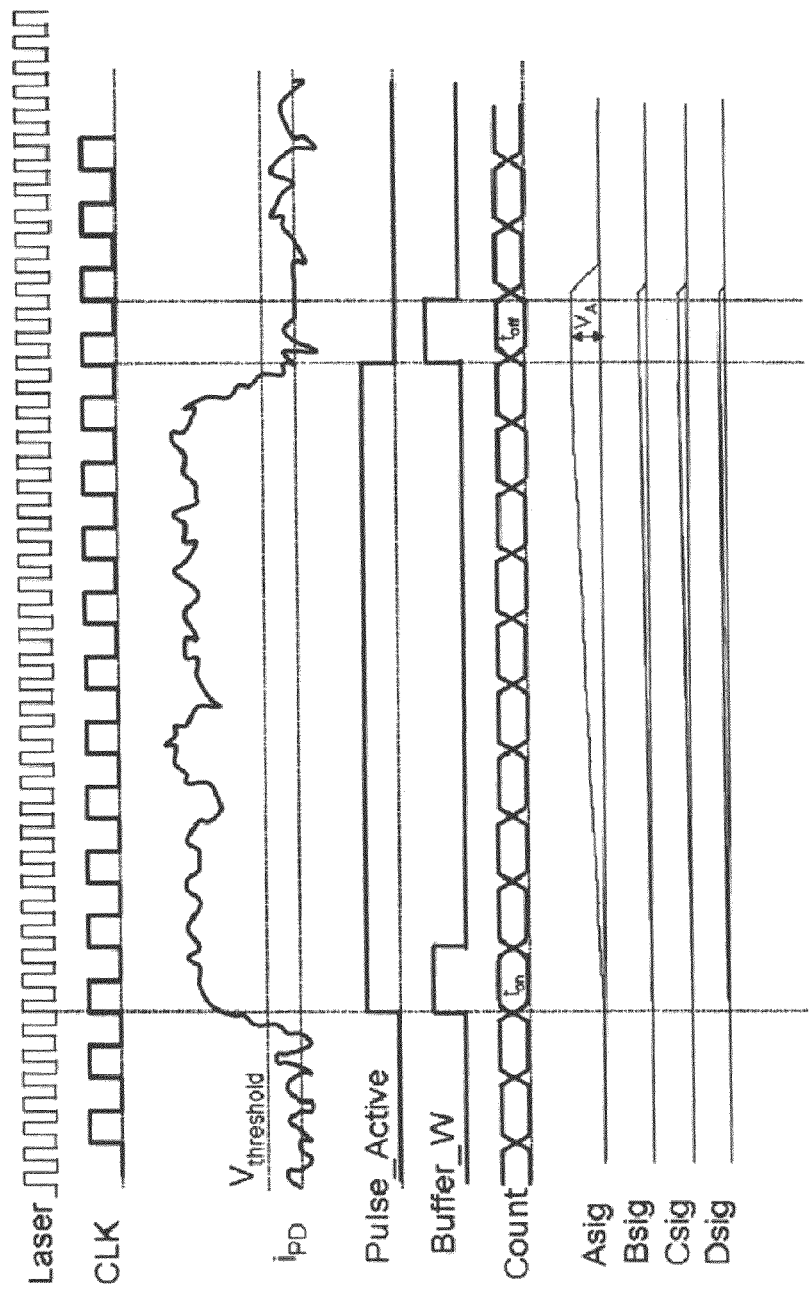
FIG. 34 is a representative timing diagram of an event capture circuit sin accordance with the present invention.

An edge detection of the Pulse Envelope can be used as a trigger to signal the onset and offset of the event and transfer relevant information to buffer prior to readout. A multiple event buffer may be used in this circuit so that rapidly occurring events can be captured faster than the readout can support. Stored events can be read out asynchronously from the events elapsed time. For example, at the pulse onset, the storage nodes can be reset and the time recorded in buffer. At the pulse offset, the integrated signals from each of the storage nodes can be stored in analog or digital buffer and the offset time recorded. The use of the offset falling edge can also re-arm the circuit for the next event. A representative timing diagram of this operation is shown in FIG. 34. A globally transmitted or locally generated clock can be used to record the critical times of the event. Downstream processing is envisioned to perform mathematical operations to determine specific timing parameters such as pulse duration and time between pulses.

XI. Other Integrated Elements

In addition to optical, fluidic and electrical elements, a variety of other elements may optionally be integrated into the unified device structure. By way of example, security features may be fabricated into the device structure to prevent counterfeiting, prevent unauthorized reuse, identify a specific application for which a device is intended, etc. In particular, because the device includes integrated electronics, it can also be fabricated to include electronic identification elements, such as RFID tags, key elements, serial number encoding, use indicators, etc. These identifiers may be used in preventing unauthorized use of a given device, or may be used to ensure that a device is only used for its intended application. Inclusion of such encoding, sensor and other electronic components can be accomplished through conventional IC fabrication processes during the fabrication of the overall device. In addition to precoded elements, the devices may also include storage functions to record data associated with a given analysis, e.g., diagnostic functions, to identify when and if a failure occurred, assigning sample data to a given device, e.g., patient name and tests run.

Upon interfacing the device with an overall instrument, the instrument may download whatever data is provided by the device's identifier component(s), permitting tracking of the type of device, the desired application, whether the device has been reused, or constitutes a counterfeit device. Following this, the instrument may take whatever actions are preprogrammed for the identifier that is read, such as running a particular type of application, placing orders for additional devices, shutting down or suspending operation, etc.

It is to be understood that the above description is intended to be illustrative and not restrictive. It readily should be apparent to one skilled in the art that various embodiments and modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. In describing the invention herein, references to any element in the singular will include references to plural, and vice versa, unless it is clear from the context that this was explicitly not intended. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated herein by reference in its entirety for all purposes.

What is claimed is:

1. A device for measuring analytical reactions comprising a two dimensional array of elements comprising optode array components, fluidic input components, and illumination input components:
   (a) the optode array components each comprising an array of optode elements, each optode element comprising:
      a nanoscale aperture within an aperture layer, the aperture forming a fluid receiving nanoscale well for receiving a fluid including fluorescent species;
      above the aperture layer a fluidic layer in fluidic contact with the nanoscale well, the fluidic layer comprising an array of fluidic conduits, each fluidic conduit extending across a plurality of optode elements;
      below the aperture layer a waveguide layer that provides illumination to the nanoscale well, the waveguide layer comprising an array of channel waveguides, each channel waveguide extending across a plurality of optode elements;
      below the waveguide layer a transmission layer that transmits light emitted from the fluorescent species in the nanoscale well to a detector layer; and
      below the transmission layer the detector layer comprising one or more detectors which receives and detects the emitted light from the nanoscale well and transmitted through the transmission layer;
   (b) the fluidic input components connected to an edge of the optode array component, the fluidic input components each comprising a port on its top surface for introduction of fluids, and fluidic conduits fluidically connected to the port and connected to fluidic conduits in the reactor component; and
   (c) the illumination input components connected to an edge of the optode array component, the illumination input components each having an optical port on its top surface for introduction of illumination light, and waveguides connected to the optical port and connected to waveguides of the optode array component.

2. The device of claim 1 wherein each optode element comprises an optical tunnel that preferentially directs optical signals from the nanoscale well to the one or more detectors.

3. The device of claim 1 wherein each optode array component comprises from 100 to 100,000 optode elements.

4. The device of claim 1 wherein the detector layer comprises embedded circuits for processing output data from the one or more detectors.

5. The device of claim 4 wherein the embedded circuits filter background noise from the one or more detectors.

6. The device of claim 4 further comprising an amplifier for amplifying the output data.

7. The device of claim 6 further comprising an analog to digital converter.

8. The device of claim 1 wherein a combination of an optode array component, a fluidic input component, and an illumination input component is an optode array group, and the device comprises from about 100 to about 1,000 optode array groups.

9. The device of claim 1 wherein there is little or no free space between components.

10. The device of claim 1 wherein the detector layer can be reversibly separated from the portion of the array comprising the nanoscale well.

11. The device of claim 1 wherein the illumination input components and fluidic input components are provided in alternating rows.

12. The device of claim 1 wherein each optode array component is connected to two fluidic input components.

13. The device of claim 1 wherein each optode array component is connected to two illumination input components.

* * * * *